US009884100B2

(12) United States Patent
Valenzuela et al.

(10) Patent No.: US 9,884,100 B2
(45) Date of Patent: Feb. 6, 2018

(54) ***LUTZOMYIA LONGIPALPIS* POLYPEPTIDES AND METHODS OF USE**

(71) Applicants: The United States of America as represented by the Secretary of the Department of Health and Human Services, Washington, DC (US); Fundaçao Oswaldo Cruz (FIOCRUZ), Rio de Janeiro (BR)

(72) Inventors: Jesus G. Valenzuela, Gaithersburg, MD (US); Jose M. C. Ribeiro, Rockville, MD (US); Aldina Barral, Bahia (BR); Manoel Barral Netto, Bahia (BR); Claudia I. Brodskyn, Bahia (BR); Regis Gomes, Bahia (BR)

(73) Assignees: The United States of America as represented by the Secretary of the Department of Health and Human Services, Washington, DC (US); Fundacão Oswaldo Cruz (FIOCRUZ) (BR)

( * ) Notice: Subject to any disclaimer, the term of this patent is extended or adjusted under 35 U.S.C. 154(b) by 0 days.

(21) Appl. No.: 15/175,329

(22) Filed: Jun. 7, 2016

(65) Prior Publication Data

US 2016/0279211 A1 Sep. 29, 2016

Related U.S. Application Data

(62) Division of application No. 14/802,168, filed on Jul. 17, 2015, now Pat. No. 9,382,302, which is a division of application No. 14/097,991, filed on Dec. 5, 2013, now Pat. No. 9,120,867, which is a division of application No. 12/350,179, filed on Jan. 7, 2009, now Pat. No. 8,628,780, which is a division of application No. 10/533,811, filed as application No. PCT/US03/34453 on Oct. 29, 2003, now Pat. No. 7,485,306.

(60) Provisional application No. 60/422,303, filed on Oct. 29, 2002.

(51) Int. Cl.

| | |
|---|---|
| ***A61K 39/008*** | (2006.01) |
| ***C07K 14/435*** | (2006.01) |
| ***C12N 15/63*** | (2006.01) |
| ***C07K 14/44*** | (2006.01) |
| ***A61K 39/00*** | (2006.01) |
| ***C07K 16/18*** | (2006.01) |
| ***C07K 16/20*** | (2006.01) |
| *A61K 38/00* | (2006.01) |

(52) U.S. Cl.
CPC ........ *A61K 39/008* (2013.01); *A61K 39/0003* (2013.01); *C07K 14/43577* (2013.01); *C07K 14/44* (2013.01); *C07K 16/18* (2013.01); *C07K 16/20* (2013.01); *C12N 15/63* (2013.01); *A61K 38/00* (2013.01); *A61K 2039/53* (2013.01); *A61K 2039/57* (2013.01); *A61K 2039/575* (2013.01); *A61K 2039/58* (2013.01); *C07K 2317/21* (2013.01)

(58) Field of Classification Search
CPC ............ A61K 2039/53; A61K 39/0003; A61K 39/00; A61K 38/00; A61K 2039/58; A61K 39/008; A61K 45/06; C07K 14/43577; C07K 14/43563; C07K 14/44; C07K 16/18
See application file for complete search history.

(56) References Cited

U.S. PATENT DOCUMENTS

| | | | | |
|---|---|---|---|---|
| 5,397,772 | A | 3/1995 | Ribeiro et al. | |
| 9,382,302 | B2 * | 7/2016 | Valenzuela ........ | A61K 39/0003 |

FOREIGN PATENT DOCUMENTS

| | | |
|---|---|---|
| WO | WO 95/06729 | 3/1995 |
| WO | WO 02/102324 | 12/2002 |
| WO | WO 2004/027041 | 4/2004 |

OTHER PUBLICATIONS

Adler et al., "The mouthparts, alimentary tract and salivary apparatus of the female *Phlebotomus papatasi*," *Ann. Trop. Med. Parasitol.* 20:109, 1926.
Barral et al., "Human immune response to sand fly salivary gland antigens: a useful epidemiological marker?" *Am. J. Trop. Med. Hyg.* 62:740-745, 2000.
Belkaid et al., "A natural model of *Leishmania major* infection reveals a prolonged "silent" phase of parasite amplification in the skin before the onset of lesion formation and immunity," *J. Immunol.* 165:969-977, 2000.
Belkaid et al., "Delayed-type hypersensitivity to *Phlebotomus papatasi* sand fly bite: an adaptive response induced by the fly?" *Proc. Natl. Acad. Sci. USA* 97:6704-6709, 2000.
Belkaid et al., "Development of a natural model of cutaneous leishmaniasis: powerful effects of vector saliva and saliva preexposure on the long-term outcome of *Leishmania major* infection in the mouse ear dermis," *J. Exp. Med.* 188:1941-1953, 1998.

(Continued)

*Primary Examiner* — Padmavathi Baskar
(74) *Attorney, Agent, or Firm* — Klarquist Sparkman, LLP

(57) ABSTRACT

Substantially purified salivary *Lu. longipalpis* polypeptides, and polynucleotides encoding these polypeptides are disclosed. Vectors and host cells including the *Lu. longipalpis* polynucleotides are also disclosed. In one embodiment, a method is disclosed for inducing an immune response to sand fly saliva. In other embodiments, methods for treating, diagnosing, or preventing *Leishishmaniasis* are disclosed.

8 Claims, 2 Drawing Sheets

(56) References Cited

OTHER PUBLICATIONS

Bowie et al., "Deciphering the Message in Protein Sequences: Tolerance to Amino Acid Substitutions," *Science*, vol. 247:1306-1310, 1990.
Charlab et al., "Toward an understanding of the biochemical and pharmacological complexity of the saliva of a hematophagous sand fly *Lutzomyia longipalpis*," *Proc. Natl. Acad. Sci., USA.* 96(26):15155-15160, 1999.
Enserink, "Sand Fly Saliva May Be Key to New Vaccine," *Science*, 293:1028, 2001.
Gillespie et al., "The immunomodulatory factors of bloodfeeding arthropod saliva," *Parasite Immunology*, 22(7):319-331, 2000.
Gomes et al., "Seroconversion against *Lutzomyia longipalpis* Saliva Concurrent with the Development of Anti-*Leishmania chagasi*Delayed-Type Hypersensitivity," *Journal of Infectious Diseases*, 186(10):1530-1534, 2002.
Gomes et al., "Immunity to a salivary protein of a sand fly vector protects against the fatal outcome of visceral leishmaniasis in a hamster model," *PNAS*, 105(22):7845-7850, 2008.
Gurunathan et al., "Vaccination with DNA encoding the immunodominant LACK parasite antigen confers protective immunity to mice infected with *Leishmania major*," *J. Exp. Med.* 186:1137-1147, 1997.
Gurunathan et al., "Vaccine requirements for sustained cellular immunity to an intracellular parasitic infection," *Nat. Med.* 4:1409-1415, 1998.
Haskó et al., "Adenosine inhibits IL-12 and TNF—[alpha] production via adenosine A2a receptor—dependent and independent mechanisms," *FASEB J.*, 14(13):2065-2074, 2000.
Haskó et al., "Adenosine receptor agonists differentially regulate IL-10, TNF-alpha, and nitric oxide production in RAW 264.7 macrophages and in endotoxemic mice," *J. Immunol.*, 157(10):4634-4640, 1996.
Houghton et al., "Relative Importance of Position and Individual Amino Acid Residues in Peptide Antigen-Antibody Interactions: Implications in the Mechanism of Antigenic Drift and Antigenic Shift," in *Vaccines 86—New Approaches to Immunization*, Ed. Fred Brown, Cold Spring Harbor Laboratory, pp. 21-25, 1986.
Kamhawi et al., "Protection against cutaneous leishmaniasis resulting from bites of uninfected sand flies," *Science* 290:1351-1354, 2000.
Kamhawi et al., "The Biological and Immunomodulatory Properties of Sand Fly Saliva and Its Role in the Establishment of *Leishmania* infections," *Microbes Infect.*, 2(14): 1765-1773, 2000.
Katz et al., "Adenosine, AMP, and protein phosphatase activity in sand fly saliva," *Am. J. Trop. Med. Hyg.* 62:145-150, 2000.
Killick-Kendrick, Biology of *Leishmania* in phlebotomine sand flies. In Biology of the Kinetoplastida. W. Lumsden and D. Evans, editors. Academic Press, New York. 395, 1979.
Killick-Kendrick et al., "Mark-release-recapture of sand flies fed on leishmanial dogs: the natural life-cycle of *Leishmania infantum* in Phlebotomus ariasi," *Parassitologia*, 44(1-2): 67-71, 2002.
Lal et al., "Anti-mosquito midgut antibodies block development of *Plasmodium falciparum* and *Plasmodium vivax* in multiple species of *Anopheles* mosquitoes and reduce vector fecundity and survivorship," PNAS, 98:5228-5233, 2001.
Lederman et al., "A single amino acid substitution in a common African allele of the CD4 molecule ablates binding of the monoclonal antibody, OKT4," *Mol. Immunol.*, 28:1171-1181, 1991.
Lerner et al., "Isolation of maxadilan, a potent vasodilatory peptide from the salivary glands of the sand fly *Lutzomyia longipalpis*," *J. Biol. Chem.*, 266(17):11234-11236, 1991.
Li et al., "β-Endorphin omission analogs: Dissociation of immunoreactivity from other biological activities," *PNAS USA*, 77:3211-3214, 1980.
Makoul et al., "Prostaglandin E2 inhibits the activation of cloned T cell hybridomas," *J. Immunol.*, 134(4):2645-2650, 1985.
Mellanby, "Man's Reaction to Mosquito Bites," *Nature* 158(4016):554-555, 1946.
Méndez et al., "The potency and durability of DNA- and protein-based vaccines against *Leishmania major* evaluated using low dose, intradermal challenge," *J. Immunol.* 166(8):5122-5128, 2001.
Milleron et al., Antigenic diversity in maxadilan, a salivary protein from the sand fly vector of American visceral leishmaniasis, *Am. J. Trop. Med. Hyg.*, 70:286-293, 2004.
Modi et al., "A simple technique for mass rearing *Lutzomyia longipalpis* and *Phlebotomus papatasi* (Diptera: Psychodidae) in the laboratory," *J. Med. Ent.* 20:568-569, 1983.
Morris et al., "Sandfly Maxadilan Exacerbates Infection with *Leishmania major* and Vaccinating Against It protects Against *L. major* Infection," *J. Immunol.*, 167(9): 5226-5230, 2001.
Nong et al., "Peptides encoded by the calcitonin gene inhibit macrophage function," *J. Immunol.*, 143(1):45-49, 1989.
Qureshi et al., "Immunomodulatory properties of maxadilan, the vasodilator peptide from sand fly salivary gland extracts," *Am. J. Trop. Med. Hyg.*, 54(6):665-671, 1996.
Ribeiro et al., "Blood-finding strategy of a capillary-feeding sandfly, *Lutzomyia longipalpis*," *Comp. Biochem. Physiol.*, 83(4):683-686, 1986.
Ribeiro et al., "Salivary apyrase activity of some Old World phlebotomine sand flies," *Insect Biochem.* 19:409-412, 1989.
Ribeiro et al., "A Novel Vasodilatory Peptide from the Salivary Glands of the Sand Fly *Lutzomyia longipalpis*," *Science*, 243:212-214, 1989.
Ribeiro et al., "Salivary glands of the sand fly Phlebotomus papatasi contain pharmacologically active amounts of adenosine and 5'-AMP," *J. Exp. Biol.*, 202(Pt. 11):1551-1559, 1999.
Sacks et al., "The Immunology of Susceptibility and Resistance to *Leishmania Major* in Mice," *Nat. Rev. Immunol.*, 2: 845-858, 2002.
Santoli et al., "Prostaglandin E precursor fatty acids inhibit human IL-2 production by a prostaglandin E-independent mechanism," and Zurier, *J. Immunol.*, 143(4):1303-1309, 1989.
Sjölander et al., "Induction of a Th1 immune response and simultaneous lack of activation of a Th2 response are required for generation of immunity to leishmaniasis," *J. Immunol.* 160:3949-3957, 1998.
Smelt et al., "B cell-deficient mice are highly resistant to *Leishmania donovani* infection, but develop neutrophil-mediated tissue pathology," *J. Immunol.* 164:3681-3688, 2000.
Soares et al., "The vasoactive peptide maxadilan from sand fly saliva inhibits TNF-alpha and induces IL-6 by mouse macrophages through interaction with the pituitary adenylate cyclase-activating polypeptide (PACAP) receptor," *J. Immunol.* 160:1811-1816, 1998.
Soares et al., "*Lutzomyia longipalpis* (Diptera: Psychodidae: Phlebotominae): a review," *Annals of the Brazilian Academy of Sciences*, 75:301-330, 2003.
Sousa et al., Mem. Inst. Oswaldo Cruz, vol. 96, No. 7, Rio de Janeiro, Oct. 2001.
Stockman et al., "The effect of prostaglandins on the in vitro blastogenic response of human peripheral blood lymphocytes," *Exp. Hematol.*, 2(2):65-72, 1974.
Theodos et al., "Analysis of enhancing effect of sand fly saliva on *Leishmania* infection in mice," *Infect. Immun.* 59:1592-1598, 1991.
Titus et al., "Salivary gland lysates from the sand fly *Lutzomyia longipalpis* enhanced *Leishmania* infectivity," *Science* 239:1306-1308, 1988.
Titus et al., "The role of vector saliva in transmission of arthropod-borne disease," *Parasitology Today* 6(5):157-160, 1990.
Valenzuela et al., "Identification of the most abundant secreted proteins from the salivary glands of the sand fly *Lutzomyia longipalpis*, vector of *Leishmania chagasi*," *The Journal of Experimental Biology*, 207(21):3717-3729, 2004.
Valenzuela et al., "The salivary apyrase of the blood-sucking sand fly *Phlebotomus papatasi* belongs to the novel Cimex family of apyrases," *J. Experimental Biology*, 204:229-237, 2001.
Valenzuela et al., "Toward a defined anti-*Leishmania* vaccine targeting vector antigens: characterization of a protective salivary protein," *J. Exp. Med.* 194(3):331-342, 2001.
Valenzuela et al., "The D7 family of salivary proteins in blood sucking diptera," *Insect Molecular Biology*, 11: 149-155, 2002.
Volf and Rohousová, "Species-specific antigens in salivary glands of phlebotomine sandflies," *Parasitology*, 122: 37-41, 2001.

(56) References Cited

OTHER PUBLICATIONS

Volf et al., "Salivary proteins and glycoproteins in phlebotomine sandflies of various species, sex and age," *Medical and Veterinary Entomology*, 14: 251-256, 2000.
Webster, "Role of purines in lymphocyte function," *Asian Pac. J. Allergy Immunol.*, 2(2):311-317, 1984.
Xu et al., "Protection against leishmaniasis by injection of DNA encoding a major surface glycoprotein, gp63, of *L. major,*" *Immunology* 84:173-176, 1995.
"Researchers hone in on leishmaniasis vaccine," *Journal of the American Veterinary Medical Association*, Sep. 15, 2001 (online article, no author credited).
Database A_Genseq_Jun. 29, 2004 Accession No. ABB71995, Mar. 26 2002, 1 page.
Database A_Genseq_June 29, 2004 Accession No. ABG18028, Feb. 18, 2002, 1 page.
Database SPTrEMBL Accession No. Q95WD8, Dec. 19, 2001, 6 pages.
Database SPTrEMBL Accession No. Q23404, Jun. 6, 1998, 5 pages.
Database A_Genseq_Jun. 29, 2004 Accession No. AAG03191, Oct. 6, 2000, 1 page.
Database A_Genseq_Jun. 29, 2004 Accession No. ABG24332, Feb. 18, 2002, 1 page.
Database SPTrEMBL Accession No. Q9HNC7 Mar. 16, 2001, 4 pages.
Database A_Genseq_Jun. 29, 2004 Accession No. AAU48010, Feb. 27, 2002, 1 page.
Database SPTrEMBL Accession No. Q95WE2, Dec. 1, 2001, 1 page.
Database PIR_78 Accession No. G81431, Mar. 31, 2000, 2 pages.
Database SPTrEMBL Accession No. Q9XZ44, Nov. 12, 1999, 4 pages.
Database A_Genseq_Jun. 29, 2004 Accession No. AAB94843 Jun. 26, 2001, 1 page.
Database A_Genseq_Jun. 29, 2004 Accession No. ABB61398, Mar. 26, 2002, 1 page.
Database A_Genseq_Jun. 29, 2004 Accession No. AAB42952, Feb. 8, 2001, 1 page.
Database SPTrEMBL Accession No. Q9RVD4, May 1, 2000, 1 page.
Database SPTrEMBL Accession No. Q95V88, Dec. 1, 2001, 2 pages.
Database PIR_78 Accession No. B64020, Sep. 10, 1999, 1 page.
Database A_Genseq_Jun. 29, 2004 Accession No. ABB57882, Mar. 26, 2002, 1 page.
Database PIR_78 Accession No. T50116, Jun. 9, 2000, 1 page.
Database PIR_78 Accession No. F90270, May 24, 2001, 1 page.
Database A_Genseq_Jun. 29, 2004 Accession No. ABB58845, Mar. 26, 2002, 1 page.
Database A_Genseq_Jun. 29, 2004 Accession No. AAB83185, Jul. 9, 2001, 1 page.
Database Swissprot_42 Accession No. Q57124, Nov. 10, 1997, 1 page.

* cited by examiner

SEQUENCE LISTING

```
<160> NUMBER OF SEQ ID NOS: 73

<210> SEQ ID NO 1
<211> LENGTH: 271
<212> TYPE: PRT
<213> ORGANISM: Lutzomyia longipalpis

<400> SEQUENCE: 1

Met Leu Gln Ile Lys His Leu Leu Ile Phe Val Gly Leu Leu Val Val
1               5                   10                  15

Val Asn Ala Gln Ser Asn Tyr Cys Lys Gln Glu Ser Cys Ser Ser Gly
            20                  25                  30

Gly Val Glu Arg Pro His Ile Gly Cys Lys Asn Ser Gly Asp Phe Ser
        35                  40                  45

Glu Thr Cys Ser Gly Asp Ala Glu Ile Val Lys Met Asp Lys Lys Lys
```

-continued

```
    50                  55                  60

Gln Asn Leu Leu Val Lys Met His Asn Arg Leu Arg Asp Arg Phe Ala
65                  70                  75                  80

Arg Gly Ala Val Pro Gly Phe Ala Pro Ala Ala Lys Met Pro Met Leu
                85                  90                  95

Lys Trp Asn Asp Glu Leu Ala Lys Leu Ala Glu Tyr Asn Val Arg Thr
            100                 105                 110

Cys Lys Phe Ala His Asp Lys Cys Arg Ala Ile Asp Val Cys Pro Tyr
        115                 120                 125

Ala Gly Gln Asn Leu Ala Gln Met Met Ser Tyr Pro Thr His Arg Asp
    130                 135                 140

Leu Asn Tyr Val Leu Lys Asn Leu Thr Arg Glu Trp Phe Trp Glu Tyr
145                 150                 155                 160

Arg Trp Ala Lys Gln Ser Gln Leu Asp Asn Tyr Val Gly Gly Pro Gly
                165                 170                 175

Lys Asp Asn Lys Gln Ile Gly His Phe Thr Ala Phe Val His Glu Lys
            180                 185                 190

Thr Asp Lys Val Gly Cys Ala Ile Ala Arg Phe Thr Asn Glu His Asn
        195                 200                 205

Phe Lys Glu Thr Leu Leu Ala Cys Asn Tyr Cys Tyr Thr Asn Met Met
    210                 215                 220

Lys Glu Arg Ile Tyr Thr Gln Gly Lys Pro Cys Ser Gln Cys Gln Ser
225                 230                 235                 240

Lys Lys Cys Gly Pro Val Tyr Lys Asn Leu Cys Asp Pro Ser Glu Lys
                245                 250                 255

Val Asp Pro Thr Pro Asp Val Leu Lys Gln Trp Lys His Gly Lys
            260                 265                 270


<210> SEQ ID NO 2
<211> LENGTH: 905
<212> TYPE: DNA
<213> ORGANISM: Lutzomyia longipalpis

<400> SEQUENCE: 2

agttgtggag cttttggtca ttttacgtga tgttgcaaat taaacatctt ctgatttttg      60

tgggattgct cgtggttgtt aatgcacaga gcaattactg caaacaggaa tcgtgctcat     120

cgggaggtgt tgagagaccc catattgggt gcaaaaactc tggagatttt tccgaaactt     180

gctccggaga tgcagaaatt gttaagatgg acaagaagaa gcagaacctc cttgtgaaaa     240

tgcacaatcg cctgagagat agatttgctc gtggtgcagt gccaggtttt gcaccagctg     300

cgaaaatgcc aatgcttaaa tggaacgatg aactggccaa attggcagag tacaacgtga     360

gaacgtgcaa atttgcccac gataaatgcc gcgcaattga tgtctgcccc tatgctggac     420

agaatctagc tcaaatgatg tcctatccta cccatcgaga tctaaactat gttcttaaga     480

atctcacaag ggaatggttc tgggagtaca gatgggctaa gcaatctcag cttgataatt     540

acgtgggtgg tcctgggaaa gacaacaaac aaattggaca tttcacagct tttgtgcatg     600

agaaaacaga caaagttgga tgcgctatag ctcgatttac aaatgagcac aattttaagg     660

agaccctcct agcttgcaac tactgctaca cgaatatgat gaaggagagg atctacacgc     720

agggaaaacc ttgttcacag tgtcagagca aaaagtgtgg gccagtctac aagaacctgt     780

gtgatccttc ggagaaggtt gatccaactc ctgatgtcct taagcaatgg aagcatggaa     840

aatgattatt aagctcactt caaatgtttc caatccaaaa aaaaaaaaaa aaaaaaaaaa     900
```

aaaaa 905

<210> SEQ ID NO 3
<211> LENGTH: 159
<212> TYPE: PRT
<213> ORGANISM: Lutzomyia longipalpis

<400> SEQUENCE: 3

Met Leu Leu Arg Ser Leu Phe Val Leu Phe Leu Ile Phe Leu Thr Phe
1 5 10 15

Cys Asn Ala Glu Glu Glu Leu Ile Glu Arg Lys Leu Thr Gly Lys Thr
20 25 30

Ile Tyr Ile Ser Thr Ile Lys Leu Pro Trp Phe Gln Ala Leu Asn His
35 40 45

Cys Val Lys Asn Gly Tyr Thr Met Val Ser Ile Lys Thr Phe Glu Glu
50 55 60

Asn Lys Glu Leu Leu Lys Glu Leu Lys Arg Val Ile Arg Thr Glu Asp
65 70 75 80

Thr Gln Val Trp Ile Gly Gly Leu Lys His His Gln Phe Ala Asn Phe
85 90 95

Arg Trp Val Ser Asp Gly Ser His Val Ala Thr Ala Ser Gly Tyr Thr
100 105 110

Asn Trp Ala Pro Gly Glu Pro Ala Asp Ser Phe Tyr Tyr Asp Gln Phe
115 120 125

Cys Met Ala Met Leu Phe Arg Lys Asp Gly Ala Pro Trp Asp Asp Leu
130 135 140

Asn Cys Trp Val Lys Asn Leu Phe Val Cys Glu Lys Arg Asp Asp
145 150 155

<210> SEQ ID NO 4
<211> LENGTH: 617
<212> TYPE: DNA
<213> ORGANISM: Lutzomyia longipalpis

<400> SEQUENCE: 4
ttttgagaaa aacatttcct tgtgagttaa atagttggta aattaaatca agagaatgtt 60
gcttcgttcc ttgtttgttc tttttctaat tttcttaaca ttctgcaacg ctgaggaaga 120
acttattgag agaaagttaa caggaaaaac gatctatatc tcaacaataa agcttccgtg 180
gttccaagct cttaatcatt gtgttaaaaa tggctacaca atggtgtcaa ttaagacatt 240
tgaagagaat aaagaactcc ttaaagaact caaaagggtg attaggacag aagatacaca 300
agtttggatt ggaggcctca aacatcatca atttgcaaac tttcgttggg taagcgatgg 360
aagccacgta gcaacagctt cagggtacac caattgggcc ccaggggagc cagctgattc 420
cttctattac gatcaatttt gcatggcgat gttgttcaga aaagacggcg ctccgtggga 480
tgatttgaat tgttgggtta agaatctttt tgtttgtgag aaacgagatg attgagaggc 540
tatttttgtt atctcaccgt tttgttgaat aaaaaagaag aagaaagaca aaaaaaaaaa 600
aaaaaaaaaa aaaaaaa 617

<210> SEQ ID NO 5
<211> LENGTH: 304
<212> TYPE: PRT
<213> ORGANISM: Lutzomyia longipalpis

<400> SEQUENCE: 5

Met Lys Leu Leu Gln Ile Ile Phe Ser Leu Phe Leu Val Phe Phe Pro

-continued 1 5 10 15

Thr Ser Asn Gly Ala Leu Thr Gly Asn Glu Ser Ala Ala Asn Ala Ala
20 25 30

Pro Leu Pro Val Val Leu Trp His Gly Met Gly Asp Ser Cys Cys Phe
35 40 45

Pro Phe Ser Leu Gly Ser Ile Lys Lys Leu Ile Glu Gln Gln Ile Pro
50 55 60

Gly Ile His Val Val Ser Leu Lys Ile Gly Lys Ser Leu Ile Glu Asp
65 70 75 80

Tyr Glu Ser Gly Phe Phe Val His Pro Asp Lys Gln Ile Gln Glu Val
85 90 95

Cys Glu Ser Leu Gln Asn Asp Leu Thr Leu Ala Asn Gly Phe Asn Ala
100 105 110

Ile Gly Phe Ser Gln Gly Ser Gln Phe Leu Arg Gly Leu Val Gln Arg
115 120 125

Cys Ser Ser Ile Gln Val Arg Asn Leu Ile Ser Ile Gly Gly Gln His
130 135 140

Gln Gly Val Phe Gly Leu Pro Tyr Cys Pro Ser Leu Ser Arg Lys Thr
145 150 155 160

Cys Glu Tyr Phe Arg Lys Leu Leu Asn Tyr Ala Ala Tyr Glu Lys Trp
165 170 175

Val Gln Lys Leu Leu Val Gln Ala Thr Tyr Trp His Asp Pro Leu Asn
180 185 190

Glu Asp Ala Tyr Arg Thr Gly Ser Thr Phe Leu Ala Asp Ile Asn Asn
195 200 205

Glu Arg Gln Ile Asn Asn Asp Tyr Ile Asn Asn Ile Arg Lys Leu Asn
210 215 220

Arg Phe Val Met Val Lys Phe Leu Asn Asp Ser Met Val Gln Pro Ile
225 230 235 240

Glu Ser Ser Phe Phe Gly Phe Tyr Ala Pro Gly Thr Asp Thr Glu Val
245 250 255

Leu Pro Leu Lys Gln Ser Lys Ile Tyr Leu Glu Asp Arg Leu Gly Leu
260 265 270

Gln Ser Val Pro Ile Asp Tyr Leu Glu Cys Gly Gly Asp His Leu Gln
275 280 285

Phe Thr Lys Glu Trp Phe Ile Lys Phe Ile Ile Pro Tyr Leu Lys Gln
290 295 300

<210> SEQ ID NO 6
<211> LENGTH: 1273
<212> TYPE: DNA
<213> ORGANISM: Lutzomyia longipalpis

<400> SEQUENCE: 6
tacttcgtac tctcagaatt tcttacaagt tccttttttct cttaactttt aaagttttat 60
ttaacaaaat tgctccattt tttcgttttc tgaatattct gttgaaattt tgattaatct 120
attttatgtg cagtttttac taaaaatccc ttatcagcaa cccggtgtct acagttttgt 180
cacgctcagt agcatcttca aggtggtaag aaaaaatgaa actcctgcaa atcatcttct 240
ctctcttcct ggtcttttttc ccgacctcaa atggggccct gaccggaaat gaaagtgcag 300
caaatgcagc tcccttgcct gtcgtcctgt ggcacgggat gggcgattct tgctgctttc 360
ccttcagttt gggaagcata aaaaaattaa ttgaacaaca aattcctggg attcatgttg 420
ttagcctgaa aattggaaag tctctcattg aggactatga aagtggattt tttgttcatc 480
cagacaagca aattcaggaa gtttgtgagt cacttcagaa cgatctaaca ctcgcaaatg 540
gattcaatgc aattggattt tctcagggta gtcagttcct gcgaggtctt gtgcaacgat 600
gttcttctat acaagtaagg aatctcattt ccattggagg acagcatcaa ggggtttttg 660
gtctgcccta ttgtccttcg ttgagcagaa agacttgcga atactttaga aagctcctga 720
attatgcagc ttatgaaaaa tgggtacaga aactcctagt tcaagccacc tactggcatg 780
atcctctaaa tgaggatgca tatcggactg gaagcacttt ccttgctgat ataaataatg 840
agagacaaat caataatgac tatattaata atattcggaa gctaaatcgt tttgtgatgg 900
taaagttcct caacgacagc atggttcagc caattgaatc tagtttcttt ggattctacg 960
ctccaggaac tgatacagaa gttctcccat taaaacaaag caagatttat ttggaagatc 1020
gtttgggact tcaatcagta ccgatagatt atctagaatg cggaggagat catttgcaat 1080
ttacaaaaga atggttcata aagtttatca taccctatct gaagcaataa gagctgcaat 1140
gtaattgatt aaaaaatgtt aaccatttca ggatgattgg gtgacccctt aaaaatataa 1200
atgaaaaaat atacaaaaga aataaatttt tatattgatc ccacaaaaaa aaaaaaaaaa 1260
aaaaaaaaaa aaa 1273

<210> SEQ ID NO 7
<211> LENGTH: 102
<212> TYPE: PRT
<213> ORGANISM: Lutzomyia longipalpis

<400> SEQUENCE: 7

Met Arg Asn Phe Ala Val Val Ser Leu Ala Val Ala Val Leu Leu Phe
1 5 10 15

Cys Ala Trp Pro Ile Asn Ala Glu Asp Asn Glu Glu Val Gly Lys Ala
20 25 30

Arg Glu Lys Arg Gly Leu Lys Asp Ala Met Glu His Phe Lys Asn Gly
35 40 45

Phe Lys Glu Leu Thr Lys Asp Phe Lys Leu Pro Ser Leu Pro Ser Leu
50 55 60

Pro Gly Phe Gly Lys Lys Pro Glu Ser Gly Ser Ser Glu Asp Ser Gly
65 70 75 80

Asp Lys Thr Glu Asp Thr Ser Gly Ser Lys Asp Asp Gln Ser Lys Asp
85 90 95

Asn Thr Val Glu Glu Ser
100

<210> SEQ ID NO 8
<211> LENGTH: 466
<212> TYPE: DNA
<213> ORGANISM: Lutzomyia longipalpis

<400> SEQUENCE: 8
ggatcggcca ttatggccgg ggcagttaat cgccacaatt taataaaatg aggaactttg 60
ctgtagtcag tttagccgtt gctgtcctgc tcttctgtgc atggcctata aatgcggaag 120
ataatgaaga agttggaaag gcgagagaaa aaagaggctt aaaagacgca atggaacact 180
tcaaaaatgg atttaaggag ctgacaaagg actttaaact tccaagcctt ccaagtcttc 240
ctggatttgg taaaaagcct gaatctggaa gttctgaaga ttctggagat aaaactgagg 300
ataccagtgg atctaaggac gaccaatcaa aggataatac ggtcgaagaa tcttaagaaa 360
ggcgcaaata gctattttca aagtggcgaa tgtttctttc tttatctgaa ataaatattt 420

```
ttaaaccttt cgaaaccaaa aaaaaaaaaa aaaaaaaaaa aaaaaa                466


<210> SEQ ID NO 9
<211> LENGTH: 247
<212> TYPE: PRT
<213> ORGANISM: Lutzomyia longipalpis

<400> SEQUENCE: 9

Met Asn Phe Leu Leu Lys Ile Phe Ser Leu Leu Cys Leu Cys Gly Leu
1               5                   10                  15

Gly Tyr Ser Trp Gln Asp Val Arg Asn Ala Asp Gln Thr Leu Trp Ala
            20                  25                  30

Tyr Arg Ser Cys Gln Lys Asn Pro Glu Asp Lys Asp His Val Pro Gln
        35                  40                  45

Trp Arg Lys Phe Glu Leu Pro Asp Asp Glu Lys Thr His Cys Tyr Val
    50                  55                  60

Lys Cys Val Trp Thr Arg Leu Gly Ala Tyr Asn Glu Asn Glu Asn Val
65                  70                  75                  80

Phe Lys Ile Asp Val Ile Thr Lys Gln Phe Asn Glu Arg Gly Leu Glu
                85                  90                  95

Val Pro Ala Gly Leu Asp Gln Glu Leu Gly Gly Ser Thr Asp Gly Thr
            100                 105                 110

Cys Lys Ala Val Tyr Asp Lys Ser Met Lys Phe Phe Lys Ser His Phe
        115                 120                 125

Met Asp Phe Arg Asn Ala Tyr Tyr Ala Thr Tyr Asp Gly Ser Asp Glu
    130                 135                 140

Trp Phe Ser Lys Asn Pro Asp Val Lys Pro Lys Gly Thr Lys Val Ser
145                 150                 155                 160

Glu Tyr Cys Lys Asn Lys Asp Asp Gly Asp Cys Lys His Ser Cys Ser
                165                 170                 175

Met Tyr Tyr Tyr Arg Leu Ile Asp Glu Asp Asn Leu Val Ile Pro Phe
            180                 185                 190

Ser Asn Leu Pro Asp Tyr Pro Glu Asp Lys Leu Glu Glu Cys Arg Asn
        195                 200                 205

Glu Ala Lys Ser Ala Asn Glu Cys Lys Ser Ser Val Ile Tyr Gln Cys
    210                 215                 220

Leu Glu Asn Ala Asp Lys Ser Ala Leu Asp Ala Ser Leu Asn Ile Leu
225                 230                 235                 240

Asp Glu Phe Ser Gly Arg Tyr
                245


<210> SEQ ID NO 10
<211> LENGTH: 955
<212> TYPE: DNA
<213> ORGANISM: Lutzomyia longipalpis

<400> SEQUENCE: 10

acttaaagat ttttgtttaa gcaaaatgaa cttcttgttg aaaattttct ctttgctctg      60

tctctgtgga ctggggtatt catggcagga tgtgagaaat gccgatcaaa ccctctgggc     120

gtatagatcg tgccaaaaga atcctgaaga taaggatcac gtacctcaat ggaggaagtt     180

cgaattaccc gacgatgaaa agactcattg ctacgtcaag tgcgtatgga cgcgtttggg     240

agcttacaat gaaaatgaaa atgttttcaa aattgatgtc attactaagc aatttaatga     300

acgtggccta gaagttccgg ctggacttga tcaagaattg ggtggttcta cagatggaac     360
```

-continued

```
ttgcaaagca gtttacgata aatccatgaa gttcttcaaa tctcatttta tggactttag    420

gaatgcttac tacgcaactt atgacggttc tgatgaatgg tttagcaaga accctgatgt    480

aaaaccgaaa ggaacaaaag tttccgaata ctgcaaaaat aaagatgatg gagattgcaa    540

acattcctgc agtatgtact actaccgctt aatcgatgaa gacaacttag ttattccgtt    600

cagcaactta cctgactatc ccgaagataa gctcgaggaa tgcaggaatg aagccaagtc    660

cgcaaatgag tgcaaatcat ctgttatcta tcagtgtttg gaaaatgcgg ataagtcagc    720

tttagacgcg tctttgaata tactcgatga gttttctgga agatattaaa acaaactgga    780

taaaaaactt aggccaacct atgattcgaa cttacgattt tgaacttgaa attcatgtgc    840

tttaacctat tgtcccacta ggaagaaaaa tccatatttg gtgatgttaa actatttttg    900

aacctcttca aaataaacaa ttttcaaaaa aaaaaaaaaa aaaaaaaaaa aaaaa         955
```

```
<210> SEQ ID NO 11
<211> LENGTH: 325
<212> TYPE: PRT
<213> ORGANISM: Lutzomyia longipalpis

<400> SEQUENCE: 11

Met Phe Leu Lys Trp Val Val Cys Ala Phe Ala Thr Val Phe Leu Val
1               5                   10                  15

Gly Val Ser Gln Ala Ala Pro Pro Gly Val Glu Trp Tyr His Phe Gly
            20                  25                  30

Leu Ile Ala Asp Met Asp Lys Lys Ser Ile Ala Ser Asp Lys Thr Thr
        35                  40                  45

Phe Asn Ser Val Leu Lys Ile Asp Glu Leu Arg His Asn Thr Lys Thr
    50                  55                  60

Asp Gln Tyr Ile Tyr Val Arg Ser Arg Val Lys Lys Pro Val Ser Thr
65                  70                  75                  80

Arg Tyr Gly Phe Lys Gly Arg Gly Ala Glu Leu Ser Glu Ile Val Val
                85                  90                  95

Phe Asn Asn Lys Leu Tyr Thr Val Asp Asp Lys Ser Gly Ile Thr Phe
            100                 105                 110

Arg Ile Thr Lys Asp Gly Lys Leu Phe Pro Trp Val Ile Leu Ala Asp
        115                 120                 125

Ala Asp Gly Gln Arg Pro Asp Gly Phe Lys Gly Glu Trp Ala Thr Ile
    130                 135                 140

Lys Asp Asp Thr Ile Tyr Val Gly Ser Thr Gly Met Leu Lys Phe Thr
145                 150                 155                 160

Ser Ser Leu Trp Val Lys Lys Ile Thr Lys Asp Gly Val Val Thr Ser
                165                 170                 175

His Asp Trp Thr Asp Lys Tyr Arg Lys Ile Leu Lys Ala Leu Asn Met
            180                 185                 190

Pro Asn Gly Phe Val Trp His Glu Ala Val Thr Trp Ser Pro Phe Arg
        195                 200                 205

Lys Gln Trp Val Phe Met Pro Arg Lys Cys Ser Arg His Pro Phe Ser
    210                 215                 220

Gln Glu Leu Glu Glu Arg Thr Gly Cys Asn Lys Ile Val Thr Ala Asp
225                 230                 235                 240

Glu Asn Phe Asn Asp Ile Gln Val Ile His Ile Gln Asp Gln Pro Tyr
                245                 250                 255

Asn Leu Ala Ser Gly Phe Ser Ser Phe Arg Phe Ile Pro Gly Thr Lys
            260                 265                 270
```

```
Asn Glu Arg Leu Leu Ala Leu Arg Thr Val Glu Gln Glu Asp Gln Val
        275                 280                 285

Lys Thr Trp Ala Val Val Met Asp Met Lys Gly Thr Val Leu Met Tyr
    290                 295                 300

Glu Lys Glu Leu Tyr Asp Glu Lys Phe Glu Gly Leu Ala Phe Phe Gly
305                 310                 315                 320

Gly Ile Lys Lys Asn
                325


<210> SEQ ID NO 12
<211> LENGTH: 1071
<212> TYPE: DNA
<213> ORGANISM: Lutzomyia longipalpis

<400> SEQUENCE: 12

aaagagaagt agtgagaatg tttcttaagt gggttgtttg tgcttttgcg actgtcttcc     60

ttgttggggt gagtcaggca gccccaccgg gggttgaatg gtatcacttt ggtctgattg    120

ctgatatgga caaaaaatcc atcgcgagtg acaaaaccac ctttaacagc gtcctaaaga    180

tcgatgaatt gcgccacaac acaaaaacgg atcaatacat ttatgtgcgt agtcgagtga    240

agaagcccgt ttccacgagg tatgggttca aaggacgcgg tgcggaattg tcggaaattg    300

ttgtcttcaa caataaactt tacacagttg atgataaatc tggaattacg ttccgcataa    360

cgaaagacgg aaaactcttc ccgtgggtta ttctcgcaga tgccgatgga cagcgacccg    420

atggctttaa gggtgaatgg gctacaatta aggatgatac aatctatgtt ggatctacgg    480

ggatgctcaa gttcacttca tccctttggg tgaagaagat cacgaaagat ggcgttgtta    540

cgagtcacga ttggactgat aaataccgaa agattctcaa agctctaaac atgccaaatg    600

gttttgtctg gcatgaggct gttacgtggt ctccattcag gaagcaatgg gtcttcatgc    660

cgagaaagtg ctcaaggcat cccttctcac aggaactcga agaacgcaca gggtgcaata    720

aaatagtgac ggcagatgag aatttcaacg acattcaagt tattcacatt caagatcagc    780

catataattt agcttctggt ttctcttcct tccgctttat tcctggtacg aaaaatgaaa    840

gacttctcgc cttgaggaca gtagagcagg aagatcaggt taaaacttgg gctgtggtca    900

tggatatgaa aggaacagtt ctgatgtacg aaaaggaact ttatgacgaa aaattcgaag    960

gtttagcatt ctttggtggt attaaaaaga attaatttgt tccagaagct tttagatgaa   1020

ataataaatt ttatttcatt ttaaaaaaaa aaaaaaaaaa aaaaaaaaaa a            1071


<210> SEQ ID NO 13
<211> LENGTH: 160
<212> TYPE: PRT
<213> ORGANISM: Lutzomyia longipalpis

<400> SEQUENCE: 13

Met Ala Leu Lys Phe Leu Pro Val Leu Leu Leu Ser Cys Phe Ala Met
1               5                   10                  15

Ser Thr Ala Leu Gln Val Thr Glu Lys Glu Leu Ser Asp Gly Lys Lys
            20                  25                  30

Ile Phe Ile Ser Lys Val Glu Leu Asn Trp Phe Glu Ala Leu Asp Phe
        35                  40                  45

Cys Ile His Arg Gly Leu Thr Leu Leu Ser Ile Lys Ser Ala Lys Glu
    50                  55                  60

Asn Val Asp Val Thr Lys Ala Ile Arg Ala Glu Leu Asn Phe Asp Ser
65                  70                  75                  80
```

```
Lys Lys Leu Ala His Val Trp Thr Gly Gly Ile Arg His Ser Gln Asp
                85                  90                  95

Lys Tyr Phe Arg Trp Ile Asn Asp Gly Thr Lys Val Val Lys Arg Val
            100                 105                 110

Tyr Thr Asn Trp Phe Thr Gly Glu Pro Asn Asn Gly Tyr Trp Lys Asp
        115                 120                 125

Glu Phe Cys Leu Glu Ile Tyr Tyr Lys Thr Glu Glu Gly Lys Trp Asn
    130                 135                 140

Asp Asp Lys Cys His Val Lys His His Phe Val Cys Gln Glu Lys Lys
145                 150                 155                 160


<210> SEQ ID NO 14
<211> LENGTH: 648
<212> TYPE: DNA
<213> ORGANISM: Lutzomyia longipalpis

<400> SEQUENCE: 14

cgcggccgcg tcgaccgaca gaaggggtag tttgtagaga actttgagtt ctaaaggaaa      60

ttctcaagaa gaaaatattc aaaagtaaag aatggcgttg aagtttcttc cggttctcct     120

tctaagctgc ttcgcaatga gcacggcact acaagttact gagaaggaac tttctgatgg     180

gaaaaagatc ttcatctcca aagttgagct aaactggttc gaagctcttg atttctgtat     240

ccatcgtggt cttacgttgc tctcaattaa atccgccaag gaaaatgtag acgtaacaaa     300

agcaattcgg gctgaattga attttgattc aaagaaattg gctcatgtgt ggactggagg     360

tattcgccat agtcaagata agtatttccg ttggataaat gatggaacta aagttgttaa     420

acgagtctac accaattggt tcactggaga accaaataat ggttactgga aggatgaatt     480

ttgtctggaa atttactata aaaccgaaga agggaagtgg aatgatgata aatgtcacgt     540

gaagcatcat tttgtatgtc aagaaaagaa ataaattgat tgattttgtt tgctgatttg     600

cagttcagaa ttgaaaagcc aaaaaaaaaa aaaaaaaaaa aaaaaaaa                  648


<210> SEQ ID NO 15
<211> LENGTH: 301
<212> TYPE: PRT
<213> ORGANISM: Lutzomyia longipalpis

<400> SEQUENCE: 15

Met Asn Ser Ile Asn Phe Leu Ser Ile Val Gly Leu Ile Ser Phe Gly
1               5                   10                  15

Phe Ile Val Ala Val Lys Cys Asp Gly Asp Glu Tyr Phe Ile Gly Lys
            20                  25                  30

Tyr Lys Glu Lys Asp Glu Thr Leu Phe Phe Ala Ser Tyr Gly Leu Lys
        35                  40                  45

Arg Asp Pro Cys Gln Ile Val Leu Gly Tyr Lys Cys Ser Asn Asn Gln
    50                  55                  60

Thr His Phe Val Leu Asn Phe Lys Thr Asn Lys Lys Ser Cys Ile Ser
65                  70                  75                  80

Ala Ile Lys Leu Thr Ser Tyr Pro Lys Ile Asn Gln Asn Ser Asp Leu
                85                  90                  95

Thr Lys Asn Leu Tyr Cys Gln Thr Gly Gly Ile Gly Thr Asp Asn Cys
            100                 105                 110

Lys Leu Val Phe Lys Lys Arg Lys Arg Gln Ile Ala Ala Asn Ile Glu
        115                 120                 125

Ile Tyr Gly Ile Pro Ala Lys Lys Cys Ser Phe Lys Asp Arg Tyr Ile
    130                 135                 140
```

```
Gly Ala Asp Pro Leu His Val Asp Ser Tyr Gly Leu Pro Tyr Gln Phe
145                 150                 155                 160

Asp Gln Glu His Gly Trp Asn Val Glu Arg Tyr Asn Ile Phe Lys Asp
                165                 170                 175

Thr Arg Phe Ser Thr Glu Val Phe Tyr His Lys Asn Gly Leu Phe Asn
            180                 185                 190

Thr Gln Ile Thr Tyr Leu Ala Glu Glu Asp Ser Phe Ser Glu Ala Arg
        195                 200                 205

Glu Ile Thr Ala Lys Asp Ile Lys Lys Lys Phe Ser Ile Ile Leu Pro
    210                 215                 220

Asn Glu Glu Tyr Lys Arg Ile Ser Phe Leu Asp Val Tyr Trp Phe Gln
225                 230                 235                 240

Glu Thr Met Arg Lys Lys Pro Lys Tyr Pro Tyr Ile His Tyr Asn Gly
                245                 250                 255

Glu Cys Ser Asn Glu Asn Lys Thr Cys Glu Leu Val Phe Asp Thr Asp
            260                 265                 270

Glu Leu Met Thr Tyr Ala Leu Val Lys Val Phe Thr Asn Pro Glu Ser
        275                 280                 285

Asp Gly Ser Arg Leu Lys Glu Glu Asp Leu Gly Arg Gly
    290                 295                 300
```

<210> SEQ ID NO 16
<211> LENGTH: 1021
<212> TYPE: DNA
<213> ORGANISM: Lutzomyia longipalpis

<400> SEQUENCE: 16

```
cttctttgga tttattgagt gattaacagg aaattagctg aagaaatgaa ttcgattaat     60

ttcctatcaa tagttggttt aatcagtttt ggattcattg ttgcagtaaa gtgtgatggt    120

gatgaatatt tcattggaaa atacaaagaa aaagatgaga cactgttttt tgcaagctac    180

ggcctaaaga gggatccttg ccaaattgtc ttaggctaca aatgctcaaa caatcaaacc    240

cactttgtgc ttaattttaa aaccaataag aaatcctgca tatcagcaat taagctgact    300

tcttacccaa aaatcaatca aaactcggat ttaactaaaa atctctactg ccaaactgga    360

ggaataggaa cagataactg caaacttgtc ttcaagaaac gtaaaagaca aatagcagct    420

aatattgaaa tctacggcat tccagcgaag aaatgttcct tcaaggatcg ttacattgga    480

gctgatccac tccacgtcga ttcctatggg cttccgtatc agtttgatca ggaacatgga    540

tggaatgtgg aacgatataa cattttcaaa gacacaagat tttccacaga agttttctac    600

cacaaaaatg gtttatttaa cacccaaata acttatttgg ctgaagaaga ttccttctct    660

gaagctcgag agattactgc gaaggatatt aagaagaagt tttcaattat tttgcccaat    720

gaagagtata agaggattag tttcttggac gtttattggt tccaggagac tatgcgaaaa    780

aagcctaaat atccctacat tcactacaat ggagaatgca gcaatgagaa taaaacttgt    840

gaacttgtct ttgacaccga tgaactaatg acctacgccc ttgttaaagt ctttactaat    900

cctgagagtg atggatctag gctcaaagaa gaggatttgg gaagaggata aatcttctta    960

ataaaaaaaa gttctgtaag aaaatattgt tcaataaatt aaaaaaaaaa aaaaaaaaaa   1020

a                                                                   1021
```

<210> SEQ ID NO 17
<211> LENGTH: 161
<212> TYPE: PRT

<213> ORGANISM: Lutzomyia longipalpis

<400> SEQUENCE: 17

Met Ala Phe Ser Asn Thr Leu Phe Val Leu Phe Val Ser Phe Leu Thr
1 5 10 15

Phe Cys Gly Ala Asp Gln Thr Leu Ile Glu Lys Glu Leu Thr Gly Arg
20 25 30

Thr Val Tyr Ile Ser Lys Ile Lys Leu Asn Trp Asn Asp Ala Phe Asp
35 40 45

Tyr Cys Ile Arg Asn Gly Leu Thr Phe Ala Lys Ile Lys Ser Ala Glu
50 55 60

Glu Asn Thr Glu Leu Ser Glu Lys Leu Lys Thr Val Ile Arg Thr Glu
65 70 75 80

Glu Phe Gln Val Trp Ile Gly Gly Ile Glu His His Gln Asp Ser Ser
85 90 95

Phe Arg Trp Val Ser Asp Ser Gln Pro Ile Thr Asn Lys Leu Gly Tyr
100 105 110

Lys Tyr Thr Asn Trp Asn Thr Gly Glu Pro Thr Asn Tyr Gln Asn Asn
115 120 125

Glu Tyr Cys Leu Glu Ile Leu Phe Arg Lys Glu Asp Gly Lys Trp Asn
130 135 140

Asp Phe Pro Cys Ser Ala Arg His His Phe Val Cys Glu Lys Arg Thr
145 150 155 160

Lys

<210> SEQ ID NO 18
<211> LENGTH: 586
<212> TYPE: DNA
<213> ORGANISM: Lutzomyia longipalpis

<400> SEQUENCE: 18
aatagatctt caaaacgtct aagaatggct ttcagcaaca ctttatttgt tctttttgtg 60
agttttttaa cgttttgtgg cgctgatcag acacttattg agaaggaatt aaccggaaga 120
actgtttata tctccaaaat taagctaaat tggaacgatg ccttcgatta ctgcatccgc 180
aatggcctca cctttgctaa gattaaatca gctgaagaaa acaccgaact gagtgagaaa 240
ctcaagacag tcattcgtac ggaggagttt caagtttgga ttggaggcat tgaacatcat 300
caagacagtt ccttccgctg ggtaagcgac tcccaaccaa taaccaacaa attgggctac 360
aaatacacaa actggaatac cggagagccc acaaattacc aaaacaacga atattgcttg 420
gaaatattat tccggaagga agatggaaaa tggaatgatt ttccctgcag tgcaagacat 480
cattttgttt gtgaaaaaag aacaaaataa aatgaagaaa atgtgatttt cctttggttg 540
aagaataaaa ttctgttgaa aaaaaaaaaa aaaaaaaaaa aaaaaa 586

<210> SEQ ID NO 19
<211> LENGTH: 105
<212> TYPE: PRT
<213> ORGANISM: Lutzomyia longipalpis

<400> SEQUENCE: 19

Met Gln Asn Phe Leu Leu Val Ser Leu Ala Leu Ala Ala Leu Met Leu
1 5 10 15

Cys Ala Glu Ala Lys Pro Tyr Asp Phe Pro Leu Tyr Gln Asp Leu Ile
20 25 30

Gln Gly Val Ile Gln Arg Glu Ser Gln Ala Glu Arg Glu Lys Arg Ser

```
        35                  40                  45

Pro Asn Glu Asp Tyr Glu Lys Gln Phe Gly Asp Ile Val Asp Gln Ile
    50                  55                  60

Lys Glu Ile Ser Phe Asn Val Met Lys Met Pro His Phe Gly Ser Ser
65                  70                  75                  80

Asp Asp Asn Arg Asp Asp Gly Glu Tyr Val Asp His His Tyr Gly Asp
                85                  90                  95

Glu Asp Asp Arg Asp Tyr Asp His Tyr
            100                 105
```

<210> SEQ ID NO 20
<211> LENGTH: 457
<212> TYPE: DNA
<213> ORGANISM: Lutzomyia longipalpis

<400> SEQUENCE: 20

```
atttagtttg tgtttaacaa aacaagaatg cagaacttcc ttttagtttc cttggcttta      60

gctgccttaa tgctatgtgc cgaagcaaag ccgtacgatt ttccgcttta tcaggactta     120

attcagggcg ttattcagcg cgaaagtcaa gctgagaggg agaagagaag ccccaatgag     180

gactatgaga agcaatttgg ggatattgtt gatcaaatta aggaaattag tttcaatgtc     240

atgaaaatgc ccccattttgg aagctctgat gataatcgtg atgatggcga gtacgttgat     300

catcattatg gtgacgaaga tgatcgtgat tatgatcatt actaaatact acttgctcct     360

gctgaatgac ttgaaggaat catttttttg caaaaatatc catcaaatta ttgaattaat     420

aaagttgcaa aaaaaaaaaa aaaaaaaaaa aaaaaaa                              457
```

<210> SEQ ID NO 21
<211> LENGTH: 157
<212> TYPE: PRT
<213> ORGANISM: Lutzomyia longipalpis

<400> SEQUENCE: 21

```
Met Lys Phe Tyr Ile Phe Gly Val Phe Leu Val Ser Phe Leu Ala Leu
1               5                   10                  15

Cys Asn Ala Glu Asp Tyr Asp Lys Val Lys Leu Thr Gly Arg Thr Val
            20                  25                  30

Tyr Ile Ser Arg Ser Lys Ala Pro Trp Phe Thr Ala Leu Asp Asn Cys
        35                  40                  45

Asn Arg Arg Phe Thr Phe Ala Met Ile Lys Ser Gln Lys Glu Asn Glu
    50                  55                  60

Glu Leu Thr Asn Ala Leu Leu Ser Val Ile Lys Ser Asp Glu Glu Asn
65                  70                  75                  80

Val Trp Ile Gly Gly Leu Arg His Asp Leu Asp Asp Tyr Phe Arg Trp
                85                  90                  95

Ile Ser Phe Gly Thr Ala Leu Ser Lys Thr Ser Tyr Thr Asn Trp Ala
            100                 105                 110

Pro Lys Glu Pro Thr Gly Arg Pro His Arg Thr Gln Asn Asp Glu Phe
        115                 120                 125

Cys Met Gln Met Ser Phe Lys Asp Gly Gly Lys Trp Ser Asp Asn Thr
    130                 135                 140

Cys Trp Arg Lys Arg Leu Tyr Val Cys Glu Lys Arg Asp
145                 150                 155
```

<210> SEQ ID NO 22
<211> LENGTH: 596

<212> TYPE: DNA
<213> ORGANISM: Lutzomyia longipalpis

<400> SEQUENCE: 22
gtttaaggaa tttctttcat ctcagtcttc gattttcttt aaacaaataa tgaagtttta 60
tatttttgga gttttcctgg tgagctttct tgcattatgc aatgctgagg attatgataa 120
agtaaaactt actggaagaa ctgtttacat ctccagatca aaggctccgt ggttcacagc 180
tttagacaat tgtaatcgtt tacgcttcac cttcgccatg atcaagtctc agaaggagaa 240
tgaagagcta acaaatgcgc ttttaagtgt aattaaatct gacgaagaaa atgtttggat 300
tggaggtctt aggcacgatc tggatgacta cttccgttgg attagttttg gaactgcatt 360
gtcaaagact tcgtacacca attgggcccc aaaggaaccc acaggaaggc cccatagaac 420
tcaaaatgat gaattctgca tgcaaatgtc tttcaaagat ggtggcaaat ggagtgataa 480
cacctgttgg cgtaaacgtt tgtacgtttg tgaaaagcgt gattaaataa aggaacactg 540
ccaatgaata ttgggcaatt tgagagaaat taaattaaaa aaaaaaaaaa aaaaaa 596

<210> SEQ ID NO 23
<211> LENGTH: 412
<212> TYPE: PRT
<213> ORGANISM: Lutzomyia longipalpis

<400> SEQUENCE: 23

```
Met Arg Phe Phe Phe Val Phe Leu Ala Ile Val Leu Phe Gln Gly Ile
1               5                   10                  15

His Gly Ala Tyr Val Glu Ile Gly Tyr Ser Leu Arg Asn Ile Thr Phe
            20                  25                  30

Asp Gly Leu Asp Thr Asp Asp Tyr Asn Pro Lys Phe Asn Ile Pro Thr
        35                  40                  45

Gly Leu Ala Val Asp Pro Glu Gly Tyr Arg Leu Phe Ile Ala Ile Pro
    50                  55                  60

Arg Arg Lys Pro Lys Val Pro Tyr Thr Val Ala Glu Leu Asn Met Val
65                  70                  75                  80

Met Asn Pro Gly Phe Pro Val Glu Arg Ala Pro Ser Phe Glu Lys Phe
                85                  90                  95

Lys Lys Phe Asn Gly Glu Gly Lys Lys Asp Leu Val Asn Val Tyr Gln
            100                 105                 110

Pro Val Ile Asp Asp Cys Arg Arg Leu Trp Val Leu Asp Ile Gly Lys
        115                 120                 125

Val Glu Tyr Thr Gly Gly Asp Ala Asp Gln Tyr Pro Lys Gly Lys Pro
    130                 135                 140

Thr Leu Ile Ala Tyr Asp Leu Lys Lys Asp His Thr Pro Glu Ile His
145                 150                 155                 160

Arg Phe Glu Ile Pro Asp Asp Leu Tyr Ser Ser Gln Val Glu Phe Gly
                165                 170                 175

Gly Phe Ala Val Asp Val Val Asn Thr Lys Gly Asp Cys Thr Glu Ser
            180                 185                 190

Phe Val Tyr Leu Thr Asn Phe Lys Asp Asn Ser Leu Ile Val Tyr Asp
        195                 200                 205

Glu Thr Gln Lys Lys Ala Trp Lys Phe Thr Asp Lys Thr Phe Glu Ala
    210                 215                 220

Asp Lys Glu Ser Thr Phe Ser Tyr Ser Gly Glu Glu Gln Met Lys Tyr
225                 230                 235                 240

Lys Val Gly Leu Phe Gly Ile Ala Leu Gly Asp Arg Asp Glu Met Gly
```

-continued

```
                245                 250                 255

His Arg Pro Ala Cys Tyr Ile Ala Gly Ser Ser Thr Lys Val Tyr Ser
            260                 265                 270

Val Asn Thr Lys Glu Leu Lys Thr Glu Asn Gly Gln Leu Asn Pro Gln
        275                 280                 285

Leu His Gly Asp Arg Gly Lys Tyr Thr Asp Ala Ile Ala Leu Ala Tyr
    290                 295                 300

Asp Pro Glu His Lys Val Leu Tyr Phe Ala Glu Ser Asp Ser Arg Gln
305                 310                 315                 320

Val Ser Cys Trp Asn Val Asn Met Glu Leu Lys Pro Asp Asn Thr Asp
                325                 330                 335

Val Ile Phe Ser Ser Ala Arg Phe Thr Phe Gly Thr Asp Ile Leu Val
            340                 345                 350

Asp Ser Lys Gly Met Leu Trp Ile Met Ala Asn Gly His Pro Pro Val
        355                 360                 365

Glu Asp Gln Glu Lys Ile Trp Lys Met Arg Phe Val Asn Arg Lys Ile
    370                 375                 380

Arg Ile Met Lys Val Asp Thr Glu Arg Val Phe Lys Tyr Ser Arg Cys
385                 390                 395                 400

Asn Pro Asn Tyr Lys Pro Pro Lys Glu Ile Glu Val
                405                 410


<210> SEQ ID NO 24
<211> LENGTH: 1409
<212> TYPE: DNA
<213> ORGANISM: Lutzomyia longipalpis

<400> SEQUENCE: 24

agtcagtgtt aatgaagaaa ttgcaattat gaggttcttc tttgttttcc ttgccatcgt      60

ccttttttcaa gggatccacg gagcttatgt ggaaatagga tattctctga gaaatattac    120

attcgatgga ttggatacag atgactacaa tccaaagttc aacattccaa cgggtttggc    180

agttgatccc gaaggatata ggctcttcat agccatccca aggagaaagc caaaggttcc    240

ctacactgtg gctgaactga atatggtcat gaatcccgga tttcccgtcg agagagctcc    300

gagctttgag aaattcaaaa aattcaatgg cgagggcaaa aaggatcttg ttaatgtgta    360

tcagccagtc attgatgatt gtcgtcgtct ttgggtgctt gacattggga aggtggaata    420

caccggtggt gatgctgatc aatatcccaa aggaaagcct accctaattg cctacgacct    480

caagaaggat catactccgg aaattcatcg atttgaaatt ccagacgatc tctatagctc    540

acaagttgaa tttggtggat ttgccgttga tgttgttaac acgaaaggag actgtacgga    600

gtcatttgtc tacctgacca atttcaagga taactctcta attgtctacg atgagacaca    660

aaagaaagct tggaaattca cagataaaac atttgaagct gataaggaat ccacgttctc    720

ctactcggga gaggaacaaa tgaagtacaa agtcggtctt tttgggatag ctctgggtga    780

tagggatgaa atggggcatc gtcctgcctg ctacatcgct gggagtagca ccaaagtcta    840

cagtgttaac actaaagaac tcaaaacaga gaatggtcag ttaaatcctc agcttcacgg    900

tgatcgtgga aagtacacag atgcaattgc cctagcctac gatcctgagc ataaagtcct    960

ctactttgct gaatccgaca gcaggcaggt gtcctgttgg aatgtaaata tggagctaaa   1020

accagacaat acggatgtga tcttctctag tgcccgtttt acttttggaa cggatatttt   1080

ggttgatagc aagggaatgc tgtggataat ggctaatgga catccaccag tagaggatca   1140

agagaagatt tggaagatga gattcgtaaa ccggaagatc cgtattatga aagtggatac   1200
```

```
ggaacgtgtt ttcaaatatt cacgctgcaa tccaaattat aagcccccaa aggaaattga   1260

agtttgagac acaggaaaaa gctcaatttt caacaagaat ttgatcttaa tctgaatacc   1320

ctaaagtctg tcaaagaatt tcatattatt tgaaaaccaa taaattgatt aattttccga   1380

aaaaaaaaaa aaaaaaaaaa aaaaaaaaa                                      1409
```

<210> SEQ ID NO 25
<211> LENGTH: 295
<212> TYPE: PRT
<213> ORGANISM: Lutzomyia longipalpis

<400> SEQUENCE: 25

```
Met Ile Lys Glu Val Phe Ser Leu Ala Leu Leu Val Ala Leu Ala Gln
1               5                   10                  15

Cys Ala Asn Glu Ile Pro Ile Asn Arg Gln Gly Lys Asp Tyr Pro Val
            20                  25                  30

Pro Ile Ile Asp Pro Asn Lys Ser Ser Ser Asp Asp Tyr Phe Asp Asp
        35                  40                  45

Arg Phe Tyr Pro Asp Ile Asp Asp Glu Gly Ile Ala Glu Ala Pro Lys
    50                  55                  60

Asp Asn Arg Gly Lys Ser Arg Gly Gly Gly Ala Ala Gly Ala Arg Glu
65                  70                  75                  80

Gly Arg Leu Gly Thr Asn Gly Ala Lys Pro Gly Gln Gly Gly Thr Arg
                85                  90                  95

Pro Gly Gln Gly Gly Thr Arg Pro Gly Gln Gly Gly Thr Arg Pro Gly
            100                 105                 110

Gln Gly Gly Thr Arg Pro Gly Gln Gly Gly Thr Arg Pro Gly Gln Gly
        115                 120                 125

Arg Thr Lys Pro Ala Gln Gly Thr Thr Arg Pro Ala Gln Gly Thr Arg
    130                 135                 140

Asn Pro Gly Ser Val Gly Thr Lys Glu Ala Gln Asp Ala Ser Lys Gln
145                 150                 155                 160

Gly Gln Gly Lys Arg Arg Pro Gly Gln Val Gly Gly Lys Arg Pro Gly
                165                 170                 175

Gln Ala Asn Ala Pro Asn Ala Gly Thr Arg Lys Gln Gln Lys Gly Ser
            180                 185                 190

Arg Gly Val Gly Arg Pro Asp Leu Ser Arg Tyr Lys Asp Ala Pro Ala
        195                 200                 205

Lys Phe Val Phe Lys Ser Pro Asp Phe Ser Gly Glu Gly Lys Thr Pro
    210                 215                 220

Thr Val Asn Tyr Phe Arg Thr Lys Lys Lys Glu His Ile Val Thr Arg
225                 230                 235                 240

Gly Ser Pro Asn Asp Glu Phe Val Leu Glu Ile Leu Asp Gly Asp Pro
                245                 250                 255

Thr Gly Leu Gly Leu Lys Ser Glu Thr Ile Gly Lys Asp Thr Arg Leu
            260                 265                 270

Val Leu Glu Asn Pro Asn Gly Asn Ser Ile Val Ala Arg Val Lys Ile
        275                 280                 285

Tyr Lys Asn Gly Tyr Ser Gly
    290                 295
```

<210> SEQ ID NO 26
<211> LENGTH: 989
<212> TYPE: DNA
<213> ORGANISM: Lutzomyia longipalpis

<400> SEQUENCE: 26
actaaagcgt ctcaccgaaa tcagggaaaa tgattaagga agttttctct ctggctctac 60
ttgtggcctt ggcacagtgt gctaatgaaa tccctattaa tcgtcagggg aaagattatc 120
cagttccgat cattgatcca aataaatcat cttcggatga ttatttcgat gatcgcttct 180
accctgatat tgatgatgag ggcatagctg aggctcctaa ggataatagg ggaaaatccc 240
gtggtggtgg tgcggctggc gcaagagaag gtaggttagg tacgaatggg gctaaaccgg 300
gtcagggtgg aactagacca ggacagggtg gaactaggcc aggacagggt ggaactaggc 360
caggtcaggg tggaactagg ccaggtcagg gtggaactag acctgggcaa ggtagaacta 420
agcctgctca gggaactact aggccagctc agggaactag aaatccagga tcggttggta 480
cgaaagaagc ccaggatgcg tcaaaacaag gtcaaggtaa aagaaggcca gggcaagttg 540
gtggtaaaag accaggacaa gcaaatgctc ctaatgcagg cactagaaag caacagaaag 600
gcagtagagg cgttggaagg cctgatctat cgcgctacaa agatgcccct gctaaattcg 660
ttttcaaatc tcccgatttc agtggagaag gcaaaactcc aactgtaaat tactttagaa 720
cgaagaagaa ggagcacatt gtgacccgtg gtagtcctaa tgatgaattt gttctggaga 780
ttctcgatgg ggatccaact gggcttggac taaagagtga aaccataggc aaagatacgc 840
gtttagtgct ggagaatcct aatggaaatt ccatcgtggc tcgtgttaag atctacaaga 900
acggttattc aggatgaaga agaaatcctt tgatttcccc cccccctct tcctttaaaa 960 ttcaacataa taaaaaaaaa aaaaaaaaa 989

<210> SEQ ID NO 27
<211> LENGTH: 148
<212> TYPE: PRT
<213> ORGANISM: Lutzomyia longipalpis

<400> SEQUENCE: 27

```
Met Asn Ser Val Asn Thr Leu Ile Leu Thr Leu Leu Phe Ala Ile Phe
1               5                   10                  15

Leu Leu Val Lys Arg Ser Gln Ala Phe Leu Pro Ser Asp Pro Ser Ile
            20                  25                  30

Cys Val Lys Asn Leu Val Leu Asp Thr Gly Arg Thr Cys Glu Glu Ser
        35                  40                  45

Glu Tyr Phe Pro Asp Ile Lys Asn Val Lys Asn Gly Lys Arg Val Tyr
    50                  55                  60

Ile Val Cys Thr Asp Ser Asp Ala Val Asp Tyr Lys Phe Tyr Ile Cys
65                  70                  75                  80

Phe Asp Met Asn Arg Leu Ser Gly Pro Pro Tyr Pro Glu Glu Glu Ile
                85                  90                  95

Leu Arg Glu Ser Thr Val Thr Tyr Ala Gln Ile Tyr Glu Leu Met Thr
            100                 105                 110

Thr Glu Thr Thr Glu Thr Lys Lys Pro Lys Lys Lys Pro Lys Asn Ser
        115                 120                 125

Lys Thr Asp Asp Pro Pro Ala Ile Arg Pro Gly Phe Ser Phe Arg Asn
    130                 135                 140

Ser Ile Ser Val
145
```

<210> SEQ ID NO 28
<211> LENGTH: 826
<212> TYPE: DNA

<213> ORGANISM: Lutzomyia longipalpis

<400> SEQUENCE: 28
gtcttttcct gagtgtttca ttaacaaaat gaattcagta aacactttaa ttttaactct 60
tctatttgca attttttat tagtgaaaag gtctcaggct tttcttccat ctgacccaag 120
tatctgtgtt aaaaatttag tattggatac aggaaggact tgtgaggaaa gtgaatattt 180
tccggatatc aagaacgtta aaaatggaaa aagagtttac attgtctgca ctgattcaga 240
tgcagttgat tataaatttt atatttgttt cgatatgaat cgtctttctg gaccaccgta 300
tcctgaggaa gaaatccttc gtgaatcaac ggtaacttat gcccaaattt atgagctgat 360
gactacggaa accactgaaa ccaaaaagcc aaaaaagaaa ccaaagaatt caaaaacgga 420
cccagaccct ccagcaattc gtccaggatt ttcatttaga aattcaattt ctgtttaatt 480
ttacaattta ttttgaaaga aaaatgatat ttcgaaatat tctatacaaa aaaacaacag 540
ttataaaacg aaaattcaat catttcaatg agaaaactta gtcttgagta aggtttattc 600
accacccgac gccacgctat ggtgaataat tttctttatt caccacatca aaatgacggc 660
ttataaactt caacaaatag tttggaaaat acatttctaa ctaatgcaat gtttacttaa 720
aatcacttta caaattcacg catttgagat gcaacaaata tatacaattc aacgatataa 780
actttccaca aggaaaactt tcaaccaaaa aaaaaaaaaa aaaaaa 826

<210> SEQ ID NO 29
<211> LENGTH: 397
<212> TYPE: PRT
<213> ORGANISM: Lutzomyia longipalpis

<400> SEQUENCE: 29

Met Lys Leu Phe Phe Phe Leu Tyr Thr Phe Gly Leu Val Gln Thr Ile
1 5 10 15

Phe Gly Val Glu Ile Lys Gln Gly Phe Lys Trp Asn Lys Ile Leu Tyr
20 25 30

Glu Gly Asp Thr Ser Glu Asn Phe Asn Pro Asp Asn Asn Ile Leu Thr
35 40 45

Ala Phe Ala Tyr Asp Pro Glu Ser Gln Lys Leu Phe Leu Thr Val Pro
50 55 60

Arg Lys Tyr Pro Glu Thr Met Tyr Thr Leu Ala Glu Val Asp Thr Glu
65 70 75 80

Lys Asn Ser Phe Glu Ser Gly Asp Thr Ser Pro Leu Leu Gly Lys Phe
85 90 95

Ser Gly His Glu Thr Gly Lys Glu Leu Thr Ser Val Tyr Gln Pro Val
100 105 110

Ile Asp Glu Cys His Arg Leu Trp Val Val Asp Val Gly Ser Val Glu
115 120 125

Arg Asn Ser Asp Gly Thr Glu Gly Gln Pro Glu His Asn Pro Thr Leu
130 135 140

Val Ala Tyr Asp Leu Lys Glu Ala Asn Tyr Pro Glu Val Ile Arg Tyr
145 150 155 160

Thr Phe Pro Asp Asn Ser Ile Glu Lys Pro Thr Phe Leu Gly Gly Phe
165 170 175

Ala Val Asp Val Val Lys Pro Asp Glu Cys Ser Glu Thr Phe Val Tyr
180 185 190

Ile Thr Asn Phe Leu Thr Asn Ala Leu Ile Val Tyr Asp His Lys Asn
195 200 205

```
Lys Asp Ser Trp Thr Val Gln Asp Ser Thr Phe Gly Pro Asp Lys Lys
    210                 215                 220

Ser Lys Phe Asp His Asp Gly Gln Gln Tyr Glu Tyr Glu Ala Gly Ile
225                 230                 235                 240

Phe Gly Ile Thr Leu Gly Glu Arg Asp Asn Glu Gly Asn Arg Gln Ala
                245                 250                 255

Tyr Tyr Leu Val Ala Ser Ser Thr Lys Leu His Ser Ile Asn Thr Lys
            260                 265                 270

Glu Leu Lys Gln Lys Gly Ser Lys Val Asn Ala Asn Tyr Leu Gly Asp
        275                 280                 285

Arg Gly Glu Ser Thr Asp Ala Ile Gly Leu Val Tyr Asp Pro Lys Thr
    290                 295                 300

Lys Thr Ile Phe Phe Val Glu Ser Asn Ser Lys Arg Val Ser Cys Trp
305                 310                 315                 320

Asn Thr Gln Glu Thr Leu Asn Lys Asp Lys Ile Asp Val Ile Tyr His
                325                 330                 335

Asn Ala Asp Phe Ser Phe Gly Thr Asp Ile Ser Ile Asp Ser Gln Asp
            340                 345                 350

Asn Leu Trp Phe Leu Ala Asn Gly Leu Pro Pro Leu Glu Asn Ser Asp
        355                 360                 365

Lys Phe Val Phe Thr Lys Pro Arg Tyr Gln Ile Phe Lys Val Asn Ile
    370                 375                 380

Gln Glu Ala Ile Ala Gly Thr Lys Cys Glu Lys Asn Leu
385                 390                 395


<210> SEQ ID NO 30
<211> LENGTH: 1325
<212> TYPE: DNA
<213> ORGANISM: Lutzomyia longipalpis

<400> SEQUENCE: 30

atcattcaaa aggcagcagc acaatgaagt tatttttctt tctttacact tttggtctag      60

tccaaacgat ttttggagta gaaattaaac aaggatttaa atggaataaa atcctttatg     120

agggcgatac atcagaaaac ttcaatccag ataacaacat ccttacggct tttgcgtacg     180

atcctgagag tcagaaactc ttcctaactg tcccgaggaa atatcccgaa actatgtaca     240

ctttggcaga agttgatact gagaaaaatt cttttgaatc gggagatact tccccgctcc     300

ttggaaaatt cagtggtcat gaaactggga aagaacttac atcagtttat cagccagtta     360

tcgatgaatg tcatcgtctt tgggttgttg atgttggatc agtagaacgt aactcagacg     420

gcacagaagg tcagccagaa cataatccta cccttgtggc gtacgatctc aaagaagcca     480

actatcctga agttattcgt tacacgtttc ccgataattc cattgagaag cccacatttc     540

tgggtggatt tgccgttgat gttgtaaagc cggatgaatg cagtgaaact tttgtctaca     600

tcacaaactt cctcaccaac gccctcatag tatacgatca taagaataag gactcctgga     660

cggtacaaga ttcaactttt ggaccagata aaaagtcaaa gtttgaccac gatggacaac     720

agtatgaata cgaagcagga atcttcggga ttacccttgg agagagagat aacgaaggaa     780

atcgtcaagc gtactattta gtagcaagta gtaccaaact tcacagcatc aacaccaaag     840

aactgaagca aaaaggaagc aaagttaatg caaattattt gggagatcgt ggtgaatcca     900

ccgatgccat aggcttagtt tacgatccaa aaaccaaaac tatcttcttc gttgagtcaa     960

atagcaaaag agtatcatgc tggaataccc aggaaacact aaacaaggat aaaattgatg    1020

taatctatca caatgcagac ttttcctttg gaacagatat atcgattgat agtcaggata    1080
```

-continued

```
atttgtggtt cctagcaaat ggacttccac ctctggaaaa ttctgataaa tttgtcttta   1140

caaagccacg ttatcaaata ttcaaagtca acattcaaga agcaattgct ggaactaaat   1200

gtgaaaagaa tctttaacaa atgaaacttt gtagaaaaat acataatatc tgaataaaaa   1260

gtcataaatg taccataaaa aaaaaaaaaa aaaaaaaaaa aaaaaaaaaa aaaaaaaaaa   1320

aaaaa                                                               1325


<210> SEQ ID NO 31
<211> LENGTH: 350
<212> TYPE: PRT
<213> ORGANISM: Lutzomyia longipalpis

<400> SEQUENCE: 31

Met Thr Phe Leu Ile Ile Leu Gly Ala Phe Leu Leu Val Gln Ile Ile
1               5                   10                  15

Thr Ala Ser Ala Leu Gly Leu Pro Glu Gln Phe Lys Gly Leu Glu Asp
            20                  25                  30

Leu Pro Lys Lys Pro Leu Ala Glu Thr Tyr Tyr His Glu Gly Leu Asn
        35                  40                  45

Asp Gly Lys Thr Asp Glu Met Val Asp Ile Phe Lys Ser Leu Ser Asp
    50                  55                  60

Glu Phe Lys Phe Ser Asp Glu Asn Leu Asp Val Gly Glu Glu Lys Asn
65                  70                  75                  80

Tyr Lys Lys Arg Asp Ile Thr Gln Asn Ser Val Ala Arg Asn Phe Leu
                85                  90                  95

Ser Asn Val Lys Gly Ile Pro Ser Met Pro Ser Leu Pro Ser Met Pro
            100                 105                 110

Ser Met Pro Ser Ile Pro Ser Leu Trp Ser Ser Gln Thr Gln Ala Ala
        115                 120                 125

Pro Asn Thr Ala Leu Ala Leu Pro Glu Ser Asp Tyr Ser Leu Leu Asp
    130                 135                 140

Met Pro Asn Ile Val Lys Asn Phe Leu Lys Glu Thr Arg Asp Leu Tyr
145                 150                 155                 160

Asn Asp Val Gly Ala Phe Leu Lys Ala Ile Thr Glu Ala Leu Thr Asn
                165                 170                 175

Arg Ser Ser Ser Ser Gln Leu Leu Ser Ser Pro Met Val Ser Thr Asn
            180                 185                 190

Lys Thr Lys Glu Phe Ile Arg Asn Glu Ile Gln Lys Val Arg Lys Val
        195                 200                 205

Arg Asn Phe Val Gln Glu Thr Leu Gln Lys Ile Arg Asp Ile Ser Ala
    210                 215                 220

Ala Ile Ala Lys Lys Val Lys Ser Ser Glu Cys Leu Ser Asn Leu Thr
225                 230                 235                 240

Asp Ile Lys Gly Leu Val Ser Asp Gly Ile Asn Cys Leu Lys Glu Lys
                245                 250                 255

Phe Asn Asp Gly Lys Arg Ile Ile Leu Gln Leu Tyr Asn Asn Leu Leu
            260                 265                 270

Lys Gly Leu Lys Ile Pro Asn Asp Leu Met Val Glu Leu Lys Lys Cys
        275                 280                 285

Asp Thr Asn Gln Asn Asn Thr Leu Gly Arg Ile Ile Cys Tyr Phe Leu
    290                 295                 300

Thr Pro Leu Gln Leu Glu Lys Glu Gln Ile Leu Leu Pro Val Glu Phe
305                 310                 315                 320
```

-continued

```
Ile Lys Arg Ile Leu Glu Leu Thr His Tyr Phe Ser Thr Met Lys Glu
                325                 330                 335

Asp Leu Ile Asn Cys Gly Ile Thr Thr Ile Ala Ser Ile Thr
            340                 345                 350
```

<210> SEQ ID NO 32
<211> LENGTH: 1275
<212> TYPE: DNA
<213> ORGANISM: Lutzomyia longipalpis

<400> SEQUENCE: 32

```
ctttaaagca aaaatttgt gggaaaggaa gttacccgga gatgacgttt ctaattatac      60

ttggtgcatt tctccttgtt caaattatta cagcttcagc tttaggattg cctgaacagt     120

ttaaaggttt agaggattta cctaaaaaac ctttggcaga gacttattat cacgaaggat     180

tgaatgatgg aaaaacggat gaaatggtgg atatttttaa aagtcttagc gatgaattta     240

aattcagtga tgaaaattta gatgttggtg aggagaaaaa ttacaagaaa cgtgatataa     300

cccaaaattc agtggcaagg aacttcctat caaacgtaaa gggaattcct tcaatgccat     360

cactcccttc aatgccttca atgccatcaa ttccttcact ttggtcaagt cagacacagg     420

cggcaccaaa taccgcactt gcccttcctg aatctgatta ttcccttcta gatatgccga     480

atattgtgaa aaatttccta aaggaaacaa gagacctcta taacgatgtt ggagcttttc     540

ttaaggcaat tacagaagct ttaacaaata gatcttcatc atctcaactt ctttcctccc     600

caatggtgag cacgaataaa accaaagaat ttattcggaa tgaaatacaa aaagtccgaa     660

aagtgagaaa tttcgtccag gaaactcttc agaaaatccg agacatttct gctgctattg     720

ccaaaaaggt aaaatcatca gaatgtctgt ccaatcttac ggacatcaaa ggacttgtat     780

cagacggaat taattgttta aaggaaaaat tcaatgatgg aaaacgaatt atcctgcaat     840

tgtacaataa tttactaaaa ggactcaaaa ttccaaatga cctaatggtt gaattgaaga     900

aatgtgatac aaatcaaaac aatactttgg gaagaataat ctgttatttt ttgacaccat     960

tgcaactgga aaaagaacaa attcttctac ctgtagaatt tataaagcgc attcttgaat    1020

taacccacta cttttccaca atgaaagaag atcttatcaa ctgtggcatc acaacgattg    1080

catccattac gtaaaaaatg gaaaaatgtg ccggtgaaat gcttgaaatc accaaagaaa    1140

tttcatcgca aataacagtt ccagaataac caaattttaa tgattacttc tcaaggaaaa    1200

tactaccaaa aggcattaat taaaacgatg ttttttataa acaatgtaag aaaaaaaaaa    1260

aaaaaaaaaa aaaaa                                                     1275
```

<210> SEQ ID NO 33
<211> LENGTH: 60
<212> TYPE: PRT
<213> ORGANISM: Lutzomyia longipalpis

<400> SEQUENCE: 33

```
Met Leu Lys Ile Val Leu Phe Leu Ser Val Leu Ala Val Leu Val Ile
1               5                   10                  15

Cys Val Ala Ala Met Pro Gly Ser Asn Val Pro Trp His Ile Ser Arg
            20                  25                  30

Glu Glu Leu Glu Lys Leu Arg Glu Ala Arg Lys Asn His Lys Ala Leu
        35                  40                  45

Glu Lys Ala Ile Asp Glu Leu Ile Asp Lys Tyr Leu
    50                  55                  60
```

<210> SEQ ID NO 34
<211> LENGTH: 413
<212> TYPE: DNA
<213> ORGANISM: Lutzomyia longipalpis

<400> SEQUENCE: 34
agttaatctt ctgtcaagct acaaaaatgc ttaaaatcgt tttatttcta tcagttttgg 60
ctgtattagt gatttgtgta gcagcaatgc caggatccaa tgttccttgg cacatttcac 120
gagaagagct tgagaagctt cgtgaagctc gaaagaatca caaggcactc gagaaggcaa 180
ttgatgaatt aattgacaaa tatctctgat tttgaagagc aaggaagagg aaataaacgg 240
ccgaggaagg attttcttta gagattcttc tttttattac ttcaaaccta acttcaaaat 300
cagtctgata ttttttttaat ttgaaaaaaa tattgaaaat tttaactatt tgtgaaattt 360
aaataaataa agaatgtcag aagcaaaaaa aaaaaaaaaa aaaaaaaaaa aaa 413

<210> SEQ ID NO 35
<211> LENGTH: 120
<212> TYPE: PRT
<213> ORGANISM: Lutzomyia longipalpis

<400> SEQUENCE: 35

Met Lys Phe Ser Cys Pro Val Phe Val Ala Ile Phe Leu Leu Cys Gly
1 5 10 15

Phe Tyr Arg Val Glu Gly Ser Ser Gln Cys Glu Glu Asp Leu Lys Glu
20 25 30

Glu Ala Glu Ala Phe Phe Lys Asp Cys Asn Glu Ala Lys Ala Asn Pro
35 40 45

Gly Glu Tyr Glu Asn Leu Thr Lys Glu Glu Met Phe Glu Glu Leu Lys
50 55 60

Glu Tyr Gly Val Ala Asp Thr Asp Met Glu Thr Val Tyr Lys Leu Val
65 70 75 80

Glu Glu Cys Trp Asn Glu Leu Thr Thr Thr Asp Cys Lys Arg Phe Leu
85 90 95

Glu Glu Ala Glu Cys Phe Lys Lys Lys Asn Ile Cys Lys Tyr Phe Pro
100 105 110

Asp Glu Val Lys Leu Lys Lys Lys
115 120

<210> SEQ ID NO 36
<211> LENGTH: 428
<212> TYPE: DNA
<213> ORGANISM: Lutzomyia longipalpis

<400> SEQUENCE: 36
aattttcacc atgaagtttt cttgcccagt tttcgttgca attttccttt tgtgcggatt 60
ttatcgtgtt gaggggtcat cacaatgtga agaagattta aaagaagaag ctgaagcttt 120
ctttaaggat tgcaatgaag caaaagccaa tcctggtgaa tacgagaatc tcaccaaaga 180
agaaatgttt gaagaattga aagaatatgg agttgctgac acagacatgg agacagttta 240
caaacttgtg gaagaatgtt ggaatgaatt aacaacaacg gattgtaaga gatttctcga 300
agaggctgaa tgcttcaaga agaagaatat ttgtaaatat ttcccagatg aagtgaaatt 360
gaagaagaaa taaattttta gcttgaaaaa aaaaaaaaaa aaaaaaaaaa aaaaaaaaaa 420
aaaaaaaa 428

<210> SEQ ID NO 37

<211> LENGTH: 572
<212> TYPE: PRT
<213> ORGANISM: Lutzomyia longipalpis

<400> SEQUENCE: 37

```
Met Leu Phe Phe Leu Asn Phe Phe Val Leu Val Phe Ser Ile Glu Leu
1               5                   10                  15

Ala Leu Leu Thr Ala Ser Ala Ala Ala Glu Asp Gly Ser Tyr Glu Ile
            20                  25                  30

Ile Ile Leu His Thr Asn Asp Met His Ala Arg Phe Asp Gln Thr Asn
        35                  40                  45

Ala Gly Ser Asn Lys Cys Gln Glu Lys Asp Lys Ile Ala Ser Lys Cys
    50                  55                  60

Tyr Gly Gly Phe Ala Arg Val Ser Thr Met Val Lys Lys Phe Arg Glu
65                  70                  75                  80

Glu Asn Gly Ser Ser Val Leu Phe Leu Asn Ala Gly Asp Thr Tyr Thr
                85                  90                  95

Gly Thr Pro Trp Phe Thr Leu Tyr Lys Glu Thr Ile Ala Thr Glu Met
            100                 105                 110

Met Asn Ile Leu Arg Pro Asp Ala Ala Ser Leu Gly Asn His Glu Phe
        115                 120                 125

Asp Lys Gly Val Glu Gly Leu Val Pro Phe Leu Asn Gly Val Thr Phe
    130                 135                 140

Pro Ile Leu Thr Ala Asn Leu Asp Thr Ser Gln Glu Pro Thr Met Thr
145                 150                 155                 160

Asn Ala Lys Asn Leu Lys Arg Ser Met Ile Phe Thr Val Ser Gly His
                165                 170                 175

Arg Val Gly Val Ile Gly Tyr Leu Thr Pro Asp Thr Lys Phe Leu Ser
            180                 185                 190

Asp Val Gly Lys Val Asn Phe Ile Pro Glu Val Glu Ala Ile Asn Thr
        195                 200                 205

Glu Ala Gln Arg Leu Lys Lys Glu Glu Asn Ala Glu Ile Ile Ile Val
    210                 215                 220

Val Gly His Ser Gly Leu Ile Lys Asp Arg Glu Ile Ala Glu Lys Cys
225                 230                 235                 240

Pro Leu Val Asp Ile Ile Val Gly Gly His Ser His Thr Phe Leu Tyr
                245                 250                 255

Thr Gly Ser Gln Pro Asp Arg Glu Val Pro Val Asp Val Tyr Pro Val
            260                 265                 270

Val Val Thr Gln Ser Ser Gly Lys Lys Val Pro Ile Val Gln Ala Tyr
        275                 280                 285

Cys Phe Thr Lys Tyr Leu Gly Tyr Phe Lys Val Thr Ile Asn Gly Lys
    290                 295                 300

Gly Asn Val Val Gly Trp Thr Gly Gln Pro Ile Leu Leu Asn Asn Asn
305                 310                 315                 320

Ile Pro Gln Asp Gln Glu Val Leu Thr Ala Leu Glu Lys Tyr Arg Glu
                325                 330                 335

Arg Val Glu Asn Tyr Gly Asn Arg Val Ile Gly Val Ser Arg Val Ile
            340                 345                 350

Leu Asn Gly Gly His Thr Glu Cys Arg Phe His Glu Cys Asn Met Gly
        355                 360                 365

Asn Leu Ile Thr Asp Ala Phe Val Tyr Ala Asn Val Ile Ser Thr Pro
    370                 375                 380

Met Ser Thr Asn Ala Trp Thr Asp Ala Ser Val Val Leu Tyr Gln Ser
```

-continued

```
385                 390                 395                 400

Gly Gly Ile Arg Ala Pro Ile Asp Pro Arg Thr Ala Ala Gly Ser Ile
                405                 410                 415

Thr Arg Leu Glu Leu Asp Asn Val Leu Pro Phe Gly Asn Ala Leu Tyr
            420                 425                 430

Val Val Lys Val Pro Gly Asn Val Leu Arg Lys Ala Leu Glu His Ser
        435                 440                 445

Val His Arg Tyr Ser Asn Thr Ser Gly Trp Gly Glu Phe Pro Gln Val
    450                 455                 460

Ser Gly Leu Lys Ile Arg Phe Asn Val Asn Glu Glu Ile Gly Lys Arg
465                 470                 475                 480

Val Lys Ser Val Lys Val Leu Cys Ser Asn Cys Ser Gln Pro Glu Tyr
                485                 490                 495

Gln Pro Leu Arg Asn Lys Lys Thr Tyr Asn Val Ile Met Asp Ser Phe
            500                 505                 510

Met Lys Asp Gly Gly Asp Gly Tyr Ser Met Phe Lys Pro Leu Lys Ile
        515                 520                 525

Ile Lys Thr Leu Pro Leu Gly Asp Ile Glu Thr Val Glu Ala Tyr Ile
    530                 535                 540

Glu Lys Met Gly Pro Ile Phe Pro Ala Val Glu Gly Arg Ile Thr Val
545                 550                 555                 560

Leu Gly Gly Leu Gln Lys Ser Asp Glu Asp Trp His
                565                 570


<210> SEQ ID NO 38
<211> LENGTH: 1839
<212> TYPE: DNA
<213> ORGANISM: Lutzomyia longipalpis

<400> SEQUENCE: 38

agttgcaaga atttcttcat tgcgttaaga tgttgttttt ccttaacttt tttgtgctgg      60

tgttcagcat agaactggcg ttgttaacag catcagcagc agcagaagac ggcagctatg     120

agatcataat tcttcacacc aatgatatgc acgcgcgttt tgatcaaacc aatgctggaa     180

gcaacaaatg ccaagaaaaa gacaagattg cttccaaatg ctacggagga tttgcaagag     240

tttcaacaat ggtgaaaaaa ttccgagaag aaaatggcag cagtgtcttg ttcttgaatg     300

ctggtgacac gtatacaggt accccatggt ttaccctcta caaggagacc attgcaacgg     360

agatgatgaa catccttcgt ccagatgcag cctcactggg aaatcatgaa ttcgacaaag     420

gagtagaagg actcgtgcca ttcctcaatg gtgtcacctt ccctatttta acagcgaatt     480

tggacacttc tcaagagcca acaatgacca atgctaaaaa tctcaaacgc tcaatgattt     540

ttacggtttc cgggcacaga gttggtgtaa ttggctacct aacgcctgat acaaaattcc     600

tctcggacgt tggtaaagtt aattttattc cggaagttga agccatcaat acggaagcac     660

agcgtctgaa gaaagaggaa aatgccgaaa taatcatcgt tgttggacat tcagggttga     720

taaaagatcg agaaattgca gagaaatgcc cactggttga cataattgtt ggaggacatt     780

cacacacatt cctctacaca ggaagtcagc ctgatcgtga ggttcctgta gacgtttatc     840

ctgttgttgt gacccaatcc agtgggaaga aagttccaat tgttcaagcc tattgcttta     900

caaagtattt ggggtacttt aaagtgacga tcaacggaaa aggaaatgtt gtgggatgga     960

ctgggcagcc aattctcctt aataacaaca ttccccaaga tcaggaagtt ctcactgctc    1020

ttgaaaagta cagagaacgc gtggaaaact atggaaatcg cgtaattgga gtttcccgtg    1080
```

```
taattctcaa tggggggcat actgaatgtc gtttccatga atgcaatatg ggtaatctca   1140

tcacggacgc ttttgtgtat gccaatgtaa tcagtacacc aatgagtacg aatgcctgga   1200

cagatgcaag tgttgttctg tatcaaagtg gtggcattcg tgccccaatt gatcctcgta   1260

ccgcggcagg gagcatcaca cgcctcgagt tggacaatgt tctaccattt gggaatgcac   1320

tgtacgtcgt aaaagttcct gggaatgtct tacgcaaagc tttggaacat tcagttcatc   1380

gatactccaa cacttcggga tggggagaat ttccacaagt ttcggggcta aagattcgtt   1440

ttaacgtcaa tgaagaaatt ggaaaacgcg taaagtccgt taaagttctc tgtagcaatt   1500

gctctcaacc tgaataccaa ccactgagaa ataaaaaaac ttacaacgtt atcatggaca   1560

gttttatgaa ggatggaggt gatgggtata gcatgttcaa gcccttgaag atcatcaaga   1620

ccctcccact gggagatatt gaaacagtag aagcttatat tgagaaaatg ggccccattt   1680

tcccagcagt cgagggaagg atcactgttc ttgggggact tcaaaaatca gatgaggatt   1740

ggcattagaa acatcctgga cgttatggaa agaataaaag aaggatcata gaaaaaaaaa   1800

aaaaaaaaat aaaaaaaaaa aaaaaaaaaa aaaaaaaaa                         1839
```

<210> SEQ ID NO 39
<211> LENGTH: 86
<212> TYPE: PRT
<213> ORGANISM: Lutzomyia longipalpis

<400> SEQUENCE: 39

```
Met Lys Gln Ile Leu Leu Ile Ser Leu Val Val Ile Leu Ala Val Leu
1               5                   10                  15

Ala Phe Asn Val Ala Glu Gly Cys Asp Ala Thr Cys Gln Phe Arg Lys
            20                  25                  30

Ala Ile Glu Asp Cys Lys Lys Lys Ala Asp Asn Ser Asp Val Leu Gln
        35                  40                  45

Thr Ser Val Gln Thr Thr Ala Thr Phe Thr Ser Met Asp Thr Ser Gln
    50                  55                  60

Leu Pro Gly Asn Asn Val Phe Lys Ala Cys Met Lys Glu Lys Ala Lys
65                  70                  75                  80

Glu Phe Arg Ala Gly Lys
                85
```

<210> SEQ ID NO 40
<211> LENGTH: 419
<212> TYPE: DNA
<213> ORGANISM: Lutzomyia longipalpis

<400> SEQUENCE: 40

```
gtcagtgatc tgataagtta ttaaaatgaa gcaaatcctt ctaatctctt tggtggtgat     60

tcttgccgtg cttgccttca atgttgctga gggctgtgat gcaacatgcc aatttcgcaa    120

agccatagaa gactgcaaga agaaggcgga taatagcgat gttttgcaga cttctgtaca    180

aacaactgca acattcacat caatggatac atcccaacta cctggaaata atgtcttcaa    240

agcatgcatg aaggagaagg ctaaggaatt tagggcagga aagtaagaga ttgaggaaaa    300

ttgtagccga agagagaagg aaggaaagtc ccatattttg tttgttaatt gtaacgaatt    360

ttgcgaaaaa aataaaatat tatgcactcc aaaaaaaaaa aaaaaaaaaa aaaaaaaaa     419
```

<210> SEQ ID NO 41
<211> LENGTH: 84
<212> TYPE: PRT
<213> ORGANISM: Lutzomyia longipalpis

<400> SEQUENCE: 41

Met Asn Val Leu Phe Val Ser Phe Thr Leu Thr Ile Leu Leu Leu Cys
1               5                   10                  15

Val Lys Ala Arg Pro Glu Asp Phe Val Ala Leu Gln Asp Gln Ala Asn
            20                  25                  30

Phe Gln Lys Cys Leu Glu Gln Tyr Pro Glu Pro Asn Gln Ser Gly Glu
        35                  40                  45

Val Leu Ala Cys Leu Lys Lys Arg Glu Gly Ala Lys Asp Phe Arg Glu
    50                  55                  60

Lys Arg Ser Leu Asp Asp Ile Glu Gly Thr Phe Gln Glu Ser Gly Asn
65                  70                  75                  80

Leu Trp Gly Ala

<210> SEQ ID NO 42
<211> LENGTH: 429
<212> TYPE: DNA
<213> ORGANISM: Lutzomyia longipalpis

<400> SEQUENCE: 42
tatttttaat aattctgtgt aaaatgaacg ttcttttcgt gtctttcacg ctcacaattc 60
ttcttctctg tgttaaggca cggccagaag atttcgtagc tcttcaggat caagctaatt 120
tccagaaatg cctcgaacaa tatccagaac caaatcaatc tggagaagtt cttgcgtgcc 180
tcaagaagcg cgaaggtgcc aaagatttcc gggaaaagag gagcctggat gacatagaag 240
ggactttcca agagtctgga aatctctggg gtgcatagga agctcagagg acttctaatc 300
aatctgtgag aagagaaccc aacggctaga gaaaatttaa ggaaaataaa gaaattaatg 360
aagcattaaa aaaaaaaaaa aaaaaaaaaa aaaaaaaaaa aaaaaaaaaa aaaaaaaaaa 420
aaaaaaaaa 429

<210> SEQ ID NO 43
<211> LENGTH: 626
<212> TYPE: PRT
<213> ORGANISM: Lutzomyia longipalpis

<400> SEQUENCE: 43

Met Lys Ile Thr Val Ile Leu Phe Thr Gly Phe Thr Ile Ala Leu Val
1               5                   10                  15

Ser Ser Ala Val Leu Lys Lys Asn Gly Glu Thr Ile Glu Glu Glu Glu
            20                  25                  30

Val Arg Ala Glu Gln Arg Leu Arg Glu Ile Asn Glu Glu Leu Asp Arg
        35                  40                  45

Arg Lys Asn Ile Asn Thr Val Ala Ala Trp Ala Tyr Ala Ser Asn Ile
    50                  55                  60

Thr Glu Val Asn Leu Lys Asn Met Asn Asp Val Ser Val Glu Thr Ala
65                  70                  75                  80

Lys Tyr Tyr Lys Glu Leu Ala Ser Glu Leu Lys Gly Phe Asn Ala Lys
                85                  90                  95

Glu Tyr Lys Ser Glu Asp Leu Lys Arg Gln Ile Lys Lys Leu Ser Lys
            100                 105                 110

Leu Gly Tyr Ser Ala Leu Pro Ser Glu Lys Tyr Lys Glu Leu Leu Glu
        115                 120                 125

Ala Ile Thr Trp Met Glu Ser Asn Tyr Ala Lys Val Lys Val Cys Ser
    130                 135                 140

-continued

```
Tyr Lys Asp Pro Lys Lys Cys Asp Leu Ala Leu Glu Pro Glu Ile Thr
145                 150                 155                 160

Glu Ile Leu Ile Lys Ser Arg Asp Pro Glu Glu Leu Lys Tyr Tyr Trp
                165                 170                 175

Lys Gln Trp Tyr Asp Lys Ala Gly Thr Pro Thr Arg Glu Ser Phe Asn
            180                 185                 190

Lys Tyr Val Gln Leu Asn Arg Glu Ala Ala Lys Leu Asp Gly Phe Tyr
        195                 200                 205

Ser Gly Ala Glu Ser Trp Leu Asp Glu Tyr Glu Asp Glu Thr Phe Glu
    210                 215                 220

Lys Gln Leu Glu Asp Ile Phe Ala Gln Ile Arg Pro Leu Tyr Glu Gln
225                 230                 235                 240

Leu His Ala Tyr Val Arg Phe Lys Leu Arg Glu Lys Tyr Gly Asn Asp
                245                 250                 255

Val Val Ser Glu Lys Gly Pro Ile Pro Met His Leu Leu Gly Asn Met
            260                 265                 270

Trp Gly Gln Thr Trp Ser Glu Val Ala Pro Ile Leu Val Pro Tyr Pro
        275                 280                 285

Glu Lys Lys Leu Leu Asp Val Thr Asp Glu Met Val Lys Gln Gly Tyr
    290                 295                 300

Thr Pro Ile Ser Met Phe Glu Lys Gly Asp Glu Phe Phe Gln Ser Leu
305                 310                 315                 320

Asn Met Thr Lys Leu Pro Lys Thr Phe Trp Glu Tyr Ser Ile Leu Glu
                325                 330                 335

Lys Pro Gln Asp Gly Arg Glu Leu Ile Cys His Ala Ser Ala Trp Asp
            340                 345                 350

Phe Tyr Thr Lys Asp Asp Val Arg Lys Gln Cys Thr Arg Val Thr Met
        355                 360                 365

Asp Gln Phe Phe Thr Ala His His Glu Leu Gly His Ile Gln Tyr Tyr
    370                 375                 380

Leu Gln Tyr Gln His Leu Pro Ser Val Tyr Arg Glu Gly Ala Asn Pro
385                 390                 395                 400

Gly Phe His Glu Ala Val Gly Asp Val Leu Ser Leu Ser Val Ser Ser
                405                 410                 415

Pro Lys His Leu Glu Lys Val Gly Leu Leu Lys Asp Phe Lys Phe Asp
            420                 425                 430

Glu Glu Ser Gln Ile Asn Gln Leu Leu Asn Leu Ala Leu Asp Lys Met
        435                 440                 445

Ala Phe Leu Pro Phe Ala Tyr Thr Ile Asp Lys Tyr Arg Trp Gly Val
    450                 455                 460

Phe Arg Gly Glu Ile Ser Pro Ser Glu Tyr Asn Cys Lys Phe Trp Glu
465                 470                 475                 480

Met Arg Ser Tyr Tyr Gly Gly Ile Glu Pro Pro Ile Ala Arg Ser Glu
                485                 490                 495

Ser Asp Phe Asp Pro Pro Ala Lys Tyr His Ile Ser Ser Asp Val Glu
            500                 505                 510

Tyr Leu Arg Tyr Leu Val Ser Phe Ile Ile Gln Phe Gln Phe His Gln
        515                 520                 525

Ala Val Cys Gln Lys Thr Gly Gln Phe Val Pro Asn Asp Pro Glu Lys
    530                 535                 540

Thr Leu Leu Asn Cys Asp Ile Tyr Gln Ser Ala Glu Ala Gly Asn Ala
545                 550                 555                 560

Phe Lys Glu Met Leu Lys Leu Gly Ser Ser Lys Pro Trp Pro Asp Ala
```

```
            565                 570                 575

Met Glu Ile Leu Thr Gly Gln Arg Lys Met Asp Ala Ser Ala Leu Ile
        580                 585                 590

Glu Tyr Phe Arg Pro Leu Ser Glu Trp Leu Gln Lys Lys Asn Lys Glu
    595                 600                 605

Leu Gly Ala Tyr Val Gly Trp Asp Lys Ser Thr Lys Cys Val Lys Asn
    610                 615                 620

Val Ser
625


<210> SEQ ID NO 44
<211> LENGTH: 2121
<212> TYPE: DNA
<213> ORGANISM: Lutzomyia longipalpis

<400> SEQUENCE: 44

gtatatcaag tatcattcaa gtgaatcatt ggctccgtaa tttgtacaaa agaaaaaaaa      60

agttgataaa atcatgaaaa tcactgtgat tttattcacg ggatttacaa ttgccctcgt     120

gagtagtgct gtgcttaaga aaaacggtga aactattgaa gaagaagaag taagagctga     180

gcaacgactt agagagatca atgaggaact tgatcgtagg aagaatatca atactgtagc     240

cgcttgggct tatgcatcca atattactga ggtcaatctc aagaacatga atgatgtgtc     300

ggttgaaacc gcgaaatact acaaggaact tgcatctgaa ttgaagggat tcaatgccaa     360

ggaatacaag agtgaggatc tgaagagaca aattaagaag ctaagcaagt tgggatatag     420

tgctttacca tctgagaagt ataaggagct tttggaagct atcacatgga tggaatcgaa     480

ttatgcaaaa gtgaaagttt gctcatacaa ggatccaaag aaatgtgatt tagcacttga     540

acctgaaatt acggaaatcc ttattaaaag tcgagatcct gaggaactta aatattattg     600

gaaacaatgg tacgacaaag ctggcacacc aactcgagag agttttaata agtatgtaca     660

actaaatcgt gaagcagcga aattggatgg attttattcg ggtgcagaat cttggcttga     720

tgaatatgaa gatgagacat ttgagaaaca acttgaggat atcttcgccc aaattcgccc     780

actgtacgag caactccatg cttatgttag attcaagctg agggaaaagt atggaaatga     840

cgttgtttcg gagaaaggtc ccattccaat gcatctcttg ggaacatgt ggggtcaaac      900

gtggagtgaa gttgccccaa ttttagtccc ataccccgaa aagaagctcc tcgatgttac     960

cgatgagatg gttaagcagg gatacacacc aatttctatg tttgaaaaag gagacgaatt    1020

tttccaaagc ttgaatatga cgaaacttcc aaaaaccttc tgggagtaca gtattttgga    1080

aaaaccccaa gatggtaggg aattgatctg ccatgcaagt gcatgggact tctatacaaa    1140

ggatgatgta aggattaaac agtgtaccag agttacaatg gatcaattct tcacggctca    1200

tcatgagctt ggtcacattc aatattattt gcaatatcaa catttgccga gtgtttacag    1260

agaaggtgcc aatccaggct ttcacgaggc tgttggggat gttctctctc tttcggtatc    1320

aagtcctaaa catttggaaa aagttggttt gcttaaagac ttcaaatttg atgaagaatc    1380

ccagataaat caacttctaa atttagctct ggataaaatg gcattcctcc catttgccta    1440

taccattgat aaatatcgct ggggtgtgtt tcggggtgaa atttcgccgt ctgagtacaa    1500

ttgcaaattt tgggaaatgc gttcctacta tggtggtata gaaccaccaa ttgcacgttc    1560

tgagagtgat tttgatccac cagcaaaata tcatatttca tcggatgttg agtacctcag    1620

gtatttggtt tccttcatta ttcagttcca attccatcaa gctgtgtgcc aaaagactgg    1680

tcagttcgta ccgaatgatc cggagaagac tcttctaaat tgtgacatct accagagtgc    1740
```

```
tgaggctggt aatgccttca aagaaatgct caaattggga tcctcaaaac catggccaga   1800

tgcaatggaa attcttacgg ggcaaaggaa aatggatgct tctgcattaa ttgagtactt   1860

ccgtccactc agtgagtggt tgcagaagaa gaataaggaa ctaggagctt atgttggctg   1920

ggacaaatct actaagtgtg tcaaaaacgt cagttaattt tttgtgagcc ctaaaaaata   1980

ttcataacat ttcaatatga caaaatatat gattttcgtg aaaactaagc atgagtaagt   2040

tttttttgtg aatttttagc agtttcattt cagaataaac gtcaaatttt taaaaaaaaa   2100

aaaaaaaaaa aaaaaaaaaa a                                             2121


<210> SEQ ID NO 45
<211> LENGTH: 42
<212> TYPE: PRT
<213> ORGANISM: Lutzomyia longipalpis

<400> SEQUENCE: 45

Met Lys Thr Phe Ala Leu Ile Phe Leu Ala Leu Ala Val Phe Val Leu
1               5                   10                  15

Cys Ile Asp Gly Ala Pro Thr Phe Val Asn Leu Leu Asp Asp Val Gln
            20                  25                  30

Glu Glu Val Glu Val Asn Thr Tyr Glu Pro
        35                  40


<210> SEQ ID NO 46
<211> LENGTH: 463
<212> TYPE: DNA
<213> ORGANISM: Lutzomyia longipalpis

<400> SEQUENCE: 46

tcagttagtt gactaacaaa ccacaataga gacactaaaa tgaagacatt cgccttaatc     60

ttcttggctc ttgctgtttt tgtgctctgc attgacggag ctccaacttt tgtgaattta    120

ctggacgacg tacaggaaga ggtagaagtt aatacgtatg agccttagga agaaaatgtt    180

tgaggagttt caggcagagg cagagctttc ccagagaggg agcttttgcc ttgctgtaga    240

tttttaaaaa tgaatcaatt tgattggagc aattacgcta tatttgtggg aatatttttg    300

aattaaaaac taattatgga aattaatata taattttcag aatttcaata aattcatcaa    360

aattgtatta attaaaaaat attgtatgaa attcccaata aaagctttca aattaaaaaa    420

aaaaaaaaaa aaaaaaaaaa aaaaaaaaaa aaaaaaaaaa aaa                      463


<210> SEQ ID NO 47
<211> LENGTH: 139
<212> TYPE: PRT
<213> ORGANISM: Lutzomyia longipalpis

<400> SEQUENCE: 47

Met Asn His Leu Cys Phe Ile Ile Ile Ala Leu Phe Phe Leu Val Gln
1               5                   10                  15

Gln Ser Leu Ala Glu His Pro Glu Glu Lys Cys Ile Arg Glu Leu Ala
            20                  25                  30

Arg Thr Asp Glu Asn Cys Ile Leu His Cys Thr Tyr Ser Tyr Tyr Gly
        35                  40                  45

Phe Val Asp Lys Asn Phe Arg Ile Ala Lys Lys His Val Gln Lys Phe
    50                  55                  60

Lys Lys Ile Leu Val Thr Phe Gly Ala Val Pro Lys Lys Glu Lys Lys
65                  70                  75                  80
```

```
Lys Leu Leu Glu His Ile Glu Ala Cys Ala Asp Ser Ala Asn Ala Asp
                85                  90                  95

Gln Pro Gln Thr Lys Asp Glu Lys Cys Thr Lys Ile Asn Lys Tyr Tyr
            100                 105                 110

Arg Cys Val Val Asp Gly Lys Ile Leu Pro Trp Asn Ser Tyr Ala Asp
        115                 120                 125

Ala Ile Ile Lys Phe Asp Lys Thr Leu Asn Val
    130                 135


<210> SEQ ID NO 48
<211> LENGTH: 579
<212> TYPE: DNA
<213> ORGANISM: Lutzomyia longipalpis

<400> SEQUENCE: 48

ggccattatg gccggggata gaacttaatt gttgttaaaa tgaatcactt gtgctttatt      60

attattgctc tattcttttt ggttcaacaa tctttggctg aacatccaga agaaaaatgt     120

attagagaat tggcgagaac tgatgaaaac tgcattcttc attgtacgta ttcgtactac     180

ggattcgttg ataaaaattt caggatcgct aaaaaacatg ttcaaaaatt caaaaaaatc     240

ctagttacat tcggcgctgt tcctaagaaa gaaaaaaaga aactttaga gcacattgag     300

gcttgtgcgg attctgcgaa tgctgatcaa cctcaaacta aagatgaaaa atgtacaaaa     360

ataaataagt actatcgttg tgttgtggat ggaaaaatat taccctggaa tagttatgct     420

gatgcaatca ttaagtttga taaaaccctt aacgtatgaa gcaaagatat tcgaaaaaaa     480

aacatcaaga ttatgctgga aagaaaaaaa taaaaaaaaa ttgtgctaat caaattgaat     540

taacgcttaa tgctatatta aaaaaaaaaa aaaaaaaaa                           579


<210> SEQ ID NO 49
<211> LENGTH: 446
<212> TYPE: PRT
<213> ORGANISM: Lutzomyia longipalpis

<400> SEQUENCE: 49

Met Lys Ile Ile Phe Leu Ala Ala Phe Leu Leu Ala Asp Gly Ile Trp
1               5                   10                  15

Ala Ala Glu Glu Pro Ser Val Glu Ile Val Thr Pro Gln Ser Val Arg
            20                  25                  30

Arg His Ala Thr Pro Lys Ala Gln Asp Ala Arg Val Gly Ser Glu Ser
        35                  40                  45

Ala Thr Thr Ala Pro Arg Pro Ser Glu Ser Met Asp Tyr Trp Glu Asn
    50                  55                  60

Asp Asp Phe Val Pro Phe Glu Gly Pro Phe Lys Asp Ile Gly Glu Phe
65                  70                  75                  80

Asp Trp Asn Leu Ser Lys Ile Val Phe Glu Glu Asn Lys Gly Asn Ala
                85                  90                  95

Ile Leu Ser Pro Leu Ser Val Lys Leu Leu Met Ser Leu Leu Phe Glu
            100                 105                 110

Ala Ser Ala Ser Gly Thr Leu Thr Gln His Gln Leu Arg Gln Ala Thr
        115                 120                 125

Pro Thr Ile Val Thr His Tyr Gln Ser Arg Glu Phe Tyr Lys Asn Ile
    130                 135                 140

Phe Asp Gly Leu Lys Lys Lys Ser Asn Asp Tyr Thr Val His Phe Gly
145                 150                 155                 160

Thr Arg Ile Tyr Val Asp Gln Phe Val Thr Pro Arg Gln Arg Tyr Ala
```

-continued

```
                165                 170                 175

Ala Ile Leu Glu Lys His Tyr Leu Thr Asp Leu Lys Val Glu Asp Phe
            180                 185                 190

Ser Lys Ala Lys Glu Thr Thr Gln Ala Ile Asn Ser Trp Val Ser Asn
        195                 200                 205

Ile Thr Asn Glu His Ile Lys Asp Leu Val Lys Glu Glu Asp Val Gln
    210                 215                 220

Asn Ser Val Met Leu Met Leu Asn Ala Val Tyr Phe Arg Gly Leu Trp
225                 230                 235                 240

Arg Lys Pro Phe Asn Arg Thr Leu Pro Leu Pro Phe His Val Ser Ala
                245                 250                 255

Asp Glu Ser Lys Thr Thr Asp Phe Met Leu Thr Asp Gly Leu Tyr Tyr
            260                 265                 270

Phe Tyr Glu Ala Lys Glu Leu Asp Ala Lys Ile Leu Arg Ile Pro Tyr
        275                 280                 285

Lys Gly Lys Gln Tyr Ala Met Thr Val Ile Leu Pro Asn Ser Lys Ser
    290                 295                 300

Gly Ile Asp Ser Phe Val Arg Gln Ile Asn Thr Val Leu Leu His Arg
305                 310                 315                 320

Ile Lys Trp Leu Met Asp Glu Val Glu Cys Arg Val Ile Leu Pro Lys
                325                 330                 335

Phe His Phe Asp Met Thr Asn Glu Leu Lys Glu Ser Leu Val Lys Leu
            340                 345                 350

Gly Ile Ser Gln Ile Phe Thr Ser Glu Ala Ser Leu Pro Ser Leu Ala
        355                 360                 365

Arg Gly Gln Gly Val Gln Asn Arg Leu Gln Val Ser Asn Val Ile Gln
    370                 375                 380

Lys Ala Gly Ile Ile Val Asp Glu Lys Gly Ser Thr Ala Tyr Ala Ala
385                 390                 395                 400

Ser Glu Val Ser Leu Val Asn Lys Phe Gly Asp Asp Glu Phe Val Met
                405                 410                 415

Phe Asn Ala Asn His Pro Phe Leu Phe Thr Ile Glu Asp Glu Thr Thr
            420                 425                 430

Gly Ala Ile Leu Phe Thr Gly Lys Val Val Asp Pro Thr Gln
        435                 440                 445
```

<210> SEQ ID NO 50
<211> LENGTH: 1651
<212> TYPE: DNA
<213> ORGANISM: Lutzomyia longipalpis
<220> FEATURE:
<221> NAME/KEY: misc_feature
<222> LOCATION: (1636)..(1636)
<223> OTHER INFORMATION: n is a, c, g, or t

<400> SEQUENCE: 50

```
gtcggagatc gtctgccttg atgatcacat cgtgattgtg agttacaaga gtgaaacttt      60

ttaagtgtgt gtgtcttagc aaagtgattt ccacaatgaa gattattttt ttagccgctt     120

ttctactagc ggatggtatt tgggctgctg aagaaccttc agtggaaatt gtaacaccac     180

aatcagtgcg gagacacgct acgccaaaag cccaggacgc gagggtagga agtgaatccg     240

caacaacagc accaagacca agtgaatcaa tggattactg ggagaatgat gatttcgtcc     300

catttgaggg tccattcaag gatattggag aattcgactg gaacctttcg aagatcgttt     360

ttgaggaaaa caaaggtaat gccatcttgt cgccactctc tgtgaagcta ctaatgagtt     420
```

-continued

```
tgctcttcga ggccagtgcg tcaggtacct tgacccagca ccaactcaga caagccactc    480

ccaccatcgt cacccactat cagtctcgag aattttacaa gaatatcttt gacggtctca    540

agaaaaagag taacgactac acggttcact ttggtacgag aatctacgtg gatcagtttg    600

tgacgcctcg ccagagatat gctgccattt tggagaagca ttatctgact gatctcaaag    660

ttgaggactt ctcgaaggca aaagaaacaa ctcaggcaat caatagttgg gtgtcaaaca    720

tcacaaatga gcacataaag gatctcgtga aggaggaaga tgttcagaat tcagttatgc    780

tcatgcttaa tgcagtctac ttccgcggac tctggcgcaa gcctttcaat cgtacactcc    840

cactgccctt ccacgtgagc gctgatgagt ccaagacgac tgattttatg ctaaccgatg    900

ggctctacta cttctacgag gcaaaggaat tggatgctaa gatcctcaga attccttaca    960

aaggtaaaca atacgcaatg actgtgatct taccaaattc caagagtggc attgatagct   1020

ttgtgcgtca gattaacacg gtcctcctgc acaggattaa gtggttgatg gatgaagtgg   1080

agtgcagggt tattctaccc aagttccact ttgacatgac gaatgagctg aaggaatcgc   1140

tcgtaaagtt gggcatcagt cagattttca catcagaggc atctttgcca tcattagcac   1200

gaggacaggg cgtacagaat cgtctgcagg tgtctaatgt gattcagaag gcgggaataa   1260

ttgtggatga gaagggcagc acagcctatg ctgcgtcaga agtgagccta gtcaacaagt   1320

ttggagatga tgagttcgtc atgttcaacg ctaatcatcc attcctcttt acaattgagg   1380

acgaaaccac cggcgcaatc ctatttacgg gaaaagtcgt cgatcccacg caatagggaa   1440

tgaaaagcat ttcatcgtat acaacttttt ttttaattaa ttattcctca ttgaaggaca   1500

ttaatagagc atcttctcag gaaggcactc ctgacttatt tttactaaat gtgatccttg   1560

gacacataaa aaaaacagct gtactttcta ctttttataa tatacgacca tatttgtgag   1620

gaaaaaaaaa aaaaanaaaa aaaaaaaaaa a                                  1651
```

```
<210> SEQ ID NO 51
<211> LENGTH: 166
<212> TYPE: PRT
<213> ORGANISM: Lutzomyia longipalpis

<400> SEQUENCE: 51

Met Arg Phe Leu Leu Leu Ala Phe Ser Val Ala Leu Val Leu Ser Pro
1               5                   10                  15

Thr Phe Ala Lys Pro Gly Leu Trp Asp Ile Val Thr Gly Ile Asn Asp
            20                  25                  30

Met Val Lys Asn Thr Ala Asn Ala Leu Lys Asn Arg Leu Thr Thr Ser
        35                  40                  45

Val Thr Leu Phe Thr Asn Thr Ile Thr Glu Ala Ile Lys Asn Ala Asn
    50                  55                  60

Ser Ser Val Ser Glu Leu Leu Gln Gln Val Asn Glu Thr Leu Thr Asp
65                  70                  75                  80

Ile Ile Asn Gly Val Gly Gln Val Gln Ser Ala Phe Val Asn Ser Ala
                85                  90                  95

Gly Asn Val Val Val Gln Ile Val Asp Ala Ala Gly Asn Val Leu Glu
            100                 105                 110

Val Val Val Asp Glu Ala Gly Asn Ile Val Glu Val Ala Gly Thr Ala
        115                 120                 125

Leu Glu Thr Ile Ile Pro Leu Pro Gly Val Val Ile Gln Lys Ile Ile
    130                 135                 140

Asp Ala Leu Gln Gly Asn Ala Gly Thr Thr Ser Asp Ser Ala Ser Ser
145                 150                 155                 160
```

Thr Val Pro Gln Gln Ser
165

<210> SEQ ID NO 52
<211> LENGTH: 739
<212> TYPE: DNA
<213> ORGANISM: Lutzomyia longipalpis

<400> SEQUENCE: 52
tcagttaagc agattttcaa gctaaagaaa cttaactaag atgcgattcc ttcttttggc 60
cttctccgtt gctttggtgc tttcaccaac attcgccaaa ccaggtcttt gggacattgt 120
aactggtatt aatgatatgg taaaaaatac tgcgaatgca ctcaaaaatc gtctaacaac 180
ttctgtgaca ttattcacaa ataccatcac cgaagctata aaaaatgcaa attcttctgt 240
ttcggaactc cttcagcaag tcaatgaaac ccttacggat attattaatg gtgtaggaca 300
agtgcagagt gcctttgtga attcagctgg aaatgttgtt gtgcaaattg ttgatgccgc 360
tggaaatgtt ttggaagttg ttgttgatga ggctggaaat atcgtggagg tagctggaac 420
agcattggaa actatcattc cactgcccgg tgtagtgatt cagaagataa ttgatgctct 480
ccaaggaaat gcagggacta catcggattc agcttcatca actgtgcccc aacaatctta 540
actacaaccg caatgatgtt gtctttaacg gagaattttt aaatttgaat atcaaaatcc 600
aagatgaaat attcagattt ttcaatcaat atgatacgaa attttgaaat tatttttccg 660
actaaagcaa tttgtaaaag gaaaaccaaa taaatatttg aaattgtaaa gaaaaaaaaa 720
aaaaaaaaaa aaaaaaaaa 739

<210> SEQ ID NO 53
<211> LENGTH: 109
<212> TYPE: PRT
<213> ORGANISM: Lutzomyia longipalpis

<400> SEQUENCE: 53

Met Val Lys Tyr Ser Cys Leu Val Leu Val Ala Ile Phe Leu Leu Ala
1 5 10 15

Gly Pro Tyr Gly Val Val Gly Ser Cys Glu Asn Asp Leu Thr Glu Ala
20 25 30

Ala Lys Tyr Leu Gln Asp Glu Cys Asn Ala Gly Glu Ile Ala Asp Glu
35 40 45

Phe Leu Pro Phe Ser Glu Glu Glu Val Gly Glu Ala Leu Ser Asp Lys
50 55 60

Pro Glu Asn Val Gln Glu Val Thr Asn Ile Val Arg Gly Cys Phe Glu
65 70 75 80

Ala Glu Gln Ala Lys Glu His Gly Lys Cys Glu Arg Phe Ser Ala Leu
85 90 95

Ser Gln Cys Tyr Ile Glu Lys Asn Leu Cys Gln Phe Phe
100 105

<210> SEQ ID NO 54
<211> LENGTH: 447
<212> TYPE: DNA
<213> ORGANISM: Lutzomyia longipalpis

<400> SEQUENCE: 54
atatcaattt tatcatcatg gtgaagtact cgtgtcttgt tcttgttgca atttttcttc 60
tggccggacc ctacggcgtt gtaggttctt gtgagaatga cctgacagag gccgccaagt 120

-continued atcttcaaga tgaatgcaat gcaggtgaaa ttgcagatga atttctaccc ttctctgaag 180
aagaagtggg tgaagcattg agcgacaaac cagaaaacgt gcaggaagtc accaacatcg 240
tgagaggatg ctttgaagct gaacaagcca aagagcatgg aaaatgtgaa agattttccg 300
ctttgagtca atgctacatt gaaaagaatt tatgtcaatt cttctaaaat attttgaaga 360
aaagttatga atgaaaattt tctgaaattt tgttgcaaaa atatataaat tgcccaatta 420
aaaaaaaaaa aaaaaaaaaa aaaaaaa 447

<210> SEQ ID NO 55
<211> LENGTH: 115
<212> TYPE: PRT
<213> ORGANISM: Lutzomyia longipalpis

<400> SEQUENCE: 55

Met Lys Phe Phe Tyr Leu Ile Phe Ser Ala Ile Phe Phe Leu Ala Asp
1 5 10 15

Pro Ala Leu Val Lys Cys Ser Glu Asp Cys Glu Asn Ile Phe His Asp
20 25 30

Asn Ala Tyr Leu Leu Lys Leu Asp Cys Glu Ala Gly Arg Val Asp Pro
35 40 45

Val Glu Tyr Asp Asp Ile Ser Asp Glu Glu Ile Tyr Glu Ile Thr Val
50 55 60

Asp Val Gly Val Ser Ser Glu Asp Gln Glu Lys Val Ala Lys Ile Ile
65 70 75 80

Arg Glu Cys Ile Ala Gln Val Ser Thr Gln Asp Cys Thr Lys Phe Ser
85 90 95

Glu Ile Tyr Asp Cys Tyr Met Lys Lys Lys Ile Cys Asn Tyr Tyr Pro
100 105 110

Glu Asn Met
115

<210> SEQ ID NO 56
<211> LENGTH: 496
<212> TYPE: DNA
<213> ORGANISM: Lutzomyia longipalpis

<400> SEQUENCE: 56
agtttaattt tcatcatgaa gttcttctac ttgattttct ctgcaatttt ctttctggct 60
gatcctgctt tggtcaagtg ttcagaggat tgtgagaata tttttcatga caatgcgtac 120
ctccttaaat tggattgtga agcaggaagg gttgatcctg ttgaatacga cgatatttcg 180
gatgaagaaa tatatgaaat aacggtcgat gttggagttt catctgagga ccaggagaaa 240
gttgcgaaaa taataaggga gtgcattgca caagtttcaa cgcaagattg cacgaaattt 300
tcagaaattt atgattgtta catgaagaag aaaatctgta attattatcc tgaaaatatg 360
taaaaaaaaa ttatttattt atataaaaaa atataaggat taaaatctct tattgattgt 420
aaaaatggcc taatattgaa gcaaaaatta aagcatgaaa caagaccaaa aaaaaaaaaa 480
aaaaaaaaaa aaaaaa 496

<210> SEQ ID NO 57
<211> LENGTH: 409
<212> TYPE: PRT
<213> ORGANISM: Lutzomyia longipalpis

<400> SEQUENCE: 57

Met His Leu Gln Leu Asn Leu Cys Ala Ile Leu Leu Ser Val Leu Asn

-continued

```
1               5                   10                  15

Gly Ile Gln Gly Ala Pro Lys Ser Ile Asn Ser Lys Ser Cys Ala Ile
            20                  25                  30

Ser Phe Pro Glu Asn Val Thr Ala Lys Lys Glu Pro Val Tyr Leu Lys
        35                  40                  45

Pro Ser Asn Asp Gly Ser Leu Ser Thr Pro Leu Gln Pro Ser Gly Pro
    50                  55                  60

Phe Val Ser Leu Lys Ile Gly Glu Ser Leu Ala Ile Phe Cys Pro Gly
65                  70                  75                  80

Asp Gly Lys Asp Val Glu Thr Ile Thr Cys Asn Thr Asn Phe Asp Leu
                85                  90                  95

Ala Ser Tyr Ser Cys Asn Lys Ser Thr Ser Thr Asp Thr Ile Glu Thr
            100                 105                 110

Glu Glu Val Cys Gly Gly Ser Gly Lys Val Tyr Lys Val Gly Phe Pro
        115                 120                 125

Leu Pro Ser Gly Asn Phe His Ser Ile Tyr Gln Thr Cys Phe Asp Lys
    130                 135                 140

Lys Asn Leu Thr Pro Leu Tyr Ser Ile His Ile Leu Asn Gly Gln Ala
145                 150                 155                 160

Val Gly Tyr His Leu Lys His Thr Arg Gly Ser Phe Arg Thr Asn Gly
                165                 170                 175

Ile Tyr Gly Lys Val Asn Ile Asp Lys Leu Tyr Lys Thr Gln Ile Glu
            180                 185                 190

Lys Phe Asn Lys Leu Phe Gly Pro Lys Gln Thr Phe Phe Arg Arg Pro
        195                 200                 205

Leu Asn Phe Leu Ser Arg Gly His Leu Ser Pro Glu Val Asp Phe Thr
    210                 215                 220

Phe Arg Arg Glu Gln His Ala Thr Glu Met Tyr Ile Asn Thr Ala Pro
225                 230                 235                 240

Gln Tyr Gln Ser Ile Asn Gln Gly Asn Trp Leu Arg Val Glu Asn His
                245                 250                 255

Val Arg Asp Leu Ala Lys Val Leu Gln Lys Asp Ile Thr Val Val Thr
            260                 265                 270

Gly Ile Leu Gly Ile Leu Arg Leu Lys Ser Lys Lys Ile Glu Lys Glu
        275                 280                 285

Ile Tyr Leu Gly Asp Asp Val Ile Ala Val Pro Ala Met Phe Trp Lys
    290                 295                 300

Ala Val Phe Asp Pro Gln Lys Gln Glu Ala Ile Val Phe Val Ser Ser
305                 310                 315                 320

Asn Asn Pro His Val Lys Thr Phe Asn Pro Asn Cys Lys Asp Val Cys
                325                 330                 335

Ala Gln Ala Gly Phe Gly Asn Asp Asn Leu Glu Tyr Phe Ser Asn Tyr
            340                 345                 350

Ser Ile Gly Leu Thr Ile Cys Cys Lys Leu Glu Glu Phe Val Lys Arg
        355                 360                 365

Asn Lys Ile Ile Leu Pro Lys Glu Val Asn Asn Lys Asn Tyr Thr Lys
    370                 375                 380

Lys Leu Leu Lys Phe Pro Lys Thr Arg Asn Lys Glu Gly Asp Lys Lys
385                 390                 395                 400

Val Val Arg Lys Arg Ala Lys Gly Ala
                405
```

<210> SEQ ID NO 58

<211> LENGTH: 1281
<212> TYPE: DNA
<213> ORGANISM: Lutzomyia longipalpis

<400> SEQUENCE: 58
tcaatctaac aatgcacctg caattgaatt tgtgcgctat tctcctttcg gtactaaatg 60
gaattcaggg cgctcccaaa agtattaatt caaaatcctg cgcaatctcc tttccggaga 120
atgtaacggc taagaaggag ccagtgtact tgaaaccatc aaatgatggc tcattgagta 180 ccccccctaca gccaagtggg ccatttgtaa gtctcaaaat tggagaatct cttgcaatct 240
tctgtccagg tgatggaaag gacgtagaga caattacgtg caatacaaat ttcgatttag 300
cttcatattc gtgcaacaag agcacatcaa cggataccat tgaaacggaa gaagtttgcg 360
gaggaagtgg aaaagtgtac aaagttggtt ttccgctgcc ctctgggaat ttccattcaa 420
tctaccaaac gtgttttgat aagaaaaatc tcacacctct ctactcaatt cacattctca 480
atggtcaagc tgttggatat caccttaagc acacaagagg aagctttcgt accaatggta 540
tctacgggaa agtcaacatt gataaactct acaagacgca aattgagaaa ttcaacaaac 600
ttttcggccc taaacaaaca tttttccgta gacccctcaa ttttctatca cgtggacact 660
taagccccga agtggacttt acattccgta gggaacaaca tgcaacggaa atgtacatta 720
acacagcacc acagtaccaa tcaattaatc aaggaaattg gctacgtgtt gaaaatcacg 780
tgagggatct cgcaaaagtt ctgcagaagg acataacagt cgttacggga attttgggga 840
tacttcggtt gaagagtaag aaaatagaga aagaaatcta tttaggagat gacgtaattg 900
ccgtaccagc aatgttctgg aaggctgttt ttgaccctca aaaacaagaa gcaattgtct 960
ttgtttcctc aaataatccc cacgtgaaga cctttaatcc caactgcaag gatgtatgcg 1020
ctcaagctgg atttgggaat gataatcttg aatatttctc caattattct attggtctga 1080
ctatttgttg caaacttgag gaatttgtta aaagaaataa aataattcta cccaaagaag 1140
taaataacaa aaactacacc aaaaaactcc ttaagtttcc taaaacaaga aacaaggagg 1200
gagataagaa ggtggtacgt aagcgcgcca aaggagcata aatattaaac gaaaaaaaaa 1260
aaaaaaaaaa aaaaaaaaaa a 1281

<210> SEQ ID NO 59
<211> LENGTH: 160
<212> TYPE: PRT
<213> ORGANISM: Lutzomyia longipalpis

<400> SEQUENCE: 59

Met Asn Leu His Leu Ala Ile Ile Leu Phe Val Ser Tyr Phe Thr Leu
1 5 10 15

Ile Thr Ala Thr Asp Leu Ile Glu Lys Glu Leu Ser Asp Cys Lys Lys
20 25 30

Ile Phe Ile Ser Lys Ala Glu Leu Thr Trp Phe Gln Ala Leu Asp Phe
35 40 45

Cys Thr Glu Gln Asn Leu Thr Leu Leu Ser Ile Lys Ser Ala Arg Glu
50 55 60

Asn Asp Glu Val Thr Lys Ala Val Arg Ala Glu Val His Leu Pro Asp
65 70 75 80

Thr Lys Lys Ser His Ile Trp Leu Gly Gly Ile Arg Tyr Asp Gln Asp
85 90 95

Lys Asp Phe Arg Trp Ile Ser Asp Gly Thr Thr Val Thr Lys Thr Val
100 105 110

-continued

```
Tyr Ile Asn Trp Tyr Gln Gly Glu Pro Asn Gly Gly Arg Tyr Gln Lys
        115                 120                 125

Glu Phe Cys Met Glu Leu Tyr Phe Lys Thr Pro Ala Gly Gln Trp Asn
    130                 135                 140

Asp Asp Ile Cys Thr Ala Lys His His Phe Ile Cys Gln Glu Lys Lys
145                 150                 155                 160


<210> SEQ ID NO 60
<211> LENGTH: 671
<212> TYPE: DNA
<213> ORGANISM: Lutzomyia longipalpis

<400> SEQUENCE: 60

gttctacgat aaaattttct tttcaaactt ttcttttaaa gaaaaatctt caaaaagtta      60

aaatgaattt gcaccttgcg attatcctct ttgtgagtta cttcacactg atcactgcta     120

cggatctaat tgaaaaggaa ctttctgatt gcaaaaagat cttcatctcc aaggctgagc     180

taacttggtt ccaagctctc gatttctgta ccgaacaaaa cctaactttg ctctcaatta     240

aatccgcccg ggaaaatgat gaggtgacta aagcagttcg agctgaggtt catcttccag     300

acacaaagaa gtctcacatt tggctcggag gtattcgtta tgatcaagac aaggatttcc     360

gttggataag cgatggaaca actgttacga agacagtcta catcaattgg taccaaggag     420

aaccaaatgg tgggaggtac caaaaggaat tttgtatgga attgtacttt aaaactccag     480

ctggtcaatg gaatgatgat atttgtacag caaagcatca ttttatatgt caggagaaaa     540

aataaattga attgttcatg tgtctttggc ggtgcgaagg tataattcag gttgacgaca     600

taaattgatt tttctttcat taagaaaata aaggcttgaa tttataaaaa aaaaaaaaaa     660

aaaaaaaaaa a                                                          671


<210> SEQ ID NO 61
<211> LENGTH: 160
<212> TYPE: PRT
<213> ORGANISM: Lutzomyia longipalpis

<400> SEQUENCE: 61

Met Asn Leu Pro Leu Ala Ile Ile Leu Phe Val Ser Tyr Phe Thr Leu
1               5                   10                  15

Ile Thr Ala Ala Asp Leu Thr Glu Lys Glu Leu Ser Asp Gly Lys Lys
            20                  25                  30

Ile Phe Ile Ser Lys Ala Glu Leu Ser Trp Phe Asp Ala Leu Asp Ala
        35                  40                  45

Cys Thr Glu Lys Asp Leu Thr Leu Leu Thr Ile Lys Ser Ala Arg Glu
    50                  55                  60

Asn Glu Glu Val Thr Lys Ala Val Arg Ala Glu Val His Leu Pro Asp
65                  70                  75                  80

Thr Lys Lys Ser His Ile Trp Leu Gly Gly Ile Arg Tyr Asp Gln Asp
                85                  90                  95

Lys Asp Phe Arg Trp Ile Ser Asp Gly Thr Thr Val Thr Lys Thr Val
            100                 105                 110

Tyr Ile Asn Trp Tyr Gln Gly Glu Pro Asn Gly Gly Arg Tyr Gln Lys
        115                 120                 125

Glu Phe Cys Met Glu Leu Tyr Phe Lys Thr Pro Ala Gly Gln Trp Asn
    130                 135                 140

Asp Asp Ile Cys Thr Ala Lys His His Phe Ile Cys Gln Glu Lys Lys
145                 150                 155                 160
```

<210> SEQ ID NO 62
<211> LENGTH: 672
<212> TYPE: DNA
<213> ORGANISM: Lutzomyia longipalpis

<400> SEQUENCE: 62
gttctacgat aaaatttct tttcaaactt ttcttttaaa gaaaaatctt caaaaagtta 60
aaatgaattt gccccttgcg attatcctct ttgtgagtta cttcacactg atcactgctg 120
cggatctaac tgaaaaggaa ctttctgatg gcaaaaagat cttcatctcc aaggctgagc 180
taagttggtt cgatgctctc gatgcctgta ccgaaaaaga cctaactttg ctcacaatta 240
aatccgcccg ggaaaatgag gaagtgacta aagcagttcg agctgaggtt catcttccag 300
acacaaagaa gtctcacatt tggctcggag gtattcgtta tgatcaagac aaggatttcc 360
gttggataag cgatggaaca actgttacga agacagtcta catcaattgg taccaaggag 420
aaccaaatgg tgggaggtac caaaaggaat tttgtatgga attgtacttt aaaactccag 480
ctggtcaatg gaatgatgat atttgtacag caaagcatca ttttatatgt caggagaaaa 540
aataaattga attgttcatg tgtctttggc ggtgcgaagg tataattcag gttgacgaca 600
taaattgatt tttctttcat taagaaaata aaggcttgaa tttagcaaaa aaaaaaaaaa 660
aaaaaaaaaa aa 672

<210> SEQ ID NO 63
<211> LENGTH: 399
<212> TYPE: PRT
<213> ORGANISM: Lutzomyia longipalpis

<400> SEQUENCE: 63

Met Lys Val Phe Phe Ser Ile Phe Thr Leu Val Leu Phe Gln Gly Thr
1 5 10 15

Leu Gly Ala Asp Thr Gln Gly Tyr Lys Trp Lys Gln Leu Leu Tyr Asn
20 25 30

Asn Val Thr Pro Gly Ser Tyr Asn Pro Asp Asn Met Ile Ser Thr Ala
35 40 45

Phe Ala Tyr Asp Ala Glu Gly Glu Lys Leu Phe Leu Ala Val Pro Arg
50 55 60

Lys Leu Pro Arg Val Pro Tyr Thr Leu Ala Glu Val Asp Thr Lys Asn
65 70 75 80

Ser Leu Gly Val Lys Gly Lys His Ser Pro Leu Leu Asn Lys Phe Ser
85 90 95

Gly His Lys Thr Gly Lys Glu Leu Thr Ser Ile Tyr Gln Pro Val Ile
100 105 110

Asp Asp Cys Arg Arg Leu Trp Val Val Asp Ile Gly Ser Val Glu Tyr
115 120 125

Arg Ser Arg Gly Ala Lys Asp Tyr Pro Ser His Arg Pro Ala Ile Val
130 135 140

Ala Tyr Asp Leu Lys Gln Pro Asn Tyr Pro Glu Val Val Arg Tyr Tyr
145 150 155 160

Phe Pro Thr Arg Leu Val Glu Lys Pro Thr Tyr Phe Gly Gly Phe Ala
165 170 175

Val Asp Val Ala Asn Pro Lys Gly Asp Cys Ser Glu Thr Phe Val Tyr
180 185 190

Ile Thr Asn Phe Leu Arg Gly Ala Leu Phe Ile Tyr Asp His Lys Lys
195 200 205

```
Gln Asp Ser Trp Asn Val Thr His Pro Thr Phe Lys Ala Glu Arg Pro
    210                 215                 220

Thr Lys Phe Asp Tyr Gly Gly Lys Glu Tyr Glu Phe Lys Ala Gly Ile
225                 230                 235                 240

Phe Gly Ile Thr Leu Gly Asp Arg Asp Ser Glu Gly Asn Arg Pro Ala
                245                 250                 255

Tyr Tyr Leu Ala Gly Ser Ala Ile Lys Val Tyr Ser Val Asn Thr Lys
            260                 265                 270

Glu Leu Lys Gln Lys Gly Gly Lys Leu Asn Pro Glu Leu Leu Gly Asn
        275                 280                 285

Arg Gly Lys Tyr Asn Asp Ala Ile Ala Leu Ala Tyr Asp Pro Lys Thr
    290                 295                 300

Lys Val Ile Phe Phe Ala Glu Ala Asn Thr Lys Gln Val Ser Cys Trp
305                 310                 315                 320

Asn Thr Gln Lys Met Pro Leu Arg Met Lys Asn Thr Asp Val Val Tyr
                325                 330                 335

Thr Ser Ser Arg Phe Val Phe Gly Thr Asp Ile Ser Val Asp Ser Lys
            340                 345                 350

Gly Gly Leu Trp Phe Met Ser Asn Gly Phe Pro Pro Ile Arg Lys Ser
        355                 360                 365

Glu Lys Phe Lys Tyr Asp Phe Pro Arg Tyr Arg Leu Met Arg Ile Met
    370                 375                 380

Asp Thr Gln Glu Ala Ile Ala Gly Thr Ala Cys Asp Met Asn Ala
385                 390                 395
```

<210> SEQ ID NO 64
<211> LENGTH: 1429
<212> TYPE: DNA
<213> ORGANISM: Lutzomyia longipalpis

<400> SEQUENCE: 64

```
ttgaattgaa gcagcagcaa tgaaagtgtt tttctcaatt tttacgctcg tcctcttcca     60

agggaccctt ggagcggata ctcaaggata taaatggaag caattgctct acaataatgt    120

tacaccagga tcctacaatc cggataatat gatcagtacg gcttttgcct acgatgctga    180

gggtgaaaaa ctcttcctag ctgtcccaag gaagttaccc agagttccgt atacattggc    240

ggaagtggat acaaagaata gtcttggtgt taagggaaaa cattcaccgt tacttaacaa    300

attcagtggg cacaaaactg ggaaggaact aacatcaatc tatcagccag ttattgatga    360

ttgtcgtcgc ctttgggtgg ttgatattgg ttccgtggaa tatcgctcaa gaggtgccaa    420

agactacccg agtcatcgtc ctgcaattgt tgcgtacgac ctaaagcaac caaactaccc    480

cgaagttgtt cgatactatt tccccacaag attagtggag aagccaacat atttcggtgg    540

atttgccgtt gatgttgcaa acccaaaggg ggattgtagt gaaacttttg tctacattac    600

aaacttcctc aggggagctc tctttatata cgatcataag aagcaggatt cgtggaatgt    660

aactcatccc accttcaaag cagaacgacc cactaaattt gattacggcg gaaaggaata    720

tgaattcaaa gccggaattt tcggaattac tctcggagat cgagacagtg aaggcaatcg    780

tccagcttac tacttagccg gaagtgccat caaagtctac agcgtcaaca cgaaagaact    840

taagcagaag ggtggaaagc tgaatccgga gcttcttgga aaccgcggga agtacaacga    900

tgccattgcc ctagcttacg atcccaaaac taaagttatc ttctttgctg aggccaacac    960

aaagcaagta tcctgctgga acacacagaa aatgccactg aggatgaaga ataccgacgt   1020

agtctacact agttctcgct ttgtctttgg aacggacatt tcggttgata gcaagggcgg   1080
```

```
cctctggttc atgtctaacg gctttccgcc tataaggaaa tcagaaaaat tcaaatatga   1140

cttcccacgc taccgtctaa tgaggatcat ggacacacag gaagcaattg ccggaactgc   1200

ttgcgatatg aatgcataaa agttaatttt caacccaaga agaagaccta aagaggcttt   1260

tccaggcttt gatgcaggag aggtggttat caacgcaaaa tcagctattg ttgtatgagg   1320

aggagaaatt attgattctg aattctataa aaaaaattta atttgtgaaa tatttggcaa   1380

taataaatta attgaattac aaaaaaaaaa aaaaaaaaaa aaaaaaaaa              1429


<210> SEQ ID NO 65
<211> LENGTH: 170
<212> TYPE: PRT
<213> ORGANISM: Lutzomyia longipalpis

<400> SEQUENCE: 65

Met Gln Ser Lys Ile Leu Ser Phe Val Leu Phe Thr Leu Ser Leu Gly
1               5                   10                  15

Tyr Val Leu Gly Glu Thr Cys Ser Asn Ala Lys Val Lys Gly Ala Thr
            20                  25                  30

Ser Tyr Ser Thr Thr Asp Ala Thr Ile Val Ser Gln Ile Ala Phe Val
        35                  40                  45

Thr Glu Phe Ser Leu Glu Cys Ser Asn Pro Gly Ser Glu Lys Ile Ser
    50                  55                  60

Leu Phe Ala Glu Val Asp Gly Lys Ile Thr Pro Val Ala Met Ile Gly
65                  70                  75                  80

Asp Thr Thr Tyr Gln Val Ser Trp Asn Glu Glu Val Asn Lys Ala Arg
                85                  90                  95

Ser Gly Asp Tyr Ser Val Lys Leu Tyr Asp Glu Glu Gly Tyr Gly Ala
            100                 105                 110

Val Arg Lys Ala Gln Arg Ser Gly Glu Glu Asn Lys Val Lys Pro Leu
        115                 120                 125

Ala Thr Val Val Val Arg His Pro Gly Thr Tyr Thr Gly Pro Trp Phe
    130                 135                 140

Asn Ser Glu Ile Leu Ala Ala Gly Leu Ile Ala Val Val Ala Tyr Phe
145                 150                 155                 160

Ala Phe Ser Thr Arg Ser Lys Ile Leu Ser
                165                 170


<210> SEQ ID NO 66
<211> LENGTH: 712
<212> TYPE: DNA
<213> ORGANISM: Lutzomyia longipalpis

<400> SEQUENCE: 66

tctctttggt taacattgtg aagttatcgg acgtggccgg tttctatttc ttttgcaaaa     60

atgcagtcaa aaattctttc tttcgtcctt ttcaccttat ccttgggcta tgttttgggt    120

gaaacatgct caaatgctaa ggttaaggga gctacctctt attccacaac ggatgccaca    180

attgtaagcc aaattgcctt tgtgactgaa ttctccttgg aatgctcaaa tcctggatcc    240

gagaaaatct ccctatttgc tgaagtcgat ggcaaaatta ctcctgttgc catgatcggg    300

gataccacct accaggtgag ctggaatgaa gaggttaata aggctagaag tggtgactac    360

agtgtgaagc tgtacgatga agaaggatac ggagcagtac gcaaagctca gagatcaggt    420

gaagagaaca aggtcaaacc actagcaacc gttgttgttc gacatccagg aacatacact    480

ggaccatggt tcaattccga aatcctcgca gctggtctca ttgctgttgt tgcctacttt    540
```

```
gctttctcaa cgcgaagcaa aattctttcc taaagagacg cagcatgaaa tttcacaaaa    600

aaataaaaac aaattcaagt catcaaccat gtctctttgg cactcagact gtttctgtga    660

aatacaaact attatttaac aaaaaaaaaa aaaaaaaaaa aaaaaaaaaa aa            712


<210> SEQ ID NO 67
<211> LENGTH: 73
<212> TYPE: PRT
<213> ORGANISM: Lutzomyia longipalpis

<400> SEQUENCE: 67

Met Val Ser Ile Leu Leu Ile Ser Leu Ile Leu Asn Leu Leu Val Phe
1               5                   10                  15

Tyr Ala Lys Ala Arg Pro Leu Glu Asp Ile Ser Ser Asp Leu Ser Pro
            20                  25                  30

Asp Tyr Tyr Ile Thr Glu Gly Tyr Asp Gly Val Lys Glu Lys Arg Glu
        35                  40                  45

Ile Glu Leu Val Pro Val Thr Phe Gly Ile Phe Asn Ile His Thr Thr
    50                  55                  60

Pro Ala Pro Arg Ile Thr Phe Glu Trp
65                  70


<210> SEQ ID NO 68
<211> LENGTH: 379
<212> TYPE: DNA
<213> ORGANISM: Lutzomyia longipalpis

<400> SEQUENCE: 68

attcccacaa gaagctgcta aaatggtgtc aattctgtta atctccttga ttcttaattt     60

gttggttttc tatgctaaag ctagaccact agaagacatc tcgtcagatc tttcccctga    120

ttattacatc actgaaggct atgacggtgt gaaggagaag agagagatcg aacttgtacc    180

tgtgacattt ggaatattta atatacatac aacacctgct cccagaatta cctttgaatg    240

gtaaaaaatc caagaagaat ttatgatttt attcttcctt ccattgggat ggattgtaag    300

tcagcataaa acgccgttaa aaatgaattt ttaataaaaa aaaattattc caaaaaaaaa    360

aaaaaaaaaa aaaaaaaaa                                                 379


<210> SEQ ID NO 69
<211> LENGTH: 76
<212> TYPE: PRT
<213> ORGANISM: Lutzomyia longipalpis

<400> SEQUENCE: 69

Met Lys Leu Phe Cys Leu Ile Phe Val Val Phe Val Ala Leu Glu Val
1               5                   10                  15

Cys Ile Glu Thr Val Lys Ala Met Glu Ala Thr Glu Glu Ile Ser Val
            20                  25                  30

Lys Leu Gln Asp Asp Ala Asn Glu Pro Asp Asp Ser Leu Asp Leu Asp
        35                  40                  45

Glu Gly Leu Pro Asp Ala Phe Asp Glu Asp Tyr Asn Asn Gln Ala Glu
    50                  55                  60

Tyr Lys Pro Asn Pro Arg Gly Asp Tyr Arg Arg Arg
65                  70                  75


<210> SEQ ID NO 70
<211> LENGTH: 526
<212> TYPE: DNA
```

-continued

```
<213> ORGANISM: Lutzomyia longipalpis

<400> SEQUENCE: 70

cactattcat tggaagattt attaacttca agatgaaatt attttgttta atttttgttg      60

tgtttgttgc tttagaagtc tgtatagaga ccgtgaaagc tatggaagca acggaggaga     120

tatctgtaaa attgcaagat gatgcgaatg aacctgatga ctctctggat ttagacgaag     180

gtcttcctga tgcattcgat gaggactata ataatcaggc tgagtacaag ccgaatccta     240

gaggggacta cagaagacga taattaatat aaattcagga aaacactcta aaaatttcca     300

attgactcta ctttaaacga tttaatacct acctacacta aataccatat gcaataatta     360

tgttttaatt atttagtgca agatctacta gtttcagttc atattttggg actttcccgc     420

ctttctctcg atggaaaaat gattttacgg attcttaatt ttcattgtac agagttaata     480

aaacaattga aagcaattaa aaaaaaaaaa aaaaaaaaaa aaaaaa                    526


<210> SEQ ID NO 71
<211> LENGTH: 22
<212> TYPE: DNA
<213> ORGANISM: Artificial sequence
<220> FEATURE:
<223> OTHER INFORMATION: Oligonucleotide primer

<400> SEQUENCE: 71

aagtactcta gcaattgtga gc                                               22


<210> SEQ ID NO 72
<211> LENGTH: 22
<212> TYPE: DNA
<213> ORGANISM: Artificial sequence
<220> FEATURE:
<223> OTHER INFORMATION: Oligonucleotide primer

<400> SEQUENCE: 72

ctcttcgcta ttacgccagc tg                                               22


<210> SEQ ID NO 73
<211> LENGTH: 24
<212> TYPE: DNA
<213> ORGANISM: Artificial sequence
<220> FEATURE:
<223> OTHER INFORMATION: Oligonucleotide primer

<400> SEQUENCE: 73

tctcgggaag cgcgccattg tgtt                                             24
```

*LUTZOMYIA LONGIPALPIS* POLYPEPTIDES AND METHODS OF USE

CROSS REFERENCE TO RELATED APPLICATIONS

This is a divisional of U.S. patent application Ser. No. 14/802,168, filed Jul. 17, 2015, issued as U.S. Pat. No. 9,382,302 on Jul. 5, 2016, which is a divisional of U.S. patent application Ser. No. 14/097,991, filed Dec. 5, 2013, issued as U.S. Pat. No. 9,120,867 on Sep. 1, 2015, which is a divisional of U.S. patent application Ser. No. 12/350,179, filed Jan. 7, 2009, issued as U.S. Pat. No. 8,628,780 on Jan. 14, 2014, which is a divisional of U.S. patent application Ser. No. 10/533,811, filed Apr. 29, 2005, issued as U.S. Pat. No. 7,485,306 on Feb. 3, 2009, which is the § 371 U.S. National Stage of International Application No. PCT/US2003/034453, filed Oct. 29, 2003, published in English under PCT Article 21(2), which in turn claims the benefit of U.S. Provisional Application No. 60/422,303, filed Oct. 29, 2002. All of the above-listed applications are incorporated by reference in their entirety.

FIELD

The disclosure relates to proteins substantially purified from *Lutzomyia longipalpis* (*Lu. longipalpis*) sand fly salivary glands, or recombinant vectors expressing these proteins, and to an immune response produced to these proteins. This disclosure also relates to the production of an immune response that affects survival of *Leishmania.*

BACKGROUND

*Leishmaniasis* is a group of diseases caused by protozoa of the genus *Leishmania* and affect many millions of people worldwide. In humans, infection with the parasite manifests either as a cutaneous disease caused mainly by *L. major, L. tropica*, and *L. mexicana*; as a mucocutaneous disease caused mainly by *L. brasiliensis*; or as a visceral disease caused mainly by *L. donovani* and *L. chagasi*. In canids, *Leishmania* infections manifest as a visceral disease that can result in high death rates.

All leishmanial diseases are transmitted to their vertebrate hosts by phlebotomine sand flies, which acquire the pathogen by feeding on infected hosts and transmit them by regurgitating the parasite at the site of a subsequent blood meal (Killick-Kendrick, Biology of *Leishmania* in phlebotomine sand flies. In Biology of the Kinetoplastida. W. Lumsden and D. Evans, editors. Academic Press, New York. 395, 1979).

While obtaining a blood meal, sand flies salivate into the host's skin. This saliva contains anticlotting, antiplatelet, and vasodilatory compounds that increase the hemorrhagic pool where sand flies feed (Ribeiro et al., *Comp. Biochem. Physiol.* 4:683, 1986; Charlab et al., *Proc. Natl. Acad. Sci. USA.* 26:15155, 1999). Some of these components are additionally immunomodulatory. For example, the New World sand fly *Lutzomyia longipalpis* contains the 6.5 kDa peptide, maxadilan, which is the most potent vasodilator known (Lerner et al., *J. Biol. Chem.* 17:11234, 1991). Maxadilan additionally has immunosuppressive activities of its own (Qureshi et al., *Am. J. Trop. Med. Hyg.* 6:665, 1996), as do many persistent vasodilators such as prostaglandin E2 (Makoul et al., *J. Immunol.* 134:2645, 1985; Santoli and Zurier, *J. Immunol.* 143:1303, 1989; Stockman and Mumford, *Exp. Hematol.* 2:65, 1974) and calcitonin gene-related peptide (Nong et al., *J. Immunol.* 1:45, 1989). Old World sand flies do not have maxadilan but instead use AMP and adenosine as vasodilators (Ribeiro et al., *J. Exp. Biol.* 11:1551, 1999). Adenosine is also an immunomodulatory component, promoting the production of IL-10 and suppressing TNF-α and IL-12 in mice (Hasko et al., *J. Immunol.* 10:4634, 1996; Webster, *Asian Pac. J. Allergy Immunol.* 2:311, 1984; Hasko et al., *FASEB J.* 14:2065, 2000). Despite what is known about the role of sand fly saliva and disease transmission, much remains unknown, and an effective vaccine does not exist. Thus, there is a need for agents that can be used to induce an immune response to the organisms that cause leishmaniasis.

SUMMARY

The present disclosure relates to salivary proteins from sand fly vectors of *Lutzomyia longipalpis* (*Lu. longipalpis*) and the nucleic acids that encode these proteins. Methods of producing an immune response in a subject are also disclosed.

Substantially purified salivary *Lu. longipalpis* polypeptides are disclosed herein. Also disclosed are polynucleotides encoding the *Lu. longipalpis* polypeptides.

Methods are disclosed for inducing an immune response using a therapeutically effective amount of a substantially purified salivary *Lu. longipalpis* polypeptide as disclosed herein, or the polynucleotide encoding a *Lu. longipalpis* polypeptides disclosed herein.

In another embodiment methods are disclosed herein for inhibiting the symptoms of a *Leishmania* infection or for preventing a *Leishmania* infection in a subject. The methods include administering to the subject a therapeutically effective amount of a *Lu. longipalpis* polypeptide, or a polynucleotide encoding a *Lu. longipalpis* polypeptide. In two non-limiting examples, more than one *Lu. longipalpis* polypeptide can be administered, or at least one *Lu. longipalpis* polypeptide in conjunction with a *P. ariasi* or *P. perniciosus* polypeptide.

Also disclosed herein are methods of diagnosing *Leishmania* infection in a subject. The methods include contacting a solid substrate comprising at least three, six, or ten *Lu. longipalpis* polypeptides, or an immunogenic fragment thereof, contacting the solid substrate with a sample obtained from the subject and detecting binding of a component of the sample to at least one polypeptide on the solid substrate. Detection of binding of the component to the substrate indicates that the subject is infected with *Leishmania.*

Pharmaceutical compositions are disclosed including a pharmaceutically acceptable carrier and a *Lu. longipalpis* polypeptide.

The foregoing and other features and advantages will become more apparent from the following detailed description of several embodiments, which proceeds with reference to the accompanying figures.

BRIEF DESCRIPTION OF THE FIGURES

1A is a bar graph of anti-saliva IgG levels in individuals who converted from $S^- \rightarrow S^+$ and those who converted from $DTH^-$ to $DTH^+$. FIG. 1B is a bar graph of anti-saliva IgE levels in the individuals described in FIG. 1A. FIG. 1C is a bar graph of anti-saliva IgG1 levels in the individuals described in FIG. 1A. FIG. 1D is a bar graph of anti-saliva IgG4 levels in the individuals described in FIG. 1A. The non-parametric paired Wilcoxon test was used to compare levels of anti-*Lu. longipalpis* saliva antibodies at time 0 and after 6 months. P value<0.05 was established as the significance level.

FIGS. 2A and 2B are digital images of a Western blot of *Lu. longipalpis* salivary proteins reacted to human sera of individuals who converted from $S^- \rightarrow S^+$ to *Leishmania* (lanes 1-6) or from $DTH^- \rightarrow DTH^+$ to *Leishmania* (lanes 7-14). Symbols: –, time 0; +, 6 months. FIG. 2C is a bar graph of the frequency of salivary proteins recognized by sera of 13 individuals who converted from $DTH^- \rightarrow DTH^+$ to *Leishmania*. The x-axis shows the different *Lu. longipalpis* salivary proteins (labeled by the approximate molecular weight) recognized by Western blot analysis, while the y-axis indicates the number of human sera recognizing a particular salivary protein.

SEQUENCE LISTING

Figures 1A, 1B, 1C, 1D:
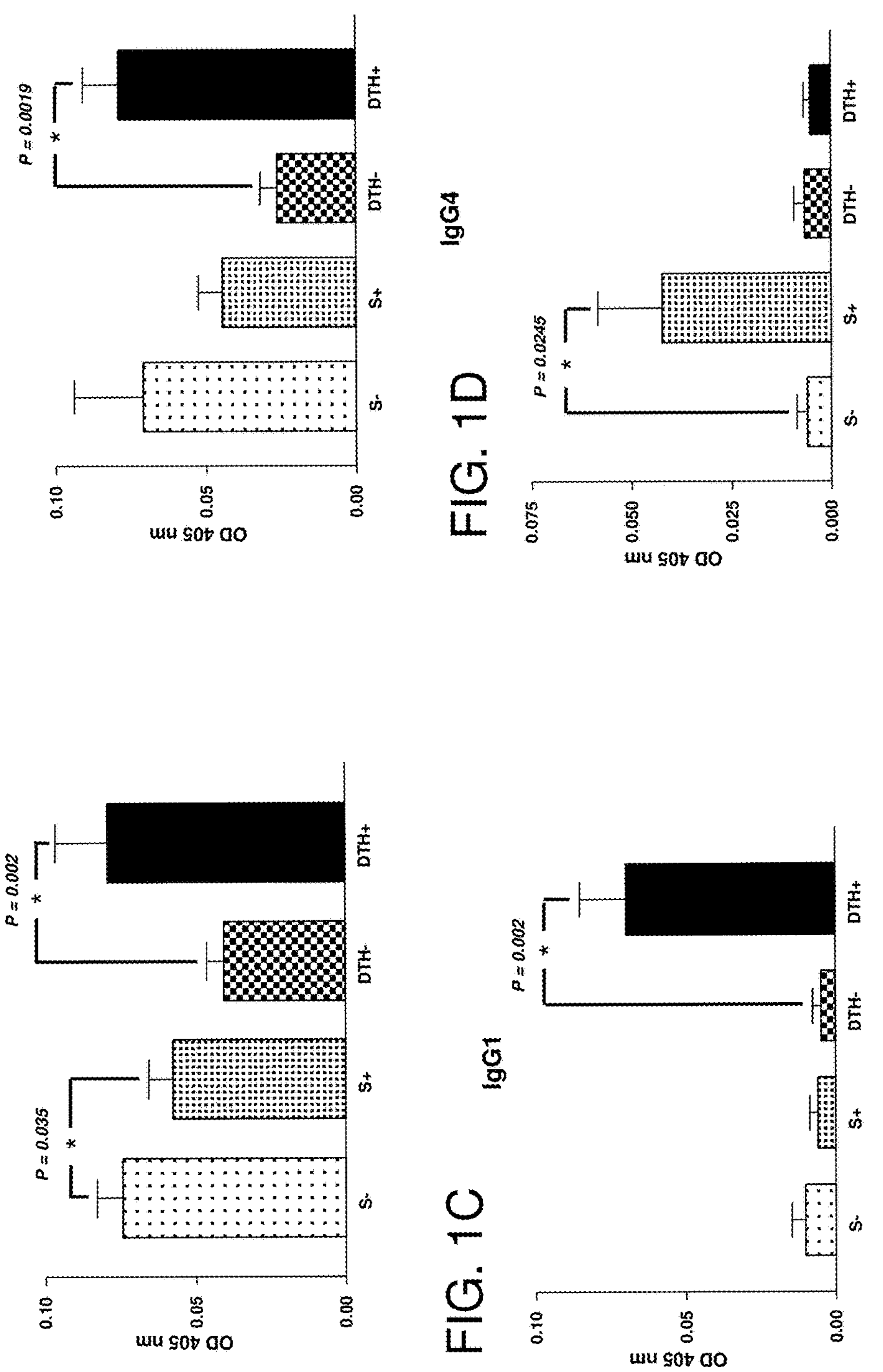
FIGS. 1A-1D are a set of bar graphs showing the levels of antibodies against *Lutzomyia longipalpis* (*Lu. longipalpis*) saliva in sera of individuals. Human sera were obtained at time 0 (negative anti-*Leishmania* serology ($S^-$) or negative DTH ($DTH^-$)) and 6 months later (positive anti-*Leishmania* serology ($S^+$) or positive anti-*Leishmania* DTH ($DTH^+$)). ELISA was performed with these sera using salivary gland sonicate of the sand fly *Lu. longipalpis*. FIG.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on May 26, 2016, 111 KB, which is incorporated by reference herein. In the accompanying sequence listing:

SEQ ID NO: 1 is the amino acid sequence of LJL34.
SEQ ID NO: 2 is the nucleic acid sequence of LJL34.
SEQ ID NO: 3 is the amino acid sequence of LJL18.
SEQ ID NO: 4 is the nucleic acid sequence of LJL18.
SEQ ID NO: 5 is the amino acid sequence of LJS193.
SEQ ID NO: 6 is the nucleic acid sequence of LJS193.
SEQ ID NO: 7 is the amino acid sequence of LJS201.
SEQ ID NO: 8 is the nucleic acid sequence of LJS201.
SEQ ID NO: 9 is the amino acid sequence of LJL13.
SEQ ID NO: 10 is the nucleic acid sequence of LJL13.
SEQ ID NO: 11 is the amino acid sequence of LJL23.
SEQ ID NO: 12 is the nucleic acid sequence of LJL23.
SEQ ID NO: 13 is the amino acid sequence of LJM10.
SEQ ID NO: 14 is the nucleic acid sequence of LJM10.
SEQ ID NO: 15 is the amino acid sequence of LJL143.
SEQ ID NO: 16 is the nucleic acid sequence of LJL143.
SEQ ID NO: 17 is the amino acid sequence of LJS142.
SEQ ID NO: 18 is the nucleic acid sequence of LJS142.
SEQ ID NO: 19 is the amino acid sequence of LJL17.
SEQ ID NO: 20 is the nucleic acid sequence of LJL17.
SEQ ID NO: 21 is the amino acid sequence of LJM06.
SEQ ID NO: 22 is the nucleic acid sequence of LJM06.
SEQ ID NO: 23 is the amino acid sequence of LJM17.
SEQ ID NO: 24 is the nucleic acid sequence of LJM17.
SEQ ID NO: 25 is the amino acid sequence of LJL04.
SEQ ID NO: 26 is the nucleic acid sequence of LJL04.
SEQ ID NO: 27 is the amino acid sequence of LJM114.
SEQ ID NO: 28 is the nucleic acid sequence of LJM114.
SEQ ID NO: 29 is the amino acid sequence of LJM111.
SEQ ID NO: 30 is the nucleic acid sequence of LJM111.
SEQ ID NO: 31 is the amino acid sequence of LJM78.
SEQ ID NO: 32 is the nucleic acid sequence of LJM78.
SEQ ID NO: 33 is the amino acid sequence of LJS238.
SEQ ID NO: 34 is the nucleic acid sequence of LJS238.
SEQ ID NO: 35 is the amino acid sequence of LJS169.
SEQ ID NO: 36 is the nucleic acid sequence of LJS169.
SEQ ID NO: 37 is the amino acid sequence of LJL11.
SEQ ID NO: 38 is the nucleic acid sequence of LJL11.
SEQ ID NO: 39 is the amino acid sequence of LJL08.
SEQ ID NO: 40 is the nucleic acid sequence of LJL08.
SEQ ID NO: 41 is the amino acid sequence of LJS105.
SEQ ID NO: 42 is the nucleic acid sequence of LJS105.
SEQ ID NO: 43 is the amino acid sequence of LJL09.
SEQ ID NO: 44 is the nucleic acid sequence of LJL09.
SEQ ID NO: 45 is the amino acid sequence of LJL38.
SEQ ID NO: 46 is the nucleic acid sequence of LJL38.
SEQ ID NO: 47 is the amino acid sequence of LJM04.
SEQ ID NO: 48 is the nucleic acid sequence of LJM04.
SEQ ID NO: 49 is the amino acid sequence of LJM26.
SEQ ID NO: 50 is the nucleic acid sequence of LJM26.
SEQ ID NO: 51 is the amino acid sequence of LJS03.
SEQ ID NO: 52 is the nucleic acid sequence of LJS03.
SEQ ID NO: 53 is the amino acid sequence of LJS192.
SEQ ID NO: 54 is the nucleic acid sequence of LJS192.
SEQ ID NO: 55 is the amino acid sequence of LJM19.
SEQ ID NO: 56 is the nucleic acid sequence of LJM19.
SEQ ID NO: 57 is the amino acid sequence of LJL138.
SEQ ID NO: 58 is the nucleic acid sequence of LJL138.
SEQ ID NO: 59 is the amino acid sequence of LJL15.
SEQ ID NO: 60 is the nucleic acid sequence of LJL15.
SEQ ID NO: 61 is the amino acid sequence of LJL91.
SEQ ID NO: 62 is the nucleic acid sequence of LJL91.
SEQ ID NO: 63 is the amino acid sequence of LJM11.
SEQ ID NO: 64 is the nucleic acid sequence of LJM11.
SEQ ID NO: 65 is the amino acid sequence of LJS138.
SEQ ID NO: 66 is the nucleic acid sequence of LJS138.
SEQ ID NO: 67 is the amino acid sequence of LJL124.
SEQ ID NO: 68 is the nucleic acid sequence of LJL124.
SEQ ID NO: 69 is the amino acid sequence of LJL35.
SEQ ID NO: 70 is the nucleic acid sequence of LJL35.
SEQ ID NO: 71 is an oligonucleotide primer.
SEQ ID NO: 72 is an oligonucleotide primer.
SEQ ID NO: 73 is an oligonucleotide primer.

DETAILED DESCRIPTION

I. Abbreviations

AAV adeno-associated virus
AcNPV Autographa California Nuclear Polyhedrosis Virus
alum aluminum phosphate or aluminum hydroxide
BCG Bacillus Calmette Guerin
BLAST Basic Local Alignment Search Tool
BSA bovine serum albumin
CAV canine adenovirus
CDR complementarity determining region
CHV canine herpes virus
CMV cytomegalovirus
CTL cytotoxic T lymphocyte
DMRIE N-(2-hydroxyethyl)-N,N-dimethyl-2,3-bis(tetradecyloxy)-1-propanammonium
DOPE dioleoyl-phosphatidyl-ethanolamine
DTH delayed type hypersensitivity
fMLP N-formyl-methionyl-leucyl-phenylalanine
GM-CSF granulocyte-macrophage colony stimulating factor H heavy chains
HLB hydrophile-lipophile balance
ID intradermal
IM intramuscular
ISS immunostimulating sequence
KLH keyhole limpet hemocyanin
L light chains
LB Luria broth
*Lu. longipalpis Lutzomyia longipalpis*
MVA Modified Vaccinia virus Ankara
OFR open reading frame
*P. ariasi Phlebotomus ariasi*
PCR polymerase chain reaction
polyA polyadenylation signal
*P. papatasi Phlebotomus papatasi*
PVDF polyvinylidene difluoride
SC subcutaneous
SCA Single chain antibody
sFv single-chain antigen binding proteins
SGH salivary gland homogenate
SPGA sucrose phosphate glutamate albumin
tPA tissue plasminogen activator
$V_H$ variable region of the heavy chain
$V_L$ variable region of the light chain
VL visceral leishmaniasis

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Amplification of a nucleic acid molecule (for example, a DNA or RNA molecule): A technique that increases the number of copies of a nucleic acid molecule in a specimen. An example of amplification is the polymerase chain reaction, in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification may be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP 0320308; gap filling ligase chain reaction amplification, as disclosed in U.S. Pat. No. 5,427,930; and NASBA™ RNA transcription-free amplification, as disclosed in U.S. Pat. No. 6,025,134.

Antibody: immunoglobulin molecules and immunologically active portions of immunoglobulin molecules, for instance, molecules that contain an antigen binding site that specifically binds (immunoreacts with) an antigen.

A naturally occurring antibody (for example, IgG, IgM, IgD) includes four polypeptide chains, two heavy (H) chains and two light (L) chains inter-connected by disulfide bonds. However, it has been shown that the antigen-binding function of an antibody can be performed by fragments of a naturally occurring antibody. Thus, these antigen-binding fragments are also intended to be designated by the term "antibody." Specific, non-limiting examples of binding fragments encompassed within the term antibody include (i) an Fab fragment consisting of the $V_L$, $V_H$, CL, and CH1 domains; (ii) an Fd fragment consisting of the $V_H$ and CH1 domains; (iii) an Fv fragment consisting of the $V_L$ and $V_H$ domains of a single arm of an antibody, (iv) a dAb fragment (Ward et al., *Nature* 341:544-546, 1989) which consists of a $V_H$ domain; (v) an isolated complementarity determining region (CDR); and (vi) an $F(ab')_2$ fragment, a bivalent fragment comprising two Fab fragments linked by a disulfide bridge at the hinge region.

Immunoglobulins and certain variants thereof are known and many have been prepared in recombinant cell culture (for example, see U.S. Pat. No. 4,745,055; U.S. Pat. No. 4,444,487; WO 88/03565; EP 0256654; EP 0120694; EP 0125023; Faoulkner et al., *Nature* 298:286, 1982; Morrison, *J. Immunol.* 123:793, 1979; Morrison et al., *Ann Rev. Immunol* 2:239, 1984).

Animal: Living multi-cellular vertebrate organisms, a category that includes, for example, mammals and birds. The term mammal includes both human and non-human mammals. Similarly, the term "subject" includes both human and veterinary subjects, such as dogs.

Conservative variants: Conservative amino acid substitutions are those substitutions that do not substantially affect or decrease an activity or antigenicity of the *Lu. longipalpis* polypeptide. Specific, non-limiting examples of a conservative substitution include the following examples:

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variation also includes the use of a substituted amino acid in place of an unsubstituted parent amino acid, provided that antibodies raised to the unsubstituted polypeptide also essentially immunoreact with the substituted polypeptide, or that an immune response can be generated against the substituted polypeptide that is similar to the immune response against the unsubstituted polypeptide. Thus, in one embodiment, non-conservative substitutions are those that reduce an activity or antigenicity.

cDNA (complementary DNA): A piece of DNA lacking internal, non-coding segments (introns) and expression control sequences. cDNA is synthesized in the laboratory by reverse transcription from messenger RNA extracted from cells.

Degenerate variant: A polynucleotide encoding a *Lu. longipalpis* polypeptide that includes a sequence that is degenerate as a result of the genetic code. There are 20 natural amino acids, most of which are specified by more than one codon. Therefore, all degenerate nucleotide sequences are included in the disclosure as long as the amino acid sequence of the *Lu. longipalpis* polypeptide encoded by the nucleotide sequence is unchanged.

Delayed-type hypersensitivity (DTH): An immune reaction in which T cell-dependent macrophage activation and inflammation cause tissue injury. A DTH reaction to the subcutaneous injection of antigen is often used as an assay for cell-mediated immunity.

Epitope: An antigenic determinant. These are particular chemical groups or peptide sequences on a molecule that are antigenic, for instance, that elicit a specific immune response. An antibody specifically binds a particular antigenic epitope on a polypeptide. Specific, non-limiting examples of an epitope include a tetra- to penta-peptide sequence in a polypeptide, a tri- to penta-glycoside sequence in a polysaccharide. In the animal most antigens will present several or even many antigenic determinants simultaneously. Such a polypeptide may also be qualified as an immunogenic polypeptide and the epitope may be identified as described further.

Expression Control Sequences: Nucleic acid sequences that control and regulate the expression of a nucleic acid sequence, such as a heterologous nucleic acid sequence, to which it is operably linked Expression control sequences are operably linked to a nucleic acid sequence when the expression control sequences control and regulate the transcription and, as appropriate, translation of the nucleic acid sequence. Thus expression control sequences can include appropriate promoters, enhancers, transcription terminators, polyA signals, a start codon (for instance, ATG) in front of a protein-encoding polynucleotide sequence, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription of a nucleic acid. Promoters may be cell-type specific or tissue specific. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. Both constitutive and inducible promoters are included (see for example, Bitter et al., *Methods in Enzymology* 153:516-544, 1987).

For example, when cloning in bacterial systems, inducible promoters such as pL of bacteriophage lambda, plac, ptrp, ptac (ptrp-lac-hybrid promoter) and the like may be used. In one embodiment, when cloning in mammalian cell systems, promoters derived from the genome of mammalian cells (for example, metallothionein promoter) or from mammalian viruses (for example, the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells. In one embodiment, the promoter is a cytomegalovirus promoter.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used. Also includes the cells of the subject.

Immune response: A response of a cell of the immune system, such as a B cell, T cell, or monocyte, to a stimulus. In one embodiment, the response is specific for a particular antigen (an "antigen-specific response"). The response can also be a non-specific response (not targeted specifically to salivary polypeptides) such as production of lymphokines. In one embodiment, an immune response is a T cell response, such as a CD4+ response or a CD8+ response. In another embodiment, the response is a Th1 (a subset of helper T cells) response. In yet another embodiment, the response is a B cell response, and results in the production of specific antibodies.

Immunogenic polypeptide: A polypeptide which comprises an allele-specific motif, an epitope or other sequence such that the polypeptide will bind an MHC molecule and induce a cytotoxic T lymphocyte ("CTL") response, and/or a B cell response (for example, antibody production), and/or T-helper lymphocyte response, and/or a delayed type hypersensitivity (DTH) response against the antigen from which the immunogenic polypeptide is derived.

In one embodiment, immunogenic polypeptides are identified using sequence motifs or other methods known in the art. Typically, algorithms are used to determine the "binding threshold" of polypeptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing polypeptide. Within the context of an immunogenic polypeptide, a "conserved residue" is one which appears in a significantly higher frequency than would be expected by random distribution at a particular position in a polypeptide. In one embodiment, a conserved residue is one where the MHC structure may provide a contact point with the immunogenic polypeptide.

Immunogenic composition: A composition that, when administered to a subject induces an immune response to a *Lu. longipalpis* salivary polypeptide. In one embodiment, in particular a positive DTH response.

Isolated: An "isolated" biological component (such as a nucleic acid or protein or organelle) has been substantially separated or purified away from other biological components in the cell of the organism in which the component naturally occurs, for instance, other chromosomal and extra-chromosomal DNA and RNA, proteins, and organelles. Nucleic acids and proteins that have been "isolated" include nucleic acids and proteins purified by standard purification methods. The term also embraces nucleic acids and proteins prepared by recombinant technology as well as chemical synthesis.

Label: A detectable compound or composition that is conjugated directly or indirectly to another molecule to facilitate detection of that molecule. Specific, non-limiting examples of labels include fluorescent tags, enzymatic linkages, and radioactive isotopes.

*Leishmaniasis*: A parasitic disease spread by the bite of infected sand flies. The trypanosomatid parasite of the genus *Leishmania* is the etiological agent of a variety of disease manifestations, which are collectively known as leishmaniasis. *Leishmaniasis* is prevalent through out the tropical and sub-tropical regions of Africa, Asia, the Mediterranean, Southern Europe (old world), and South and Central America (new world). The old world species are transmitted by the sand fly vector *Phlebotomus* sp. Humans, wild animals and domestic animals (such as dogs) are known to be targets of these sand flies and to act as reservoir hosts or to develop leishmaniasis.

Cutaneous leishmaniasis starts as single or multiple nodules that develop into ulcers in the skin at the site of the bite. The chiclero ulcer typically appears as a notch-like loss of tissue on the ear lobe. The incubation period ranges from days to months, even a year in some cases. The sores usually last months to a few years, with most cases healing on their own. The mucocutaneous type can develop into erosive lesions in the nose, mouth, or throat and can lead to severe disfigurement. Visceral leishmaniasis often has fever occurring in a typical daily pattern, abdominal enlargement with pain, weakness, widespread swelling of lymph nodes, and weight loss, as well as superimposed infections because of a weakened immune system. Visceral leishmaniasis (VL) can result in high death rates. The onset of symptoms can be sudden, but more often tends to be insidious.

*Lutzomyia longipalpis* (*Lu. longipalpis*): A species of sand fly endogenous to the New World (South and Central America). This sand fly is the principal vector of American visceral leishmaniasis, a potentially fatal disease that primarily affects children in several countries of South and Central America.

Lymphocytes: A type of white blood cell that is involved in the immune defenses of the body. There are two main types of lymphocytes: B cells and T cells.

Mammal: This term includes both human and non-human mammals. Similarly, the term "subject" includes both human and veterinary subjects.

Oligonucleotide: A linear polynucleotide sequence of up to about 100 nucleotide bases in length.

Open reading frame (ORF): A nucleic acid sequence having a series of nucleotide triplets (codons), starting with a start codon and ending with a stop codon, coding for amino acids without any internal termination codons. These sequences are usually translatable into a polypeptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Polypeptide Modifications: *Lu. longipalpis* polypeptides include synthetic embodiments of polypeptides described herein. In addition, analogues (non-peptide organic molecules), derivatives (chemically functionalized peptide molecules obtained starting with the disclosed polypeptide sequences) and variants (homologs) of these proteins can be utilized in the methods described herein. Each polypeptide of the disclosure is comprised of a sequence of amino acids, which may be either L- and/or D-amino acids, naturally occurring and otherwise.

Polypeptides may be modified by a variety of chemical techniques to produce derivatives having essentially the same activity as the unmodified polypeptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring Amino groups of the peptide, whether amino-terminal or side chain, may be in the form of a pharmaceutically-acceptable acid addition salt, such as the HCl, HBr, acetic, benzoic, toluene sulfonic, maleic, tartaric, and other organic salts, or may be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine, or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of a *L. longipalpis* polypeptide having measurable or enhanced ability to generate an immune response. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs," Klegerman & Groves (eds.), 1993, *Pharmaceutical Biotechnology*, Interpharm Press: Buffalo Grove, Ill., pp. 165-174 and *Principles of Pharmacology* Munson (ed.) 1995, Ch. 102, for descriptions of techniques used in CADD. Also included are mimetics prepared using such techniques.

Pharmaceutically acceptable vehicles or excipients: The pharmaceutically acceptable vehicles or excipients of use are conventional. *Remington's Pharmaceutical Sciences*, by E. W. Martin, Mack Publishing Co., Easton, Pa., 15th Edition (1975), describes compositions and formulations suitable for pharmaceutical delivery of the polypeptides, plasmids, viral vectors herein disclosed.

In general, the nature of the vehicle or excipient will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, freeze-dried pastille, powder, pill, tablet, or capsule forms), conventional non-toxic solid vehicles or excipients can include, for example, pharmaceutical grades of mannitol, lactose, starch, or magnesium stearate. In addition to biologically neutral vehicles or excipients, immunogenic compositions to be administered can contain minor amounts of non-toxic auxiliary substances, such as wetting or emulsifying agents, preservatives, and pH buffering agents and the like, for example sodium acetate or sorbitan monolaurate.

*Phlebotomus ariasi* (*P. ariasi*): A species of *Phlebotomus* (sand flies) genus endogenous to the Old World, in particular to southern Europe and Mediterranean countries, more particularly to Spain and France. This sand fly is a proven vector of visceral leishmaniasis. *P. ariasi* is a member of the subgenera of *Phlebotomus Larroussius.*

*Phlebotomus perniciosus* (*P. perniciosus*): A species of *Phlebotomus* (sand flies) genus endogenous to the Old World, in particular to southern Europe, and Mediterranean countries, more particularly to France, Italy, Greece, Morocco, and Spain. This sand fly is a proven vector of the visceral leishmaniasis. *P. perniciosus* is a member of the subgenera of *Phlebotomus Larroussius.*

Polynucleotide: The term polynucleotide or nucleic acid sequence refers to a polymeric form of nucleotide at least 10 bases in length, thus including oligonucleotides and genes. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (for example, a cDNA) independent of other sequences. The polynucleotides can be ribonucleotides, deoxyribonucleotides, or modified forms of either nucleotide. The term includes single- and double-stranded forms of DNA.

Polypeptide: Any chain of amino acids, regardless of length (thus encompassing oligopeptides, peptides, and proteins) or post-translational modification (for example, glycosylation, phosphorylation, or acylation). A polypeptide encompasses also the precursor, as well as the mature protein. In one embodiment, the polypeptide is a polypeptide isolated from *Lu. longipalpis*, or encoded by a nucleic acid isolated from *Lu. longipalpis*, such as the *Lu. longipalpis* polypeptides disclosed herein.

Probes and primers: A probe comprises an isolated polynucleotide attached to a detectable label or reporter molecule. Primers are short polynucleotides. In one embodiment, polynucleotides are 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, for example, by the polymerase chain reaction (PCR) or other nucleic-acid amplification methods known in the art. One of skill in the art will appreciate that the specificity of a particular probe or primer increases with its length. Thus, for example, a primer comprising 20 consecutive nucleotides will anneal to a target with a higher specificity than a corresponding primer of only 15 nucleotides. Thus, in order to obtain greater specificity, probes and primers may be selected that comprise at least 15, 20, 25, 30, 35, 40, 50 or more consecutive nucleotides.

Protein Purification: The *Lu. longipalpis* polypeptides disclosed herein can be purified by any of the means known in the art. See, for example, *Guide to Protein Purification*, Deutscher (ed.), *Meth. Enzymol.* 185, Academic Press, San Diego, 1990; and Scopes, *Protein Purification: Principles and Practice*, Springer Verlag, New York, 1982. Substantial purification denotes purification from other proteins or cellular components. A substantially purified protein is at least 60%, 70%, 80%, 90%, 95%, or 98% pure. Thus, in one specific, non-limiting example, a substantially purified protein is 90% free of other proteins or cellular components.

Purified: The term purified does not require absolute purity; rather, it is intended as a relative term. Thus, for example, a purified polypeptide preparation is one in which the polypeptide is more enriched than the polypeptide is in its natural environment. A polypeptide preparation is substantially purified such that the polypeptide represents several embodiments at least 60%, at least 70%, at least 80%, at least 90%, at least 95%, or at least 98%, of the total polypeptide content of the preparation. The same applies for polynucleotides. The polypeptides disclosed herein can be purified by any of the means known in the art (see, for example, *Guide to Protein Purification*, Deutscher (ed.), *Meth. Enzymol.* 185, Academic Press, San Diego, 1990; and Scopes, *Protein Purification: Principles and Practice*, Springer Verlag, New York, 1982).

Recombinant: A recombinant polynucleotide is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques. In one embodiment, a recombinant polynucleotide encodes a fusion protein.

Selectively hybridize: Hybridization under moderately or highly stringent conditions that excludes non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (for example, GC v. AT content), and nucleic acid type (for example, RNA v. DNA) of the hybridizing regions of the nucleic acids can be considered in selecting hybridization conditions. An additional consideration is whether one of the nucleic acids is immobilized, for example, on a filter.

A specific, non-limiting example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). One of skill in the art can readily determine variations on these conditions (for example, *Molecular Cloning: A Laboratory Manual,* 2nd ed., vol. 1-3, ed. Sambrook et al., Cold Spring Harbor Laboratory Press, Cold Spring Harbor, N.Y., 1989). The hybridization conditions can be carried out over 2 to 16 hours. Washing can be carried out using only one of the above conditions, for example, high stringency conditions, or each of the conditions can be used, for example, for 10-15 minutes each, in the order listed above, repeating any or all of the steps listed. However, as mentioned above, optimal conditions will vary, depending on the particular hybridization reaction involved, and can be determined empirically.

Sequence identity: The similarity between amino acid sequences is expressed in terms of the percentage identity between the sequences. The higher the percentage, the more similar the two sequences are. Homologs or variants of a *Lu. longipalpis* polypeptide will possess a relatively significant high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. USA* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. USA* 85:2444, 1988. Altschul et al., *Nature enet.* 6:119, 1994 presents a detailed consideration of sequence alignment methods and identity calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the Internet, for use in connection with the sequence analysis programs blastp, blastn, blastx, tblastn, and tblastx. A description of how to determine sequence identity using this program is available on the NCBI website on the internet.

Homologs and variants of a *Lu. longipalpis* polypeptide are typically characterized by possession of at least 75%, for example at least 80%, sequence identity counted over the full length alignment with the amino acid sequence of the *Lu. longipalpis* polypeptide using the NCBI Blast 2.0, gapped blastp set to default parameters. The comparison between the sequences is made over the full length alignment with the amino acid sequence given in this present disclosure, employing the Blast 2 sequences function using the default BLOSUM62 matrix set to default parameters, (gap existence cost of 11, and a per residue gap cost of 1).

When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologues and, variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologues could be obtained that fall outside of the ranges provided.

Specific binding agent: An agent that binds substantially only to a defined target. Thus a *Lu. longipalpis* specific binding agent is an agent that binds substantially to a *Lu. longipalpis* polypeptide.

In one embodiment, the specific binding agent is a monoclonal or polyclonal antibody that specifically binds the *Lu. longipalpis* polypeptide.

Subject: Living multi-cellular vertebrate organisms, a category that includes both human veterinary subjects, including human and non-human mammals. In one embodiment, the subject is a member of the canine family, such as a dog. In another embodiment, the subject is a human T Cell: A white blood cell critical to the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, help orchestrate the immune response, including antibody responses as well as killer T cell responses. $CD8^+$ T cells carry the "cluster of differentiation 8" (CD8) marker. In one embodiment, a CD8 T cells is a cytotoxic T lymphocytes. In another embodiment, a CD8 cell is a suppressor T cell.

Therapeutically active polypeptide: An agent, such as a *Lu. longipalpis* polypeptide, that causes induction of an immune response, as measured by clinical response (for example, increase in a population of immune cells, production of antibody that specifically binds the *Lu. longipalpis* polypeptide, a measurable reduction in symptoms resulting from exposure to*Leishmania*, or protection from infection with *Leishmania*). Therapeutically active molecules can also be made from nucleic acids. Examples of a nucleic acid based therapeutically active molecule is a nucleic acid sequence that encodes a *Lu. longipalpis* polypeptide, wherein the nucleic acid sequence is operably linked to a control element such as a promoter. Therapeutically active agents can also include organic or other chemical compounds that mimic the effects of the *Lu. longipalpis* polypeptide.

The terms "therapeutically effective fragment of a *Lu. longipalpis* polypeptide" includes any fragment of the *Lu. longipalpis* polypeptide, or variant of the *Lu. longipalpis* polypeptide, or fusion protein including a *Lu. longipalpis* polypeptide, that retains a function of the *Lu. longipalpis* polypeptide (such as immunogenicity), or retains the ability to reduce the symptoms from exposure to *Leishmania*, or to protect from infection with *Leishmania.*

Thus, in one embodiment, a therapeutically effective amount of a fragment of *Lu. longipalpis* polypeptide is an amount used to generate an immune response to the polypeptide. In another embodiment, a therapeutically effective amount of a fragment of a *Lu. longipalpis* polypeptide is an amount of use to prevent or treat a *Leishmania* infection in a subject. Treatment refers to a therapeutic intervention that confers resistance to infection with *Leishmania*, or a reduction in the symptoms associated with exposure to *Leishmania*. Specific, non-limiting examples of a polypeptide fragment are the N-terminal half or the C-terminal half of one of the *P. Lu. longipalpis* polypeptide disclosed herein. It should be noted that fusion proteins are included, such as a fusion with six histidine residues, a c-myc tag, or any other polypeptide tag. Such fusions are known to one of skill in the art, and are often used in protein purification.

Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transduced host cell. A vector may include nucleic acid sequences that permit it to replicate in a host cell, such as an origin of replication. A vector may also include one or more selectable marker genes and other genetic elements known in the art.

Vaccine: Composition that when administered to a subject, induces a decrease of the severity of the symptoms of a disorder or disease. In one embodiment, a vaccine decreases the severity of the symptoms of leishmaniasis and/or decreases the parasitic load.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. "Comprise" means "include," and a composition that comprises a polypeptide includes that polypeptide. It is further to be understood that all base sizes or amino acid sizes, and all molecular weight or molecular mass values, given for polynucleotides or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

*Lu. longipalpis* Polynucleotides and Polypeptides

Salivary polypeptides from sand fly species *Lu. longipalpis*, are disclosed herein.

```
LJL34
                                                    (SEQ ID NO: 1)
MLQIKHLLIFVGLLVVVNAQSNYCKQESCSSGGVERPHIGCKNSGDFSETCSGDAEIVK

MDKKKQNLLVKMHNRLRDRFARGAVPGFAPAAKMPMLKWNDELAKLAEYNVRTCK

FAHDKCRAIDVCPYAGQNLAQMMSYPTHRDLNYVLKNLTREWFWEYRWAKQSQLD

NYVGGPGKDNKQIGHFTAFVHEKTDKVGCAIARFTNEHNFKETLLACNYCYTNMMKE

RIYTQGKPCSQCQSKKCGPVYKNLCDPSEKVDPTPDVLKQWKHGK

LJL18
                                                    (SEQ ID NO: 3)
MLLRSLFVLFLIFLTFCNAEEELIERKLTGKTIYISTIKLPWFQALNHCVKNGYTMVSIKT

FEENKELLKELKRVIRTEDTQVWIGGLKHHQFANFRWVSDGSHVATASGYTNWAPGE

PADSFYYDQFCMAMLFRKDGAPWDDLNCWVKNLFVCEKRDD

LJS193
                                                    (SEQ ID NO: 5)
MKLLQIIFSLFLVFFPTSNGALTGNESAANAAPLPVVLWHGMGDSCCFPFSLGSIKKLIE

QQIPGIHVVSLKIGKSLIEDYESGFFVHPDKQIQEVCESLQNDLTLANGFNAIGFSQGSQF

LRGLVQRCSSIQVRNLISIGGQHQGVFGLPYCPSLSRKTCEYFRKLLNYAAYEKWVQKL

LVQATYWHDPLNEDAYRTGSTFLADINNERQINNDYINNIRKLNRFVMVKFLNDSMVQ

PIESSFFGFYAPGTDTEVLPLKQSKIYLEDRLGLQSVPIDYLECGGDHLQFTKEWFIKFIIP

YLKQ

LJS201
                                                    (SEQ ID NO: 7)
MRNFAVVSLAVAVLLFCAWPINAEDNEEVGKAREKRGLKDAMEHFKNGFKELTKDFK

LPSLPSLPGFGKKPESGSSEDSGDKTEDTSGSKDDQSKDNTVEES

LJL13
                                                    (SEQ ID NO: 9)
MNFLLKIFSLLCLCGLGYSWQDVRNADQTLWAYRSCQKNPEDKDHVPQWRKFELPDD

EKTHCYVKCVWTRLGAYNENENVFKIDVITKQFNERGLEVPAGLDQELGGSTDGTCK

AVYDKSMKFFKSHFMDFRNAYYATYDGSDEWFSKNPDVKPKGTKVSEYCKNKDDGD

CKHSCSMYYYRLIDEDNLVIPFSNLPDYPEDKLEECRNEAKSANECKSSVIYQCLENAD

KSALDASLNILDEFSGRY
```

-continued

LJL23

(SEQ ID NO: 11)

MFLKWVVCAFATVFLVGVSQAAPPGVEWYHFGLIADMDKKSIASDKTTFNSVLKIDEL

RHNTKTDQYIYVRSRVKKPVSTRYGFKGRGAELSEIVVFNNKLYTVDDKSGITFRITKD

GKLFPWVILADADGQRPDGFKGEWATIKDDTIYVGSTGMLKFTSSLWVKKITKDGVVT

SHDWTDKYRKILKALNMPNGFVWHEAVTWSPFRKQWVFMPRKCSRHPFSQELEERTG

CNKIVTADENFNDIQVIHIQDQPYNLASGFSSFRFIPGTKNERLLALRTVEQEDQVKTWA

VVMDMKGTVLMYEKELYDEKFEGLAFFGGIKKN

LJM10

(SEQ ID NO: 13)

MALKFLPVLLLSCFAMSTALQVTEKELSDGKKIFISKVELNWFEALDFCIHRGLTLLSIK

SAKENVDVTKAIRAELNFDSKKLAHVWTGGIRHSQDKYFRWINDGTKVVKRVYTNWF

TGEPNNGYWKDEFCLEIYYKTEEGKWNDDKCHVKHHFVCQEKK

LJL143

(SEQ ID NO: 15)

MNSINFLSIVGLISFGFIVAVKCDGDEYFIGKYKEKDETLFFASYGLKRDPCQIVLGYKC

SNNQTHFVLNFKTNKKSCISAIKLTSYPKINQNSDLTKNLYCQTGGIGTDNCKLVFKKR

KRQIAANIEIYGIPAKKCSFKDRYIGADPLHVDSYGLPYQFDQEHGWNVERYNIFKDTR

FSTEVFYHKNGLFNTQITYLAEEDSFSEAREITAKDIKKKFSIILPNEEYKRISFLDVYWF

QETMRKKPKYPYIHYNGECSNENKTCELVFDTDELMTYALVKVFTNPESDGSRLKEED

LGRG

LJS142

(SEQ ID NO: 17)

MAFSNTLFVLFVSFLTFCGADQTLIEKELTGRTVYISKIKLNWNDAFDYCIRNGLTFAKI

KSAEENTELSEKLKTVIRTEEFQVWIGGIEHHQDSSFRWVSDSQPITNKLGYKYTNWNT

GEPTNYQNNEYCLEILFRKEDGKWNDFPCSARHHFVCEKRTK

LJL17

(SEQ ID NO: 19)

MQNFLLVSLALAALMLCAEAKPYDFPLYQDLIQGVIQRESQAEREKRSPNEDYEKQFG

DIVDQIKEISFNVMKMPHFGSSDDNRDDGEYVDHHYGDEDDRDYDHY

LJM06

(SEQ ID NO: 21)

MKFYIFGVFLVSFLALCNAEDYDKVKLTGRTVYISRSKAPWFTALDNCNRRFTFAMIKS

QKENEELTNALLSVIKSDEENVWIGGLRHDLDDYFRWISFGTALSKTSYTNWAPKEPTG

RPHRTQNDEFCMQMSFKDGGKWSDNTCWRKRLYVCEKRD

LJM17

(SEQ ID NO: 23)

MRFFFVFLAIVLFQGIHGAYVEIGYSLRNITFDGLDTDDYNPKFNIPTGLAVDPEGYRLFI

AIPRRKPKVPYTVAELNMVMNPGFPVERAPSFEKFKKFNGEGKKDLVNVYQPVIDDCR

RLWVLDIGKVEYTGGDADQYPKGKPTLIAYDLKKDHTPEIHRFEIPDDLYSSQVEFGGF

AVDVVNTKGDCTESFVYLTNFKDNSLIVYDETQKKAWKFTDKTFEADKESTFSYSGEE

QMKYKVGLFGIALGDRDEMGHRPACYIAGSSTKVYSVNTKELKTENGQLNPQLHGDR

GKYTDAIALAYDPEHKVLYFAESDSRQVSCWNVNMELKPDNTDVIFSSARFTFGTDILV

DSKGMLWIMANGHPPVEDQEKIWKMRFVNRKIRIMKVDTERVFKYSRCNPNYKPPK

EIEV

LJL04

(SEQ ID NO: 25)

MIKEVFSLALLVALAQCANEIPINRQGKDYPVPIIDPNKSSSDDYFDDRFYPDIDDEGIAE

APKDNRGKSRGGGAAGAREGRLGTNGAKPGQGGTRPGQGGTRPGQGGTRPGQGGTR

-continued

PGQGGTRPGQGRTKPAQGTTRPAQGTRNPGSVGTKEAQDASKQGQGKRRPGQVGGK

RPGQANAPNAGTRKQQKGSRGVGRPDLSRYKDAPAKFVFKSPDFSGEGKTPTVNYFRT

KKKEHIVTRGSPNDEFVLEILDGDPTGLGLKSETIGKDTRLVLENPNGNSIVARVKIYKN

GYSG

LJM114

(SEQ ID NO: 27)

MNSVNTLILTLLFAIFLLVKRSQAFLPSDPSICVKNLVLDTGRTCEESEYFPDIKNVKNG

KRVYIVCTDSDAVDYKFYICFDMNRLSGPPYPEEEILRESTVTYAQIYELMTTETTETKK

PKKKPKNSKTDDPPAIRPGFSFRNSISV

LJM111

(SEQ ID NO: 29)

MKLFFFLYTFGLVQTIFGVEIKQGFKWNKILYEGDTSENFNPDNNILTAFAYDPESQKLF

LTVPRKYPETMYTLAEVDTEKNSFESGDTSPLLGKFSGHETGKELTSVYQPVIDECHRL

WVVDVGSVERNSDGTEGQPEHNPTLVAYDLKEANYPEVIRYTFPDNSIEKPTFLGGFA

VDVVKPDECSETFVYITNFLTNALIVYDHKNKDSWTVQDSTFGPDKKSKFDHDGQQYE

YEAGIFGITLGERDNEGNRQAYYLVASSTKLHSINTKELKQKGSKVNANYLGDRGEST

DAIGLVYDPKTKTIFFVESNSKRVSCWNTQETLNKDKIDVIYHNADFSFGTDISIDSQDN

LWFLANGLPPLENSDKFVFTKPRYQIFKVNIQEAIAGTKCEKNL

LJM78

(SEQ ID NO: 31)

MTFLIIILGAFLLVQIITASALGLPEQFKGLEDLPKKPLAETYYHEGLNDGKTDEMVDIFK

SLSDEFKFSDENLDVGEEKNYKKRDITQNSVARNFLSNVKGIPSMPSLPSMPSMPSIPSL

WSSQTQAAPNTALALPESDYSLLDMPNIVKNFLKETRDLYNDVGAFLKAITEALTNRSS

SSQLLSSPMVSTNKTKEFIRNEIQKVRKVRNFVQETLQKIRDISAAIAKKVKSSECLSNLT

DIKGLVSDGINCLKEKFNDGKRIILQLYNNLLKGLKIPNDLMVELKKCDTNQNNTLGRII

CYFLTPLQLEKEQILLPVEFIKRILELTHYFSTMKEDLINCGITTIASIT

LJS238

(SEQ ID NO: 33)

MLKIVLFLSVLAVLVICVAAMPGSNVPWHISREELEKLREARKNHKALEKAIDELIDKY

L

LJS169

(SEQ ID NO: 35)

MKFSCPVFVAIFLLCGFYRVEGSSQCEEDLKEEAEAFFKDCNEAKANPGEYENLTKEE

MFEELKEYGVADTDMETVYKLVEECWNELTTTDCKRFLEEAECFKKKNICKYFPDEV

KLKKK

LJL11

(SEQ ID NO: 37)

MLFFLNFFVLVFSIELALLTASAAAEDGSYEIIILHTNDMHARFDQTNAGSNKCQEKDKI

ASKCYGGFARVSTMVKKFREENGSSVLFLNAGDTYTGTPWFTLYKETIATEMMNILRP

DAASLGNHEFDKGVEGLVPFLNGVTFPILTANLDTSQEPTMTNAKNLKRSMIFTVSGHR

VGVIGYLTPDTKFLSDVGKVNFIPEVEAINTEAQRLKKEENAEIIIVVGHSGLIKDREIAE

KCPLVDIIVGGHSHTFLYTGSQPDREVPVDVYPVVVTQSSGKKVPIVQAYCFTKYLGYF

KVTINGKGNVVGWTGQPILLNNNIPQDQEVLTALEKYRERVENYGNRVIGVSRVILNG

GHTECRFHECNMGNLITDAFVYANVISTPMSTNAWTDASVVLYQSGGIRAPIDPRTAA

GSITRLELDNVLPFGNALYVVKVPGNVLRKALEHSVHRYSNTSGWGEFPQVSGLKIRF

NVNEEIGKRVKSVKVLCSNCSQPEYQPLRNKKTYNVIMDSFMKDGGDGYSMFKPLKII

-continued

KTLPLGDIETVEAYIEKMGPIFPAVEGRITV

LGGLQKSDEDWH

LJL08

(SEQ ID NO: 39)

MKQILLISLVVILAVLAFNVAEGCDATCQFRKAIEDCKKKADNSDVLQTSVQTTATFTS

MDTSQLPGNNVFKACMKEKAKEFRAGK

LJS105

(SEQ ID NO: 41)

MNVLFVSFTLTILLLCVKARPEDFVALQDQANFQKCLEQYPEPNQSGEVLACLKKREG

AKDFREKRSLDDIEGTFQESGN

LWGA

LJL09

(SEQ ID NO: 43)

MKITVILFTGFTIALVSSAVLKKNGETIEEEEVRAEQRLREINEELDRRKNINTVAAWAY

ASNITEVNLKNMNDVSVETAKYYKELASELKGFNAKEYKSEDLKRQIKKLSKLGYSAL

PSEKYKELLEAITWMESNYAKVKVCSYKDPKKCDLALEPEITEILIKSRDPEELKYYWK

QWYDKAGTPTRESFNKYVQLNREAAKLDGFYSGAESWLDEYEDETFEKQLEDIFAQIR

PLYEQLHAYVRFKLREKYGNDVVSEKGPIPMHLLGNMWGQTWSEVAPILVPYPEKKL

LDVTDEMVKQGYTPISMFEKGDEFFQSLNMTKLPKTFWEYSILEKPQDGRELICHASA

WDFYTKDDVRKQCTRVTMDQFFTAHHELGHIQYYLQYQHLPSVYREGANPGFHEAV

GDVLSLSVSSPKHLEKVGLLKDFKFDEESQINQLLNLALDKMAFLPFAYTIDKYRWGVF

RGEISPSEYNCKFWEMRSYYGGIEPPIARSESDFDPPAKYHISSDVEYLRYLVSFIIQFQF

HQAVCQKTGQFVPNDPEKTLLNCDIYQSAEAGNAFKEMLKLGSSKPWPDAMEILTGQ

RKMDASALIEYFRPLSEWLQKKNKELGAYVGWDKSTKCVKNVS

LJL38

(SEQ ID NO: 45)

MKTFALIFLALAVFVLCIDGAPTFVNLLDDVQEEVEVNTYEP

LJM04

(SEQ ID NO: 47)

MNHLCFIIIALFFLVQQSLAEHPEEKCIRELARTDENCILHCTYSYYGFVDKNFRIAKKH

VQKFKKILVTFGAVPKKEKKKLLEHIEACADSANADQPQTKDEKCTKINKYYRCVVDG

KILPWNSYADAIIKFDKTLNV

LJM26

(SEQ ID NO: 49)

MKIIFLAAFLLADGIWAAEEPSVEIVTPQSVRRHATPKAQDARVGSESATTAPRPSESMD

YWENDDFVPFEGPFKDIGEFDWNLSKIVFEENKGNAILSPLSVKLLMSLLFEASASGTLT

QHQLRQATPTIVTHYQSREFYKNIFDGLKKKSNDYTVHFGTRIYVDQFVTPRQRYAAIL

EKHYLTDLKVEDFSKAKETTQAINSWVSNITNEHIKDLVKEEDVQNSVMLMLNAVYFR

GLWRKPFNRTLPLPFHVSADESKTTDFMLTDGLYYFYEAKELDAKILRIPYKGKQYAM

TVILPNSKSGIDSFVRQINTVLLHRIKWLMDEVECRVILPKFHFDMTNELKESLVKLGIS

QIFTSEASLPSLARGQGVQNRLQVSNVIQKAGIIVDEKGSTAYAASEVSLVNKFGDDEF

VMFNANHPFLFTIEDETTGAILFTGKVVDPTQ

LJS03

(SEQ ID NO: 51)

MRFLLLAFSVALVLSPTFAKPGLWDIVTGINDMVKNTANALKNRLTTSVTLFTNTITEAI

KNANSSVSELLQQVNETLTDIINGVGQVQSAFVNSAGNVVVQIVDAAGNVLEVVVDEA

GNIVEVAGTALETIIPLPGVVIQKIIDALQGNAGTTSDSASSTVPQQS

-continued

LJS192

(SEQ ID NO: 53)

MVKYSCLVLVAIFLLAGPYGVVGSCENDLTEAAKYLQDECNAGEIADEFLPFSEEEVGE

ALSDKPENVQEVTNIVRGCFEAEQAKEHGKCERFSALSQCYIEKNLCQFF

LJM19

(SEQ ID NO: 55)

MKFFYLIFSAIFFLADPALVKCSEDCENIFHDNAYLLKLDCEAGRVDPVEYDDISDEEIY

EITVDVGVSSEDQEKVAKIIRECIAQVSTQDCTKFSEIYDCYMKKKICNYYPENM

LJL138

(SEQ ID NO: 57)

MHLQLNLCAILLSVLNGIQGAPKSINSKSCAISFPENVTAKKEPVYLKPSNDGSLSTPLQP

SGPFVSLKIGESLAIFCPGDGKDVETITCNTNFDLASYSCNKSTSTDTIETEEVCGGSGKV

YKVGFPLPSGNFHSIYQTCFDKKNLTPLYSIHILNGQAVGYHLKHTRGSFRTNGIYGKV

NIDKLYKTQIEKFNKLFGPKQTFFRRPLNFLSRGHLSPEVDFTFRREQHATEMYINTAPQ

YQSINQGNWLRVENHVRDLAKVLQKDITVVTGILGILRLKSKKIEKEIYLGDDVIAVPA

MFWKAVFDPQKQEAIVFVSSNNPHVKTFNPNCKDVCAQAGFGNDNLEYFSNYSIGLTI

CCKLEEFVKRNKIILPKEVNNKNYTKKLLKFPKTRNKEGDKKVVRKRAKGA

LJL15

(SEQ ID NO: 59)

MNLHLAIILFVSYFTLITATDLIEKELSDCKKIFISKAELTWFQALDFCTEQNLTLLSIKSA

RENDEVTKAVRAEVHLPDTKKSHIWLGGIRYDQDKDFRWISDGTTVTKTVYINWYQG

EPNGGRYQKEFCMELYFKTPAGQWNDDICTAKHHFICQEKK

LJL91

(SEQ ID NO: 61)

MNLPLAIILFVSYFTLITAADLTEKELSDGKKIFISKAELSWFDALDACTEKDLTLLTIKS

ARENEEVTKAVRAEVHLPDTKKSHIWLGGIRYDQDKDFRWISDGTTVTKTVYINWYQ

GEPNGGRYQKEFCMELYFKTPAGQWNDDICTAKHHFICQEKK

LJM11

(SEQ ID NO: 63)

MKVFFSIFTLVLFQGTLGADTQGYKWKQLLYNNVTPGSYNPDNMISTAFAYDAEGEKL

FLAVPRKLPRVPYTLAEVDTKNSLGVKGKHSPLLNKFSGHKTGKELTSIYQPVIDDCRR

LWVVDIGSVEYRSRGAKDYPSHRPAIVAYDLKQPNYPEVVRYYFPTRLVEKPTYFGGF

AVDVANPKGDCSETFVYITNFLRGALFIYDHKKQDSWNVTHPTFKAERPTKFDYGGKE

YEFKAGIFGITLGDRDSEGNRPAYYLAGSAIKVYSVNTKELKQKGGKLNPELLGNRGK

YNDAIALAYDPKTKVIFFAEANTKQVSCWNTQKMPLRMKNTDVVYTSSRFVFGTDISV

DSKGGLWFMSNGFPPIRKSEKFKYDFPRYRLMRIMDTQEAIAGTACDMNA

LJS138

(SEQ ID NO: 65)

MQSKILSFVLFTLSLGYVLGETCSNAKVKGATSYSTTDATIVSQIAFVTEFSLECSNPGSE

KISLFAEVDGKITPVAMIGDTTYQVSWNEEVNKARSGDYSVKLYDEEGYGAVRKAQR

SGEENKVKPLATVVVRHPGTYTGPWFNSEILAAGLIAVVAYFAFSTRSKILS

LJL124

(SEQ ID NO: 67)

MVSILLISLILNLLVFYAKARPLEDISSDLSPDYYITEGYDGVKEKREIELVPVTFGIFNIH

TTPAPRITFEW

LJL35

(SEQ ID NO: 69)

MKLFCLIFVVFVALEVCIETVKAMEATEEISVKLQDDANEPDDSLDLDEGLPDAFDEDY

NNQAEYKPNPRGDYRRR

In one embodiment, a polypeptide including SEQ ID NO: 3, SEQ ID NO: 5, SEQ ID NO: 7, SEQ ID NO: 9, SEQ ID NO: 15, SEQ ID NO: 17, SEQ ID NO: 19, SEQ ID NO: 21, SEQ ID NO: 25, SEQ ID NO: 27, SEQ ID NO: 29, SEQ ID NO: 31, SEQ ID NO: 33, SEQ ID NO: 35, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 59, SEQ ID NO: 61, SEQ ID NO: 63, SEQ ID NO: 65, or SEQ ID NO: 67 is disclosed herein. Homologous polypeptides having an amino acid sequence at least 75%, 80%, 85%, 90%, 95%, 98%, or 99% identical to the amino acid sequence as set forth as SEQ ID NO: 3, SEQ ID NO: 5, SEQ ID NO: 7, SEQ ID NO: 9, SEQ ID NO: 15, SEQ ID NO: 17, SEQ ID NO: 19, SEQ ID NO: 21, SEQ ID NO: 25, SEQ ID NO: 27, SEQ ID NO: 29, SEQ ID NO: 31, SEQ ID NO: 33, SEQ ID NO: 35, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 59, SEQ ID NO: 61, SEQ ID NO: 63, SEQ ID NO: 65, or SEQ ID NO: 67 are disclosed herein. Fusion proteins including SEQ ID NO: 3, SEQ ID NO: 5, SEQ ID NO: 7, SEQ ID NO: 9, SEQ ID NO: 15, SEQ ID NO: 17, SEQ ID NO: 19, SEQ ID NO: 21, SEQ ID NO: 25, SEQ ID NO: 27, SEQ ID NO: 29, SEQ ID NO: 31, SEQ ID NO: 33, SEQ ID NO: 35, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 59, SEQ ID NO: 61, SEQ ID NO: 63, SEQ ID NO: 65, or SEQ ID NO: 67 are also disclosed herein.

Fragments and variants of the *Lu. longipalpis* polypeptides identified above are disclosed herein and can readily be prepared by one of skill in the art using molecular techniques. In one embodiment, a fragment of a *Lu. longipalpis* polypeptide includes at least 8, 10, 15, or 20 consecutive amino acids of a *Lu. longipalpis* polypeptide. In another embodiment, a fragment of a *Lu. longipalpis* polypeptide includes a specific antigenic epitope found on a full-length *Lu. longipalpis* polypeptide.

In one embodiment, a fragment is at least 19 amino acids, at least 23 amino acids, at least 25 amino acids, or at least 30 amino acids in length from any polypeptide (including polypeptides as given in SEQ ID NO: 3, SEQ ID NO: 5, SEQ ID NO: 7, SEQ ID NO: 9, SEQ ID NO: 15, SEQ ID NO: 17, SEQ ID NO: 19, SEQ ID NO: 21, SEQ ID NO: 25, SEQ ID NO: 27, SEQ ID NO: 29, SEQ ID NO: 31, SEQ ID NO: 33, SEQ ID NO: 35, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 59, SEQ ID NO: 61, SEQ ID NO: 63, SEQ ID NO: 65, or SEQ ID NO: 67 conservative variants thereof, and homologues thereof), or any fragment that retains at least an epitope.

Fusion proteins including a *Lu. longipalpis* polypeptide can also be produced using methods known to one of skill in the art. In one embodiment, a fusion protein includes an amino acid sequence set forth as SEQ ID NO: 3, SEQ ID NO: 5, SEQ ID NO: 7, SEQ ID NO: 9, SEQ ID NO: 15, SEQ ID NO: 17, SEQ ID NO: 19, SEQ ID NO: 21, SEQ ID NO: 25, SEQ ID NO: 27, SEQ ID NO: 29, SEQ ID NO: 31, SEQ ID NO: 33, SEQ ID NO: 35, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 59, SEQ ID NO: 61, SEQ ID NO: 63, SEQ ID NO: 65, or SEQ ID NO: 67, or a conservative variants thereof, and a marker polypeptide. Marker polypeptides include, but are not limited to, polypeptide tags, such as a polypeptide to aid in protein purification (for example, six histidine residues or c-myc polypeptide), or an enzymatic marker (for example, alkaline phosphatase), or a fluorescent maker (for example, green fluorescent protein).

One skilled in the art, given the disclosure herein, can purify a *Lu. longipalpis* polypeptide using standard techniques for protein purification. The substantially pure polypeptide will yield a single major band on a non-reducing polyacrylamide gel. The purity of the *Lu. longipalpis* polypeptide can also be determined by amino-terminal amino acid sequence analysis.

Minor modifications of the *Lu. longipalpis* polypeptide primary amino acid sequences may result in peptides which have substantially equivalent activity as compared to the unmodified counterpart polypeptide described herein. Such modifications may be deliberate, as by site-directed mutagenesis, or may be spontaneous. All of the polypeptides produced by these modifications are included herein.

Polynucleotides encoding salivary polypeptides from *Lu. longipalpis* sand fly are disclosed herein, such as polynucleotides encoding SEQ ID NO: 3, SEQ ID NO: 5, SEQ ID NO: 7, SEQ ID NO: 9, SEQ ID NO: 15, SEQ ID NO: 17, SEQ ID NO: 19, SEQ ID NO: 21, SEQ ID NO: 25, SEQ ID NO: 27, SEQ ID NO: 29, SEQ ID NO: 31, SEQ ID NO: 33, SEQ ID NO: 35, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 59, SEQ ID NO: 61, SEQ ID NO: 63, SEQ ID NO: 65, or SEQ ID NO: 67.

Specific, non-limiting examples of *Lu. longipalpis* nucleic acid sequences include SEQ ID NO:4, SEQ ID NO:6, SEQ ID NO:8, SEQ ID NO:10, SEQ ID NO:16, SEQ ID NO:18, SEQ ID NO:20, SEQ ID NO:22, SEQ ID NO:26, SEQ ID NO:28, SEQ ID NO:30, SEQ ID NO:32, SEQ ID NO:34, SEQ ID NO:36, SEQ ID NO:42, SEQ ID NO:44, SEQ ID NO:46, or SEQ ID NO:48, SEQ ID NO:50, SEQ ID NO:52, SEQ ID NO:54, SEQ ID NO:56, SEQ ID NO:58, SEQ ID NO:60, SEQ ID NO:62, SEQ ID NO:64, SEQ ID NO:66, SEQ ID NO:68, and degenerate variants thereof. These polynucleotides include DNA, cDNA, and RNA sequences that encode a *Lu. longipalpis* polypeptide. It is understood that all polynucleotides encoding a *Lu. longipalpis* polypeptide are also included herein, as long as they encode a polypeptide with the recognized activity, such as the binding to an antibody that recognizes the polypeptide, the induction of an immune response to the polypeptide, or an effect on survival of *Leishmania* when administered to a subject having leishmaniasis or who undergoes a decrease in a sign or a symptom of *Leishmania* infection.

The polynucleotides of the disclosure include sequences that are degenerate as a result of the genetic code. There are 20 natural amino acids, most of which are specified by more than one codon. Therefore, all degenerate nucleotide sequences are included in the disclosure as long as the amino acid sequence of the *Lu. longipalpis* polypeptide encoded by the nucleotide sequence is functionally unchanged.

Specific, non-limiting examples of a polynucleotide encoding a *P. ariasi* polypeptide are set forth below:

```
LJL34
                                        (SEQ ID NO: 2)
AGTTGTGGAGCTTTTGGTCATTTTACGTGATGTTGCAAATTAAACATCTT

CTGATTTTTGTGGGATTGCTCGTGGTTGTTAATGCACAGAGCAATTACTG

CAAACAGGAATCGTGCTCATCGGGAGGTGTTGAGAGACCCCATATTGGGT

GCAAAAACTCTGGAGATTTTTCCGAAACTTGCTCCGGAGATGCAGAAATT
```

-continued

GTTAAGATGGACAAGAAGAAGCAGAACCTCCTTGTGAAAATGCACAATCG
CCTGAGAGATAGATTTGCTCGTGGTGCAGTGCCAGGTTTTGCACCAGCTG
CGAAAATGCCAATGCTTAAATGGAACGATGAACTGGCCAAATTGGCAGAG
TACAACGTGAGAACGTGCAAATTTGCCCACGATAAATGCCGCGCAATTGA
TGTCTGCCCCTATGCTGGACAGAATCTAGCTCAAATGATGTCCTATCCTA
CCCATCGAGATCTAAACTATGTTCTTAAGAATCTCACAAGGGAATGGTTC
TGGGAGTACAGATGGGCTAAGCAATCTCAGCTTGATAATTACGTGGGTGG
TCCTGGGAAAGACAACAAACAAATTGGACATTTCACAGCTTTTGTGCATG
AGAAAACAGACAAAGTTGGATGCGCTATAGCTCGATTTACAAATGAGCAC
AATTTTAAGGAGACCCTCCTAGCTTGCAACTACTGCTACACGAATATGAT
GAAGGAGAGGATCTACACGCAGGGAAAACCTTGTTCACAGTGTCAGAGCA
AAAAGTGTGGGCCAGTCTACAAGAACCTGTGTGATCCTTCGGAGAAGGTT
GATCCAACTCCTGATGTCCTTAAGCAATGGAAGCATGGAAAATGATTATT
AAGCTCACTTCAAATGTTTCCAATCCAAAAAAAAAAAAAAAAAAAAAAAA
AAAAA

LJL18

(SEQ ID NO: 4)

TTTTGAGAAAAACATTTCCTTGTGAGTTAAATAGTTGGTAAATTAAATCA
AGAGAATGTTGCTTCGTTCCTTGTTTGTTCTTTTTCTAATTTTCTTAACA
TTCTGCAACGCTGAGGAAGAACTTATTGAGAGAAAGTTAACAGGAAAAAC
GATCTATATCTCAACAATAAAGCTTCCGTGGTTCCAAGCTCTTAATCATT
GTGTTAAAAATGGCTACACAATGGTGTCAATTAAGACATTTGAAGAGAAT
AAAGAACTCCTTAAAGAACTCAAAAGGGTGATTAGGACAGAAGATACACA
AGTTTGGATTGGAGGCCTCAAACATCATCAATTTGCAAACTTTCGTTGGG
TAAGCGATGGAAGCCACGTAGCAACAGCTTCAGGGTACACCAATTGGGCC
CCAGGGGAGCCAGCTGATTCCTTCTATTACGATCAATTTTGCATGGCGAT
GTTGTTCAGAAAAGACGGCGCTCCGTGGGATGATTTGAATTGTTGGGTTA
AGAATCTTTTTGTTTGTGAGAAACGAGATGATTGAGAGGCTATTTTTGTT
ATCTCACCGTTTTGTTGAATAAAAAAGAAGAAGAAAGACAAAAAAAAAAA
AAAAAAAAAAAAAAAA

LJS193

(SEQ ID NO: 6)

TACTTCGTACTCTCAGAATTTCTTACAAGTTCCTTTTTCTCTTAACTTTT
AAAGTTTTATTTAACAAAATTGCTCCATTTTTTCGTTTTCTGAATATTCT
GTTGAAATTTTGATTAATCTATTTTATGTGCAGTTTTTACTAAAAATCCC
TTATCAGCAACCCGGTGTCTACAGTTTTGTCACGCTCAGTAGCATCTTCA
AGGTGGTAAGAAAAAATGAAACTCCTGCAAATCATCTTCTCTCTCTTCCT
GGTCTTTTTCCCGACCTCAAATGGGGCCCTGACCGGAAATGAAAGTGCAG
CAAATGCAGCTCCCTTGCCTGTCGTCCTGTGGCACGGGATGGGCGATTCT
TGCTGCTTTCCCTTCAGTTTGGGAAGCATAAAAAAATTAATTGAACAACA
AATTCCTGGGATTCATGTTGTTAGCCTGAAAATTGGAAAGTCTCTCATTG
AGGACTATGAAAGTGGATTTTTTGTTCATCCAGACAAGCAAATTCAGGAA
GTTTGTGAGTCACTTCAGAACGATCTAACACTCGCAAATGGATTCAATGC

-continued

AATTGGATTTTCTCAGGGTAGTCAGTTCCTGCGAGGTCTTGTGCAACGAT
GTTCTTCTATACAAGTAAGGAATCTCATTTCCATTGGAGGACAGCATCAA
GGGGTTTTTGGTCTGCCCTATTGTCCTTCGTTGAGCAGAAAGACTTGCGA
ATACTTTAGAAAGCTCCTGAATTATGCAGCTTATGAAAAAATGGGTACAGA
AACTCCTAGTTCAAGCCACCTACTGGCATGATCCTCTAAATGAGGATGCA
TATCGGACTGGAAGCACTTTCCTTGCTGATATAAATAATGAGAGACAAAT
CAATAATGACTATATTAATAATATTCGGAAGCTAAATCGTTTTGTGATGG
TAAAGTTCCTCAACGACAGCATGGTTCAGCCAATTGAATCTAGTTTCTTT
GGATTCTACGCTCCAGGAACTGATACAGAAGTTCTCCCATTAAAACAAAG
CAAGATTTATTTGGAAGATCGTTTGGGACTTCAATCAGTACCGATAGATT
ATCTAGAATGCGGAGGAGATCATTTGCAATTTACAAAAGAATGGTTCATA
AAGTTTATCATACCCTATCTGAAGCAATAAGAGCTGCAATGTAATTGATT
AAAAAATGTTAACCATTTCAGGATGATTGGGTGACCCCTTAAAAATATAA
ATGAAAAAATATACAAAAGAAATAAATTTTTATATTGATCCCACAAAAAA
AAAAAAAAAAAAAAAAAAAAAAA

LJS201

(SEQ ID NO: 8)

GGATCGGCCATTATGGCCGGGGCAGTTAATCGCCACAATTTAATAAAATG
AGGAACTTTGCTGTAGTCAGTTTAGCCGTTGCTGTCCTGCTCTTCTGTGC
ATGGCCTATAAATGCGGAAGATAATGAAGAAGTTGGAAAGGCGAGAGAAA
AAAGAGGCTTAAAAGACGCAATGGAACACTTCAAAAATGGATTTAAGGAG
CTGACAAAGGACTTTAAACTTCCAAGCCTTCCAAGTCTTCCTGGATTTGG
TAAAAAGCCTGAATCTGGAAGTTCTGAAGATTCTGGAGATAAAACTGAGG
ATACCAGTGGATCTAAGGACGACCAATCAAAGGATAATACGGTCGAAGAA
TCTTAAGAAAGGCGCAAATAGCTATTTTCAAAGTGGCGAATGTTTCTTTC
TTTATCTGAAATAAATATTTTTAAACCTTTCGAAACCAAAAAAAAAAAAA
AAAAAAAAAAAAAAA

LJL13

(SEQ ID NO: 10)

ACTTAAAGATTTTTGTTTAAGCAAAATGAACTTCTTGTTGAAAATTTTCT
CTTTGCTCTGTCTCTGTGGACTGGGGTATTCATGGCAGGATGTGAGAAAT
GCCGATCAAACCCTCTGGGCGTATAGATCGTGCCAAAAGAATCCTGAAGA
TAAGGATCACGTACCTCAATGGAGGAAGTTCGAATTACCCGACGATGAAA
AGACTCATTGCTACGTCAAGTGCGTATGGACGCGTTTGGGAGCTTACAAT
GAAAATGAAAATGTTTTCAAAATTGATGTCATTACTAAGCAATTTAATGA
ACGTGGCCTAGAAGTTCCGGCTGGACTTGATCAAGAATTGGGTGGTTCTA
CAGATGGAACTTGCAAAGCAGTTTACGATAAATCCATGAAGTTCTTCAAA
TCTCATTTTATGGACTTTAGGAATGCTTACTACGCAACTTATGACGGTTC
TGATGAATGGTTTAGCAAGAACCCTGATGTAAAACCGAAAGGAACAAAAG
TTTCCGAATACTGCAAAAATAAAGATGATGGAGATTGCAAACATTCCTGC
AGTATGTACTACTACCGCTTAATCGATGAAGACAACTTAGTTATTCCGTT
CAGCAACTTACCTGACTATCCCGAAGATAAGCTCGAGGAATGCAGGAATG

-continued

AAGCCAAGTCCGCAAATGAGTGCAAATCATCTGTTATCTATCAGTGTTTG
GAAAATGCGGATAAGTCAGCTTTAGACGCGTCTTTGAATATACTCGATGA
GTTTTCTGGAAGATATTAAAACAAACTGGATAAAAAACTTAGGCCAACCT
ATGATTCGAACTTACGATTTTGAACTTGAAATTCATGTGCTTTAACCTAT
TGTCCCACTAGGAAGAAAAATCCATATTTGGTGATGTTAAACTATTTTTG
AACCTCTTCAAAATAAACAATTTTCAAAAAAAAAAAAAAAAAAAAAAAAA
AAAAA

LJL23

(SEQ ID NO: 12)

AAAGAGAAGTAGTGAGAATGTTTCTTAAGTGGGTTGTTTGTGCTTTTGCG
ACTGTCTTCCTTGTTGGGGTGAGTCAGGCAGCCCCACCGGGGGTTGAATG
GTATCACTTTGGTCTGATTGCTGATATGGACAAAAAATCCATCGCGAGTG
ACAAAACCACCTTTAACAGCGTCCTAAAGATCGATGAATTGCGCCACAAC
ACAAAAACGGATCAATACATTTATGTGCGTAGTCGAGTGAAGAAGCCCGT
TTCCACGAGGTATGGGTTCAAAGGACGCGGTGCGGAATTGTCGGAAATTG
TTGTCTTCAACAATAAACTTTACACAGTTGATGATAAATCTGGAATTACG
TTCCGCATAACGAAAGACGGAAAACTCTTCCCGTGGGTTATTCTCGCAGA
TGCCGATGGACAGCGACCCGATGGCTTTAAGGGTGAATGGGCTACAATTA
AGGATGATACAATCTATGTTGGATCTACGGGGATGCTCAAGTTCACTTCA
TCCCTTTGGGTGAAGAAGATCACGAAAGATGGCGTTGTTACGAGTCACGA
TTGGACTGATAAATACCGAAAGATTCTCAAAGCTCTAAACATGCCAAATG
GTTTTGTCTGGCATGAGGCTGTTACGTGGTCTCCATTCAGGAAGCAATGG
GTCTTCATGCCGAGAAAGTGCTCAAGGCATCCCTTCTCACAGGAACTCGA
AGAACGCACAGGGTGCAATAAAATAGTGACGGCAGATGAGAATTTCAACG
ACATTCAAGTTATTCACATTCAAGATCAGCCATATAATTTAGCTTCTGGT
TTCTCTTCCTTCCGCTTTATTCCTGGTACGAAAAATGAAAGACTTCTCGC
CTTGAGGACAGTAGAGCAGGAAGATCAGGTTAAAACTTGGGCTGTGGTCA
TGGATATGAAAGGAACAGTTCTGATGTACGAAAAGGAACTTTATGACGAA
AAATTCGAAGGTTTAGCATTCTTTGGTGGTATTAAAAAGAATTAATTTGT
TCCAGAAGCTTTTAGATGAAATAATAAATTTTATTTCATTTTAAAAAAAA
AAAAAAAAAAAAAAAAAAAAA

LJM10

(SEQ ID NO: 14)

CGCGGCCGCGTCGACCGACAGAAGGGGTAGTTTGTAGAGAACTTTGAGTT
CTAAAGGAAATTCTCAAGAAGAAAATATTCAAAAGTAAAGAATGGCGTTG
AAGTTTCTTCCGGTTCTCCTTCTAAGCTGCTTCGCAATGAGCACGGCACT
ACAAGTTACTGAGAAGGAACTTTCTGATGGGAAAAAGATCTTCATCTCCA
AAGTTGAGCTAAACTGGTTCGAAGCTCTTGATTTCTGTATCCATCGTGGT
CTTACGTTGCTCTCAATTAAATCCGCCAAGGAAAATGTAGACGTAACAAA
AGCAATTCGGGCTGAATTGAATTTTGATTCAAAGAAATTGGCTCATGTGT
GGACTGGAGGTATTCGCCATAGTCAAGATAAGTATTTCCGTTGGATAAAT
GATGGAACTAAAGTTGTTAAACGAGTCTACACCAATTGGTTCACTGGAGA
ACCAAATAATGGTTACTGGAAGGATGAATTTTGTCTGGAAATTTACTATA

-continued

AAACCGAAGAAGGGAAGTGGAATGATGATAAATGTCACGTGAAGCATCAT
TTTGTATGTCAAGAAAAGAAATAAATTGATTGATTTTGTTTGCTGATTTG
CAGTTCAGAATTGAAAAGCCAAAAAAAAAAAAAAAAAAAAAAAAAAAA

LJL143

(SEQ ID NO: 16)

CTTCTTTGGATTTATTGAGTGATTAACAGGAAATTAGCTGAAGAAATGAA
TTCGATTAATTTCCTATCAATAGTTGGTTTAATCAGTTTTGGATTCATTG
TTGCAGTAAAGTGTGATGGTGATGAATATTTCATTGGAAAATACAAAGAA
AAAGATGAGACACTGTTTTTTGCAAGCTACGGCCTAAAGAGGGATCCTTG
CCAAATTGTCTTAGGCTACAAATGCTCAAACAATCAAACCCACTTTGTGC
TTAATTTTAAAACCAATAAGAAATCCTGCATATCAGCAATTAAGCTGACT
TCTTACCCAAAAATCAATCAAAACTCGGATTTAACTAAAAATCTCTACTG
CCAAACTGGAGGAATAGGAACAGATAACTGCAAACTTGTCTTCAAGAAAC
GTAAAAGACAAATAGCAGCTAATATTGAAATCTACGGCATTCCAGCGAAG
AAATGTTCCTTCAAGGATCGTTACATTGGAGCTGATCCACTCCACGTCGA
TTCCTATGGGCTTCCGTATCAGTTTGATCAGGAACATGGATGGAATGTGG
AACGATATAACATTTTCAAAGACACAAGATTTTCCACAGAAGTTTTCTAC
CACAAAAATGGTTTATTTAACACCCAAATAACTTATTTGGCTGAAGAAGA
TTCCTTCTCTGAAGCTCGAGAGATTACTGCGAAGGATATTAAGAAGAAGT
TTTCAATTATTTTGCCCAATGAAGAGTATAAGAGGATTAGTTTCTTGGAC
GTTTATTGGTTCCAGGAGACTATGCGAAAAAAGCCTAAATATCCCTACAT
TCACTACAATGGAGAATGCAGCAATGAGAATAAAACTTGTGAACTTGTCT
TTGACACCGATGAACTAATGACCTACGCCCTTGTTAAAGTCTTTACTAAT
CCTGAGAGTGATGGATCTAGGCTCAAAGAAGAGGATTTGGGAAGAGGATA
AATCTTCTTAATAAAAAAAAGTTCTGTAAGAAAATATTGTTCAATAAATT
AAAAAAAAAAAAAAAAAAAAA

LJS142

(SEQ ID NO: 18)

AATAGATCTTCAAAACGTCTAAGAATGGCTTTCAGCAACACTTTATTTGT
TCTTTTTGTGAGTTTTTTAACGTTTTGTGGCGCTGATCAGACACTTATTG
AGAAGGAATTAACCGGAAGAACTGTTTATATCTCCAAAATTAAGCTAAAT
TGGAACGATGCCTTCGATTACTGCATCCGCAATGGCCTCACCTTTGCTAA
GATTAAATCAGCTGAAGAAAACACCGAACTGAGTGAGAAACTCAAGACAG
TCATTCGTACGGAGGAGTTTCAAGTTTGGATTGGAGGCATTGAACATCAT
CAAGACAGTTCCTTCCGCTGGGTAAGCGACTCCCAACCAATAACCAACAA
ATTGGGCTACAAATACACAAACTGGAATACCGGAGAGCCCACAAATTACC
AAAACAACGAATATTGCTTGGAAATATTATTCCGGAAGGAAGATGGAAAA
TGGAATGATTTTCCCTGCAGTGCAAGACATCATTTTGTTTGTGAAAAAAG
AACAAAATAAAATGAAGAAAATGTGATTTTCCTTTGGTTGAAGAATAAAA
TTCTGTTGAAAAAAAAAAAAAAAAAAAAAAAAAAAA

-continued

LJL17

(SEQ ID NO: 20)

ATTTAGTTTGTGTTTAACAAAACAAGAATGCAGAACTTCCTTTTAGTTTC
CTTGGCTTTAGCTGCCTTAATGCTATGTGCCGAAGCAAAGCCGTACGATT
TTCCGCTTTATCAGGACTTAATTCAGGGCGTTATTCAGCGCGAAAGTCAA
GCTGAGAGGGAGAAGAGAAGCCCCAATGAGGACTATGAGAAGCAATTTGG
GGATATTGTTGATCAAATTAAGGAAATTAGTTTCAATGTCATGAAAATGC
CCCATTTTGGAAGCTCTGATGATAATCGTGATGATGGCGAGTACGTTGAT
CATCATTATGGTGACGAAGATGATCGTGATTATGATCATTACTAAATACT
ACTTGCTCCTGCTGAATGACTTGAAGGAATCATTTTTTTGCAAAAATATC
CATCAAATTATTGAATTAATAAAGTTGCAAAAAAAAAAAAAAAAAAAAAA
AAAAAAA

LJM06

(SEQ ID NO: 22)

GTTTAAGGAATTTCTTTCATCTCAGTCTTCGATTTTCTTTAAACAAATAA
TGAAGTTTTATATTTTTGGAGTTTTCCTGGTGAGCTTTCTTGCATTATGC
AATGCTGAGGATTATGATAAAGTAAAACTTACTGGAAGAACTGTTTACAT
CTCCAGATCAAAGGCTCCGTGGTTCACAGCTTTAGACAATTGTAATCGTT
TACGCTTCACCTTCGCCATGATCAAGTCTCAGAAGGAGAATGAAGAGCTA
ACAAATGCGCTTTTAAGTGTAATTAAATCTGACGAAGAAAATGTTTGGAT
TGGAGGTCTTAGGCACGATCTGGATGACTACTTCCGTTGGATTAGTTTTG
GAACTGCATTGTCAAAGACTTCGTACACCAATTGGGCCCCAAAGGAACCC
ACAGGAAGGCCCCATAGAACTCAAAATGATGAATTCTGCATGCAAATGTC
TTTCAAAGATGGTGGCAAATGGAGTGATAACACCTGTTGGCGTAAACGTT
TGTACGTTTGTGAAAAGCGTGATTAAATAAAGGAACACTGCCAATGAATA
TTGGGCAATTTGAGAGAAATTAAATTAAAAAAAAAAAAAAAAAAA

LJM17

(SEQ ID NO: 24)

AGTCAGTGTTAATGAAGAAATTGCAATTATGAGGTTCTTCTTTGTTTTCC
TTGCCATCGTCCTTTTTCAAGGGATCCACGGAGCTTATGTGGAAATAGGA
TATTCTCTGAGAAATATTACATTCGATGGATTGGATACAGATGACTACAA
TCCAAAGTTCAACATTCCAACGGGTTTGGCAGTTGATCCCGAAGGATATA
GGCTCTTCATAGCCATCCCAAGGAGAAAGCCAAAGGTTCCCTACACTGTG
GCTGAACTGAATATGGTCATGAATCCCGGATTTCCCGTCGAGAGAGCTCC
GAGCTTTGAGAAATTCAAAAAATTCAATGGCGAGGGCAAAAAGGATCTTG
TTAATGTGTATCAGCCAGTCATTGATGATTGTCGTCGTCTTTGGGTGCTT
GACATTGGGAAGGTGGAATACACCGGTGGTGATGCTGATCAATATCCCAA
AGGAAAGCCTACCCTAATTGCCTACGACCTCAAGAAGGATCATACTCCGG
AAATTCATCGATTTGAAATTCCAGACGATCTCTATAGCTCACAAGTTGAA
TTTGGTGGATTTGCCGTTGATGTTGTTAACACGAAAGGAGACTGTACGGA
GTCATTTGTCTACCTGACCAATTTCAAGGATAACTCTCTAATTGTCTACG
ATGAGACACAAAAGAAAGCTTGGAAATTCACAGATAAAACATTTGAAGCT
GATAAGGAATCCACGTTCTCCTACTCGGGAGAGGAACAAATGAAGTACAA
AGTCGGTCTTTTTGGGATAGCTCTGGGTGATAGGGATGAAATGGGGCATC

-continued

GTCCTGCCTGCTACATCGCTGGGAGTAGCACCAAAGTCTACAGTGTTAAC
ACTAAAGAACTCAAAACAGAGAATGGTCAGTTAAATCCTCAGCTTCACGG
TGATCGTGGAAAGTACACAGATGCAATTGCCCTAGCCTACGATCCTGAGC
ATAAAGTCCTCTACTTTGCTGAATCCGACAGCAGGCAGGTGTCCTGTTGG
AATGTAAATATGGAGCTAAAACCAGACAATACGGATGTGATCTTCTCTAG
TGCCCGTTTTACTTTTGGAACGGATATTTTGGTTGATAGCAAGGGAATGC
TGTGGATAATGGCTAATGGACATCCACCAGTAGAGGATCAAGAGAAGATT
TGGAAGATGAGATTCGTAAACCGGAAGATCCGTATTATGAAAGTGGATAC
GGAACGTGTTTTCAAATATTCACGCTGCAATCCAAATTATAAGCCCCCAA
AGGAAATTGAAGTTTGAGACACAGGAAAAAGCTCAATTTTCAACAAGAAT
TTGATCTTAATCTGAATACCCTAAAGTCTGTCAAAGAATTTCATATTATT
TGAAAACCAATAAATTGATTAATTTTCCGAAAAAAAAAAAAAAAAAAAAA
AAAAAAAAA

LJL04

(SEQ ID NO: 26)

ACTAAAGCGTCTCACCGAAATCAGGGAAAATGATTAAGGAAGTTTTCTCT
CTGGCTCTACTTGTGGCCTTGGCACAGTGTGCTAATGAAATCCCTATTAA
TCGTCAGGGGAAAGATTATCCAGTTCCGATCATTGATCCAAATAAATCAT
CTTCGGATGATTATTTCGATGATCGCTTCTACCCTGATATTGATGATGAG
GGCATAGCTGAGGCTCCTAAGGATAATAGGGGAAAATCCCGTGGTGGTGG
TGCGGCTGGCGCAAGAGAAGGTAGGTTAGGTACGAATGGGGCTAAACCGG
GTCAGGGTGGAACTAGACCAGGACAGGGTGGAACTAGGCCAGGACAGGGT
GGAACTAGGCCAGGTCAGGGTGGAACTAGGCCAGGTCAGGGTGGAACTAG
ACCTGGGCAAGGTAGAACTAAGCCTGCTCAGGGAACTACTAGGCCAGCTC
AGGGAACTAGAAATCCAGGATCGGTTGGTACGAAAGAAGCCCAGGATGCG
TCAAAACAAGGTCAAGGTAAAAGAAGGCCAGGGCAAGTTGGTGGTAAAAG
ACCAGGACAAGCAAATGCTCCTAATGCAGGCACTAGAAAGCAACAGAAAG
GCAGTAGAGGCGTTGGAAGGCCTGATCTATCGCGCTACAAAGATGCCCCT
GCTAAATTCGTTTTCAAATCTCCCGATTTCAGTGGAGAAGGCAAAACTCC
AACTGTAAATTACTTTAGAACGAAGAAGAAGGAGCACATTGTGACCCGTG
GTAGTCCTAATGATGAATTTGTTCTGGAGATTCTCGATGGGGATCCAACT
GGGCTTGGACTAAAGAGTGAAACCATAGGCAAAGATACGCGTTTAGTGCT
GGAGAATCCTAATGGAAATTCCATCGTGGCTCGTGTTAAGATCTACAAGA
ACGGTTATTCAGGATGAAGAAGAAATCCTTTGATTTCCCCCCCCCCCTCT
TCCTTTAAAATTCAACATAATAAAAAAAAAAAAAAAAA

LJM114

(SEQ ID NO: 28)

GTCTTTTCCTGAGTGTTTCATTAACAAAATGAATTCAGTAAACACTTTAA
TTTTAACTCTTCTATTTGCAATTTTTTTATTAGTGAAAAGGTCTCAGGCT
TTTCTTCCATCTGACCCAAGTATCTGTGTTAAAAATTTAGTATTGGATAC
AGGAAGGACTTGTGAGGAAAGTGAATATTTTCCGGATATCAAGAACGTTA
AAAATGGAAAAAGAGTTTACATTGTCTGCACTGATTCAGATGCAGTTGAT

-continued

TATAAATTTTATATTTGTTTCGATATGAATCGTCTTTCTGGACCACCGTA
TCCTGAGGAAGAAATCCTTCGTGAATCAACGGTAACTTATGCCCAAATTT
ATGAGCTGATGACTACGGAAACCACTGAAACCAAAAAGCCAAAAAAGAAA
CCAAAGAATTCAAAAACGGACCCAGACCCTCCAGCAATTCGTCCAGGATT
TTCATTTAGAAATTCAATTTCTGTTTAATTTTACAATTTATTTTGAAAGA
AAAATGATATTTCGAAATATTCTATACAAAAAAACAACAGTTATAAAACG
AAAATTCAATCATTTCAATGAGAAAACTTAGTCTTGAGTAAGGTTTATTC
ACCACCCGACGCCACGCTATGGTGAATAATTTTCTTTATTCACCACATCA
AAATGACGGCTTATAAACTTCAACAAATAGTTTGGAAAATACATTTCTAA
CTAATGCAATGTTTACTTAAAATCACTTTACAAATTCACGCATTTGAGAT
GCAACAAATATATACAATTCAACGATATAAACTTTCCACAAGGAAAACTT
TCAACCAAAAAAAAAAAAAAAAAAAA

LJM111

(SEQ ID NO: 30)

ATCATTCAAAAGGCAGCAGCACAATGAAGTTATTTTTCTTTCTTTACACT
TTTGGTCTAGTCCAAACGATTTTTGGAGTAGAAATTAAACAAGGATTTAA
ATGGAATAAAATCCTTTATGAGGGCGATACATCAGAAAACTTCAATCCAG
ATAACAACATCCTTACGGCTTTTGCGTACGATCCTGAGAGTCAGAAACTC
TTCCTAACTGTCCCGAGGAAATATCCCGAAACTATGTACACTTTGGCAGA
AGTTGATACTGAGAAAAATTCTTTTGAATCGGGAGATACTTCCCCGCTCC
TTGGAAAATTCAGTGGTCATGAAACTGGGAAAGAACTTACATCAGTTTAT
CAGCCAGTTATCGATGAATGTCATCGTCTTTGGGTTGTTGATGTTGGATC
AGTAGAACGTAACTCAGACGGCACAGAAGGTCAGCCAGAACATAATCCTA
CCCTTGTGGCGTACGATCTCAAAGAAGCCAACTATCCTGAAGTTATTCGT
TACACGTTTCCCGATAATTCCATTGAGAAGCCCACATTTCTGGGTGGATT
TGCCGTTGATGTTGTAAAGCCGGATGAATGCAGTGAAACTTTTGTCTACA
TCACAAACTTCCTCACCAACGCCCTCATAGTATACGATCATAAGAATAAG
GACTCCTGGACGGTACAAGATTCAACTTTTGGACCAGATAAAAAGTCAAA
GTTTGACCACGATGGACAACAGTATGAATACGAAGCAGGAATCTTCGGGA
TTACCCTTGGAGAGAGAGATAACGAAGGAAATCGTCAAGCGTACTATTTA
GTAGCAAGTAGTACCAAACTTCACAGCATCAACACCAAAGAACTGAAGCA
AAAAGGAAGCAAAGTTAATGCAAATTATTTGGGAGATCGTGGTGAATCCA
CCGATGCCATAGGCTTAGTTTACGATCCAAAAACCAAAACTATCTTCTTC
GTTGAGTCAAATAGCAAAAGAGTATCATGCTGGAATACCCAGGAAACACT
AAACAAGGATAAAATTGATGTAATCTATCACAATGCAGACTTTTCCTTTG
GAACAGATATATCGATTGATAGTCAGGATAATTTGTGGTTCCTAGCAAAT
GGACTTCCACCTCTGGAAAATTCTGATAAATTTGTCTTTACAAAGCCACG
TTATCAAATATTCAAAGTCAACATTCAAGAAGCAATTGCTGGAACTAAAT
GTGAAAAGAATCTTTAACAAATGAAACTTTGTAGAAAAATACATAATATC
TGAATAAAAAGTCATAAATGTACCATAAAAAAAAAAAAAAAAAAAAAAAA
AAAAAAAAAAAAAAAAAAAAAAAA

-continued

LJM78

(SEQ ID NO: 32)

CTTTAAAGCAAAAATTTTGTGGGAAAGGAAGTTACCCGGAGATGACGTTT
CTAATTATACTTGGTGCATTTCTCCTTGTTCAAATTATTACAGCTTCAGC
TTTAGGATTGCCTGAACAGTTTAAAGGTTTAGAGGATTTACCTAAAAAAC
CTTTGGCAGAGACTTATTATCACGAAGGATTGAATGATGGAAAAACGGAT
GAAATGGTGGATATTTTTAAAAGTCTTAGCGATGAATTTAAATTCAGTGA
TGAAAATTTAGATGTTGGTGAGGAGAAAAATTACAAGAAACGTGATATAA
CCCAAAATTCAGTGGCAAGGAACTTCCTATCAAACGTAAAGGGAATTCCT
TCAATGCCATCACTCCCTTCAATGCCTTCAATGCCATCAATTCCTTCACT
TTGGTCAAGTCAGACACAGGCGGCACCAAATACCGCACTTGCCCTTCCTG
AATCTGATTATTCCCTTCTAGATATGCCGAATATTGTGAAAAATTTCCTA
AAGGAAACAAGAGACCTCTATAACGATGTTGGAGCTTTTCTTAAGGCAAT
TACAGAAGCTTTAACAAATAGATCTTCATCATCTCAACTTCTTTCCTCCC
CAATGGTGAGCACGAATAAAACCAAAGAATTTATTCGGAATGAAATACAA
AAAGTCCGAAAAGTGAGAAATTTCGTCCAGGAAACTCTTCAGAAAATCCG
AGACATTTCTGCTGCTATTGCCAAAAAGGTAAAATCATCAGAATGTCTGT
CCAATCTTACGGACATCAAAGGACTTGTATCAGACGGAATTAATTGTTTA
AAGGAAAAAATTCAATGATGGAAAACGAATTATCCTGCAATTGTACAATAA
TTTACTAAAAGGACTCAAAATTCCAAATGACCTAATGGTTGAATTGAAGA
AATGTGATACAAATCAAAACAATACTTTGGGAAGAATAATCTGTTATTTT
TTGACACCATTGCAACTGGAAAAAGAACAAATTCTTCTACCTGTAGAATT
TATAAAGCGCATTCTTGAATTAACCCACTACTTTTCCACAATGAAAGAAG
ATCTTATCAACTGTGGCATCACAACGATTGCATCCATTACGTAAAAAATG
GAAAAATGTGCCGGTGAAATGCTTGAAATCACCAAAGAAATTTCATCGCA
AATAACAGTTCCAGAATAACCAAATTTTAATGATTACTTCTCAAGGAAAA
TACTACCAAAAGGCATTAATTAAAACGATGTTTTTTATAAACAATGTAAG
AAAAAAAAAAAAAAAAAAAAAAAAA

LJS238

(SEQ ID NO: 34)

AGTTAATCTTCTGTCAAGCTACAAAAATGCTTAAAATCGTTTTATTTCTA
TCAGTTTTGGCTGTATTAGTGATTTGTGTAGCAGCAATGCCAGGATCCAA
TGTTCCTTGGCACATTTCACGAGAAGAGCTTGAGAAGCTTCGTGAAGCTC
GAAAGAATCACAAGGCACTCGAGAAGGCAATTGATGAATTAATTGACAAA
TATCTCTGATTTTGAAGAGCAAGGAAGAGGAAATAAACGGCCGAGGAAGG
ATTTTCTTTAGAGATTCTTCTTTTTATTACTTCAAACCTAACTTCAAAAT
CAGTCTGATATTTTTTTAATTTGAAAAAAATATTGAAAATTTTAACTATT
TGTGAAATTTAAATAAATAAAGAATGTCAGAAGCAAAAAAAAAAAAAAAA
AAAAAAAAAAAA

LJS169

(SEQ ID NO: 36)

AATTTTCACCATGAAGTTTTCTTGCCCAGTTTTCGTTGCAATTTTCCTTT
TGTGCGGATTTTTATCGTGTTGAGGGGTCATCACAATGTGAAGAAGATTTA
AAAGAAGAAGCTGAAGCTTTCTTTAAGGATTGCAATGAAGCAAAAGCCAA

-continued

TCCTGGTGAATACGAGAATCTCACCAAAGAAGAAATGTTTGAAGAATTGA

AAGAATATGGAGTTGCTGACACAGACATGGAGACAGTTTACAAACTTGTG

GAAGAATGTTGGAATGAATTAACAACAACGGATTGTAAGAGATTTCTCGA

AGAGGCTGAATGCTTCAAGAAGAAGAATATTTGTAAATATTTCCCAGATG

AAGTGAAATTGAAGAAGAAATAAATTTTTAGCTTGAAAAAAAAAAAAAAA

AAAAAAAAAAAAAAAAAAAAAAAAAAAA

LJL11

(SEQ ID NO: 38)

AGTTGCAAGAATTTCTTCATTGCGTTAAGATGTTGTTTTTCCTTAACTTT

TTTGTGCTGGTGTTCAGCATAGAACTGGCGTTGTTAACAGCATCAGCAGC

AGCAGAAGACGGCAGCTATGAGATCATAATTCTTCACACCAATGATATGC

ACGCGCGTTTTGATCAAACCAATGCTGGAAGCAACAAATGCCAAGAAAAA

GACAAGATTGCTTCCAAATGCTACGGAGGATTTGCAAGAGTTTCAACAAT

GGTGAAAAAATTCCGAGAAGAAAATGGCAGCAGTGTCTTGTTCTTGAATG

CTGGTGACACGTATACAGGTACCCCATGGTTTACCCTCTACAAGGAGACC

ATTGCAACGGAGATGATGAACATCCTTCGTCCAGATGCAGCCTCACTGGG

AAATCATGAATTCGACAAAGGAGTAGAAGGACTCGTGCCATTCCTCAATG

GTGTCACCTTCCCTATTTTAACAGCGAATTTGGACACTTCTCAAGAGCCA

ACAATGACCAATGCTAAAAATCTCAAACGCTCAATGATTTTTACGGTTTC

CGGGCACAGAGTTGGTGTAATTGGCTACCTAACGCCTGATACAAAATTCC

TCTCGGACGTTGGTAAAGTTAATTTTATTCCGGAAGTTGAAGCCATCAAT

ACGGAAGCACAGCGTCTGAAGAAAGAGGAAAATGCCGAAATAATCATCGT

TGTTGGACATTCAGGGTTGATAAAAGATCGAGAAATTGCAGAGAAATGCC

CACTGGTTGACATAATTGTTGGAGGACATTCACACACATTCCTCTACACA

GGAAGTCAGCCTGATCGTGAGGTTCCTGTAGACGTTTATCCTGTTGTTGT

GACCCAATCCAGTGGGAAGAAAGTTCCAATTGTTCAAGCCTATTGCTTTA

CAAAGTATTTGGGGTACTTTAAAGTGACGATCAACGGAAAAGGAAATGTT

GTGGGATGGACTGGGCAGCCAATTCTCCTTAATAACAACATTCCCCAAGA

TCAGGAAGTTCTCACTGCTCTTGAAAAGTACAGAGAACGCGTGGAAAACT

ATGGAAATCGCGTAATTGGAGTTTCCCGTGTAATTCTCAATGGGGGGCAT

ACTGAATGTCGTTTCCATGAATGCAATATGGGTAATCTCATCACGGACGC

TTTTGTGTATGCCAATGTAATCAGTACACCAATGAGTACGAATGCCTGGA

CAGATGCAAGTGTTGTTCTGTATCAAAGTGGTGGCATTCGTGCCCCAATT

GATCCTCGTACCGCGGCAGGGAGCATCACACGCCTCGAGTTGGACAATGT

TCTACCATTTGGGAATGCACTGTACGTCGTAAAAGTTCCTGGGAATGTCT

TACGCAAAGCTTTGGAACATTCAGTTCATCGATACTCCAACACTTCGGGA

TGGGGAGAATTTCCACAAGTTTCGGGGCTAAAGATTCGTTTTAACGTCAA

TGAAGAAATTGGAAAACGCGTAAAGTCCGTTAAAGTTCTCTGTAGCAATT

GCTCTCAACCTGAATACCAACCACTGAGAAATAAAAAAACTTACAACGTT

ATCATGGACAGTTTTATGAAGGATGGAGGTGATGGGTATAGCATGTTCAA

GCCCTTGAAGATCATCAAGACCCTCCCACTGGGAGATATTGAAACAGTAG

AAGCTTATATTGAGAAAATGGGCCCCATTTTCCCAGCAGTCGAGGGAAGG

-continued

ATCACTGTTCTTGGGGGACTTCAAAAATCAGATGAGGATTGGCATTAGAA

ACATCCTGGACGTTATGGAAAGAATAAAAGAAGGATCATAGAAAAAAAAA

AAAAAAAAATAAAAAAAAAAAAAAAAAAAAAAAAAAAAA

LJL08

(SEQ ID NO: 40)

GTCAGTGATCTGATAAGTTATTAAAATGAAGCAAATCCTTCTAATCTCTT

TGGTGGTGATTCTTGCCGTGCTTGCCTTCAATGTTGCTGAGGGCTGTGAT

GCAACATGCCAATTTCGCAAAGCCATAGAAGACTGCAAGAAGAAGGCGGA

TAATAGCGATGTTTTGCAGACTTCTGTACAAACAACTGCAACATTCACAT

CAATGGATACATCCCAACTACCTGGAAATAATGTCTTCAAAGCATGCATG

AAGGAGAAGGCTAAGGAATTTAGGGCAGGAAAGTAAGAGATTGAGGAAAA

TTGTAGCCGAAGAGAGAAGGAAGGAAAGTCCCATATTTTGTTTGTTAATT

GTAACGAATTTTGCGAAAAAAATAAAATATTATGCACTCCAAAAAAAAAA

AAAAAAAAAAAAAAAAAAA

LJS105

(SEQ ID NO: 42)

TATTTTTAATAATTCTGTGTAAAATGAACGTTCTTTTCGTGTCTTTCACG

CTCACAATTCTTCTTCTCTGTGTTAAGGCACGGCCAGAAGATTTCGTAGC

TCTTCAGGATCAAGCTAATTTCCAGAAATGCCTCGAACAATATCCAGAAC

CAAATCAATCTGGAGAAGTTCTTGCGTGCCTCAAGAAGCGCGAAGGTGCC

AAAGATTTCCGGGAAAAGAGGAGCCTGGATGACATAGAAGGGACTTTCCA

AGAGTCTGGAAATCTCTGGGGTGCATAGGAAGCTCAGAGGACTTCTAATC

AATCTGTGAGAAGAGAACCCAACGGCTAGAGAAAATTTAAGGAAAATAAA

GAAATTAATGAAGCATTAAAAAAAAAAAAAAAAAAAAAAAAAAAAAAAAA

AAAAAAAAAAAAAAAAAAAAAAAAAAAAA

LJL09

(SEQ ID NO: 44)

GTATATCAAGTATCATTCAAGTGAATCATTGGCTCCGTAATTTGTACAAA

AGAAAAAAAAAGTTGATAAAATCATGAAAATCACTGTGATTTTATTCACG

GGATTTACAATTGCCCTCGTGAGTAGTGCTGTGCTTAAGAAAAACGGTGA

AACTATTGAAGAAGAAGAAGTAAGAGCTGAGCAACGACTTAGAGAGATCA

ATGAGGAACTTGATCGTAGGAAGAATATCAATACTGTAGCCGCTTGGGCT

TATGCATCCAATATTACTGAGGTCAATCTCAAGAACATGAATGATGTGTC

GGTTGAAACCGCGAAATACTACAAGGAACTTGCATCTGAATTGAAGGGAT

TCAATGCCAAGGAATACAAGAGTGAGGATCTGAAGAGACAAATTAAGAAG

CTAAGCAAGTTGGGATATAGTGCTTTACCATCTGAGAAGTATAAGGAGCT

TTTGGAAGCTATCACATGGATGGAATCGAATTATGCAAAAGTGAAAGTTT

GCTCATACAAGGATCCAAAGAAATGTGATTTAGCACTTGAACCTGAAATT

ACGGAAATCCTTATTAAAAGTCGAGATCCTGAGGAACTTAAATATTATTG

GAAACAATGGTACGACAAAGCTGGCACACCAACTCGAGAGAGTTTTAATA

AGTATGTACAACTAAATCGTGAAGCAGCGAAATTGGATGGATTTTATTCG

GGTGCAGAATCTTGGCTTGATGAATATGAAGATGAGACATTTGAGAAACA

ACTTGAGGATATCTTCGCCCAAATTCGCCCACTGTACGAGCAACTCCATG

-continued

CTTATGTTAGATTCAAGCTGAGGGAAAAGTATGGAAATGACGTTGTTTCG

GAGAAAGGTCCCATTCCAATGCATCTCTTGGGGAACATGTGGGGTCAAAC

GTGGAGTGAAGTTGCCCCAATTTTAGTCCCATACCCCGAAAAGAAGCTCC

TCGATGTTACCGATGAGATGGTTAAGCAGGGATACACACCAATTTCTATG

TTTGAAAAAGGAGACGAATTTTTCCAAAGCTTGAATATGACGAAACTTCC

AAAAACCTTCTGGGAGTACAGTATTTTGGAAAAACCCCAAGATGGTAGGG

AATTGATCTGCCATGCAAGTGCATGGGACTTCTATACAAAGGATGATGTA

AGGATTAAACAGTGTACCAGAGTTACAATGGATCAATTCTTCACGGCTCA

TCATGAGCTTGGTCACATTCAATATTATTTGCAATATCAACATTTGCCGA

GTGTTTACAGAGAAGGTGCCAATCCAGGCTTTCACGAGGCTGTTGGGGAT

GTTCTCTCTCTTTCGGTATCAAGTCCTAAACATTTGGAAAAAGTTGGTTT

GCTTAAAGACTTCAAATTTGATGAAGAATCCCAGATAAATCAACTTCTAA

ATTTAGCTCTGGATAAAATGGCATTCCTCCCATTTGCCTATACCATTGAT

AAATATCGCTGGGGTGTGTTTCGGGGTGAAATTTCGCCGTCTGAGTACAA

TTGCAAATTTTGGGAAATGCGTTCCTACTATGGTGGTATAGAACCACCAA

TTGCACGTTCTGAGAGTGATTTTGATCCACCAGCAAAATATCATATTTCA

TCGGATGTTGAGTACCTCAGGTATTTGGTTTCCTTCATTATTCAGTTCCA

ATTCCATCAAGCTGTGTGCCAAAAGACTGGTCAGTTCGTACCGAATGATC

CGGAGAAGACTCTTCTAAATTGTGACATCTACCAGAGTGCTGAGGCTGGT

AATGCCTTCAAAGAAATGCTCAAATTGGGATCCTCAAAACCATGGCCAGA

TGCAATGGAAATTCTTACGGGGCAAAGGAAAATGGATGCTTCTGCATTAA

TTGAGTACTTCCGTCCACTCAGTGAGTGGTTGCAGAAGAAGAATAAGGAA

CTAGGAGCTTATGTTGGCTGGGACAAATCTACTAAGTGTGTCAAAAACGT

CAGTTAATTTTTTGTGAGCCCTAAAAAATATTCATAACATTTCAATATGA

CAAAATATATGATTTTCGTGAAAACTAAGCATGAGTAAGTTTTTTTGTG

AATTTTTAGCAGTTTCATTTCAGAATAAACGTCAAATTTTTAAAAAAAAA

AAAAAAAAAAAAAAAAAAAA

LJL38

(SEQ ID NO: 46)

TCAGTTAGTTGACTAACAAACCACAATAGAGACACTAAAATGAAGACATT

CGCCTTAATCTTCTTGGCTCTTGCTGTTTTTGTGCTCTGCATTGACGGAG

CTCCAACTTTTGTGAATTTACTGGACGACGTACAGGAAGAGGTAGAAGTT

AATACGTATGAGCCTTAGGAAGAAAATGTTTGAGGAGTTTCAGGCAGAGG

CAGAGCTTTCCCAGAGAGGGAGCTTTTGCCTTGCTGTAGATTTTTAAAAA

TGAATCAATTTGATTGGAGCAATTACGCTATATTTGTGGGAATATTTTTG

AATTAAAAACTAATTATGGAAATTAATATATAATTTTCAGAATTTCAATA

AATTCATCAAAATTGTATTAATTAAAAAATATTGTATGAAATTCCCAATA

AAAGCTTTCAAATTAAAAAAAAAAAAAAAAAAAAAAAAAAAAAAAAAAAA

AAAAAAAAAAAA

LJM04

(SEQ ID NO: 48)

GGCCATTATGGCCGGGGATAGAACTTAATTGTTGTTAAAATGAATCACTT

GTGCTTTATTATTATTGCTCTATTCTTTTTGGTTCAACAATCTTTGGCTG

-continued

AACATCCAGAAGAAAAATGTATTAGAGAATTGGCGAGAACTGATGAAAAC

TGCATTCTTCATTGTACGTATTCGTACTACGGATTCGTTGATAAAAATTT

CAGGATCGCTAAAAAACATGTTCAAAAATTCAAAAAAATCCTAGTTACAT

TCGGCGCTGTTCCTAAGAAAGAAAAAAAGAAACTTTTAGAGCACATTGAG

GCTTGTGCGGATTCTGCGAATGCTGATCAACCTCAAACTAAAGATGAAAA

ATGTACAAAAATAAATAAGTACTATCGTTGTGTTGTGGATGGAAAAATAT

TACCCTGGAATAGTTATGCTGATGCAATCATTAAGTTTGATAAAACCCTT

AACGTATGAAGCAAAGATATTCGAAAAAAAAACATCAAGATTATGCTGGA

AAGAAAAAAATAAAAAAAAATTGTGCTAATCAAATTGAATTAACGCTTAA

TGCTATATTAAAAAAAAAAAAAAAAAAAA

LJM26

(SEQ ID NO: 50)

GTCGGAGATCGTCTGCCTTGATGATCACATCGTGATTGTGAGTTACAAGA

GTGAAACTTTTTAAGTGTGTGTGTCTTAGCAAAGTGATTTCCACAATGAA

GATTATTTTTTTAGCCGCTTTTCTACTAGCGGATGGTATTTGGGCTGCTG

AAGAACCTTCAGTGGAAATTGTAACACCACAATCAGTGCGGAGACACGCT

ACGCCAAAAGCCCAGGACGCGAGGGTAGGAAGTGAATCCGCAACAACAGC

ACCAAGACCAAGTGAATCAATGGATTACTGGGAGAATGATGATTTCGTCC

CATTTGAGGGTCCATTCAAGGATATTGGAGAATTCGACTGGAACCTTTCG

AAGATCGTTTTTGAGGAAAACAAAGGTAATGCCATCTTGTCGCCACTCTC

TGTGAAGCTACTAATGAGTTTGCTCTTCGAGGCCAGTGCGTCAGGTACCT

TGACCCAGCACCAACTCAGACAAGCCACTCCCACCATCGTCACCCACTAT

CAGTCTCGAGAATTTTACAAGAATATCTTTGACGGTCTCAAGAAAAAGAG

TAACGACTACACGGTTCACTTTGGTACGAGAATCTACGTGGATCAGTTTG

TGACGCCTCGCCAGAGATATGCTGCCATTTTGGAGAAGCATTATCTGACT

GATCTCAAAGTTGAGGACTTCTCGAAGGCAAAAGAAACAACTCAGGCAAT

CAATAGTTGGGTGTCAAACATCACAAATGAGCACATAAAGGATCTCGTGA

AGGAGGAAGATGTTCAGAATTCAGTTATGCTCATGCTTAATGCAGTCTAC

TTCCGCGGACTCTGGCGCAAGCCTTTCAATCGTACACTCCCACTGCCCTT

CCACGTGAGCGCTGATGAGTCCAAGACGACTGATTTTATGCTAACCGATG

GGCTCTACTACTTCTACGAGGCAAAGGAATTGGATGCTAAGATCCTCAGA

ATTCCTTACAAAGGTAAACAATACGCAATGACTGTGATCTTACCAAATTC

CAAGAGTGGCATTGATAGCTTTGTGCGTCAGATTAACACGGTCCTCCTGC

ACAGGATTAAGTGGTTGATGGATGAAGTGGAGTGCAGGGTTATTCTACCC

AAGTTCCACTTTGACATGACGAATGAGCTGAAGGAATCGCTCGTAAAGTT

GGGCATCAGTCAGATTTTCACATCAGAGGCATCTTTGCCATCATTAGCAC

GAGGACAGGGCGTACAGAATCGTCTGCAGGTGTCTAATGTGATTCAGAAG

GCGGGAATAATTGTGGATGAGAAGGGCAGCACAGCCTATGCTGCGTCAGA

AGTGAGCCTAGTCAACAAGTTTGGAGATGATGAGTTCGTCATGTTCAACG

CTAATCATCCATTCCTCTTTACAATTGAGGACGAAACCACCGGCGCAATC

CTATTTACGGGAAAAGTCGTCGATCCCACGCAATAGGGAATGAAAAGCAT

-continued

TTCATCGTATACAACTTTTTTTTAATTAATTATTCCTCATTGAAGGACA

TTAATAGAGCATCTTCTCAGGAAGGCACTCCTGACTTATTTTTACTAAAT

GTGATCCTTGGACACATAAAAAAAACAGCTGTACTTTCTACTTTTTATAA

TATACGACCATATTTGTGAGGAAAAAAAAAAAAAAAAAAAAAAAAAAAAA

A

LJS03

(SEQ ID NO: 52)

TCAGTTAAGCAGATTTTCAAGCTAAAGAAACTTAACTAAGATGCGATTCC

TTCTTTTGGCCTTCTCCGTTGCTTTGGTGCTTTCACCAACATTCGCCAAA

CCAGGTCTTTGGGACATTGTAACTGGTATTAATGATATGGTAAAAAATAC

TGCGAATGCACTCAAAAATCGTCTAACAACTTCTGTGACATTATTCACAA

ATACCATCACCGAAGCTATAAAAAATGCAAATTCTTCTGTTTCGGAACTC

CTTCAGCAAGTCAATGAAACCCTTACGGATATTATTAATGGTGTAGGACA

AGTGCAGAGTGCCTTTGTGAATTCAGCTGGAAATGTTGTTGTGCAAATTG

TTGATGCCGCTGGAAATGTTTTGGAAGTTGTTGTTGATGAGGCTGGAAAT

ATCGTGGAGGTAGCTGGAACAGCATTGGAAACTATCATTCCACTGCCCGG

TGTAGTGATTCAGAAGATAATTGATGCTCTCCAAGGAAATGCAGGGACTA

CATCGGATTCAGCTTCATCAACTGTGCCCCAACAATCTTAACTACAACCG

CAATGATGTTGTCTTTAACGGAGAATTTTTAAATTTGAATATCAAAATCC

AAGATGAAATATTCAGATTTTTCAATCAATATGATACGAAATTTTGAAAT

TATTTTTCCGACTAAAGCAATTTGTAAAAGGAAAACCAAATAAATATTTG

AAATTGTAAAGAAAAAAAAAAAAAAAAAAAAAAAAAAAAA

LJS192

(SEQ ID NO: 54)

ATATCAATTTTATCATCATGGTGAAGTACTCGTGTCTTGTTCTTGTTGCA

ATTTTTCTTCTGGCCGGACCCTACGGCGTTGTAGGTTCTTGTGAGAATGA

CCTGACAGAGGCCGCCAAGTATCTTCAAGATGAATGCAATGCAGGTGAAA

TTGCAGATGAATTTCTACCCTTCTCTGAAGAAGAAGTGGGTGAAGCATTG

AGCGACAAACCAGAAAACGTGCAGGAAGTCACCAACATCGTGAGAGGATG

CTTTGAAGCTGAACAAGCCAAAGAGCATGGAAAATGTGAAAGATTTTCCG

CTTTGAGTCAATGCTACATTGAAAAGAATTTATGTCAATTCTTCTAAAAT

ATTTTGAAGAAAAGTTATGAATGAAAATTTTCTGAAATTTTGTTGCAAAA

ATATATAAATTGCCCAATTAAAAAAAAAAAAAAAAAAAAAAAAAAAAA

LJM19

(SEQ ID NO: 56)

AGTTTAATTTTCATCATGAAGTTCTTCTACTTGATTTTCTCTGCAATTTT

CTTTCTGGCTGATCCTGCTTTGGTCAAGTGTTCAGAGGATTGTGAGAATA

TTTTTCATGACAATGCGTACCTCCTTAAATTGGATTGTGAAGCAGGAAGG

GTTGATCCTGTTGAATACGACGATATTTCGGATGAAGAAATATATGAAAT

AACGGTCGATGTTGGAGTTTCATCTGAGGACCAGGAGAAAGTTGCGAAAA

TAATAAGGGAGTGCATTGCACAAGTTTCAACGCAAGATTGCACGAAATTT

TCAGAAATTTATGATTGTTACATGAAGAAGAAAATCTGTAATTATTATCC

TGAAAATATGTAAAAAAAAATTATTTATTTATATAAAAAAATATAAGGAT

TAAAATCTCTTATTGATTGTAAAAATGGCCTAATATTGAAGCAAAAATTA

AAGCATGAAACAAGACCAAAAAAAAAAAAAAAAAAAAAAAAAAAAAA

LJL138

(SEQ ID NO: 58)

TCAATCTAACAATGCACCTGCAATTGAATTTGTGCGCTATTCTCCTTTCG

GTACTAAATGGAATTCAGGGCGCTCCCAAAAGTATTAATTCAAAATCCTG

CGCAATCTCCTTTCCGGAGAATGTAACGGCTAAGAAGGAGCCAGTGTACT

TGAAACCATCAAATGATGGCTCATTGAGTACCCCCCTACAGCCAAGTGGG

CCATTTGTAAGTCTCAAAATTGGAGAATCTCTTGCAATCTTCTGTCCAGG

TGATGGAAAGGACGTAGAGACAATTACGTGCAATACAAATTTCGATTTAG

CTTCATATTCGTGCAACAAGAGCACATCAACGGATACCATTGAAACGGAA

GAAGTTTGCGGAGGAAGTGGAAAAGTGTACAAAGTTGGTTTTCCGCTGCC

CTCTGGGAATTTCCATTCAATCTACCAAACGTGTTTTGATAAGAAAAATC

TCACACCTCTCTACTCAATTCACATTCTCAATGGTCAAGCTGTTGGATAT

CACCTTAAGCACACAAGAGGAAGCTTTCGTACCAATGGTATCTACGGGAA

AGTCAACATTGATAAACTCTACAAGACGCAAATTGAGAAATTCAACAAAC

TTTTCGGCCCTAAACAAACATTTTTCCGTAGACCCCTCAATTTTCTATCA

CGTGGACACTTAAGCCCCGAAGTGGACTTTACATTCCGTAGGGAACAACA

TGCAACGGAAATGTACATTAACACAGCACCACAGTACCAATCAATTAATC

AAGGAAATTGGCTACGTGTTGAAAATCACGTGAGGGATCTCGCAAAAGTT

CTGCAGAAGGACATAACAGTCGTTACGGGAATTTTGGGGATACTTCGGTT

GAAGAGTAAGAAAATAGAGAAAGAAATCTATTTAGGAGATGACGTAATTG

CCGTACCAGCAATGTTCTGGAAGGCTGTTTTTGACCCTCAAAAACAAGAA

GCAATTGTCTTTGTTTCCTCAAATAATCCCCACGTGAAGACCTTTAATCC

CAACTGCAAGGATGTATGCGCTCAAGCTGGATTTGGGAATGATAATCTTG

AATATTTCTCCAATTATTCTATTGGTCTGACTATTTGTTGCAAACTTGAG

GAATTTGTTAAAAGAAATAAAATAATTCTACCCAAAGAAGTAAATAACAA

AAACTACACCAAAAAACTCCTTAAGTTTCCTAAAACAAGAAACAAGGAGG

GAGATAAGAAGGTGGTACGTAAGCGCGCCAAAGGAGCATAAATATTAAAC

GAAAAAAAAAAAAAAAAAAAAAAAAAAAAA

LJL15

(SEQ ID NO: 60)

GTTCTACGATAAAATTTTCTTTTCAAACTTTTCTTTTAAAGAAAAATCTT

CAAAAAGTTAAAATGAATTTGCACCTTGCGATTATCCTCTTTGTGAGTTA

CTTCACACTGATCACTGCTACGGATCTAATTGAAAAGGAACTTTCTGATT

GCAAAAAGATCTTCATCTCCAAGGCTGAGCTAACTTGGTTCCAAGCTCTC

GATTTCTGTACCGAACAAAACCTAACTTTGCTCTCAATTAAATCCGCCCG

GGAAAATGATGAGGTGACTAAAGCAGTTCGAGCTGAGGTTCATCTTCCAG

ACACAAAGAAGTCTCACATTTGGCTCGGAGGTATTCGTTATGATCAAGAC

AAGGATTTCCGTTGGATAAGCGATGGAACAACTGTTACGAAGACAGTCTA

CATCAATTGGTACCAAGGAGAACCAAATGGTGGGAGGTACCAAAAGGAAT

TTTGTATGGAATTGTACTTTAAAACTCCAGCTGGTCAATGGAATGATGAT

ATTTGTACAGCAAAGCATCATTTTATATGTCAGGAGAAAAAATAAATTGA

-continued

ATTGTTCATGTGTCTTTGGCGGTGCGAAGGTATAATTCAGGTTGACGACA

TAAATTGATTTTTCTTTCATTAAGAAAATAAAGGCTTGAATTTATAAAAA

AAAAAAAAAAAAAAAAAAAA

LJL91

(SEQ ID NO: 62)

GTTCTACGATAAAATTTTCTTTTCAAACTTTTCTTTTAAAGAAAAATCTT

CAAAAAGTTAAAATGAATTTGCCCCTTGCGATTATCCTCTTTGTGAGTTA

CTTCACACTGATCACTGCTGCGGATCTAACTGAAAAGGAACTTTCTGATG

GCAAAAAGATCTTCATCTCCAAGGCTGAGCTAAGTTGGTTCGATGCTCTC

GATGCCTGTACCGAAAAAGACCTAACTTTGCTCACAATTAAATCCGCCCG

GGAAAATGAGGAAGTGACTAAAGCAGTTCGAGCTGAGGTTCATCTTCCAG

ACACAAAGAAGTCTCACATTTGGCTCGGAGGTATTCGTTATGATCAAGAC

AAGGATTTCCGTTGGATAAGCGATGGAACAACTGTTACGAAGACAGTCTA

CATCAATTGGTACCAAGGAGAACCAAATGGTGGGAGGTACCAAAAGGAAT

TTTGTATGGAATTGTACTTTAAAACTCCAGCTGGTCAATGGAATGATGAT

ATTTGTACAGCAAAGCATCATTTTATATGTCAGGAGAAAAAATAAATTGA

ATTGTTCATGTGTCTTTGGCGGTGCGAAGGTATAATTCAGGTTGACGACA

TAAATTGATTTTTCTTTCATTAAGAAAATAAAGGCTTGAATTTAGCAAAA

AAAAAAAAAAAAAAAAAAAAA

LJM11

(SEQ ID NO: 64)

TTGAATTGAAGCAGCAGCAATGAAAGTGTTTTTCTCAATTTTTACGCTCG

TCCTCTTCCAAGGGACCCTTGGAGCGGATACTCAAGGATATAAATGGAAG

CAATTGCTCTACAATAATGTTACACCAGGATCCTACAATCCGGATAATAT

GATCAGTACGGCTTTTGCCTACGATGCTGAGGGTGAAAAACTCTTCCTAG

CTGTCCCAAGGAAGTTACCCAGAGTTCCGTATACATTGGCGGAAGTGGAT

ACAAAGAATAGTCTTGGTGTTAAGGGAAAACATTCACCGTTACTTAACAA

ATTCAGTGGGCACAAAACTGGGAAGGAACTAACATCAATCTATCAGCCAG

TTATTGATGATTGTCGTCGCCTTTGGGTGGTTGATATTGGTTCCGTGGAA

TATCGCTCAAGAGGTGCCAAAGACTACCCGAGTCATCGTCCTGCAATTGT

TGCGTACGACCTAAAGCAACCAAACTACCCCGAAGTTGTTCGATACTATT

TCCCCACAAGATTAGTGGAGAAGCCAACATATTTCGGTGGATTTGCCGTT

GATGTTGCAAACCCAAAGGGGGATTGTAGTGAAACTTTTGTCTACATTAC

AAACTTCCTCAGGGGAGCTCTCTTTATATACGATCATAAGAAGCAGGATT

CGTGGAATGTAACTCATCCCACCTTCAAAGCAGAACGACCCACTAAATTT

GATTACGGCGGAAAGGAATATGAATTCAAAGCCGGAATTTTCGGAATTAC

TCTCGGAGATCGAGACAGTGAAGGCAATCGTCCAGCTTACTACTTAGCCG

GAAGTGCCATCAAAGTCTACAGCGTCAACACGAAAGAACTTAAGCAGAAG

GGTGGAAAGCTGAATCCGGAGCTTCTTGGAAACCGCGGGAAGTACAACGA

TGCCATTGCCCTAGCTTACGATCCCAAAACTAAAGTTATCTTCTTTGCTG

AGGCCAACACAAAGCAAGTATCCTGCTGGAACACACAGAAAATGCCACTG

AGGATGAAGAATACCGACGTAGTCTACACTAGTTCTCGCTTTGTCTTTGG

-continued

AACGGACATTTCGGTTGATAGCAAGGGCGGCCTCTGGTTCATGTCTAACG

GCTTTCCGCCTATAAGGAAATCAGAAAAATTCAAATATGACTTCCCACGC

TACCGTCTAATGAGGATCATGGACACACAGGAAGCAATTGCCGGAACTGC

TTGCGATATGAATGCATAAAAGTTAATTTTCAACCCAAGAAGAAGACCTA

AAGAGGCTTTTCCAGGCTTTGATGCAGGAGAGGTGGTTATCAACGCAAAA

TCAGCTATTGTTGTATGAGGAGGAGAAATTATTGATTCTGAATTCTATAA

AAAAAATTTAATTTGTGAAATATTTGGCAATAATAAATTAATTGAATTAC

AAAAAAAAAAAAAAAAAAAAAAAAAAAA

LJS138

(SEQ ID NO: 66)

TCTCTTTGGTTAACATTGTGAAGTTATCGGACGTGGCCGGTTTCTATTTC

TTTTGCAAAAATGCAGTCAAAAATTCTTTCTTTCGTCCTTTTCACCTTAT

CCTTGGGCTATGTTTTGGGTGAAACATGCTCAAATGCTAAGGTTAAGGGA

GCTACCTCTTATTCCACAACGGATGCCACAATTGTAAGCCAAATTGCCTT

TGTGACTGAATTCTCCTTGGAATGCTCAAATCCTGGATCCGAGAAAATCT

CCCTATTTGCTGAAGTCGATGGCAAAATTACTCCTGTTGCCATGATCGGG

GATACCACCTACCAGGTGAGCTGGAATGAAGAGGTTAATAAGGCTAGAAG

TGGTGACTACAGTGTGAAGCTGTACGATGAAGAAGGATACGGAGCAGTAC

GCAAAGCTCAGAGATCAGGTGAAGAGAACAAGGTCAAACCACTAGCAACC

GTTGTTGTTCGACATCCAGGAACATACACTGGACCATGGTTCAATTCCGA

AATCCTCGCAGCTGGTCTCATTGCTGTTGTTGCCTACTTTGCTTTCTCAA

CGCGAAGCAAAATTCTTTCCTAAAGAGACGCAGCATGAAATTTCACAAAA

AAATAAAAACAAATTCAAGTCATCAACCATGTCTCTTTGGCACTCAGACT

GTTTCTGTGAAATACAAACTATTATTTAACAAAAAAAAAAAAAAAAAAAA

AAAAAAAAAAAA

LJL124

(SEQ ID NO: 68)

ATTCCCACAAGAAGCTGCTAAAATGGTGTCAATTCTGTTAATCTCCTTGA

TTCTTAATTTGTTGGTTTTCTATGCTAAAGCTAGACCACTAGAAGACATC

TCGTCAGATCTTTCCCCTGATTATTACATCACTGAAGGCTATGACGGTGT

GAAGGAGAAGAGAGAGATCGAACTTGTACCTGTGACATTTGGAATATTTA

ATATACATACAACACCTGCTCCCAGAATTACCTTTGAATGGTAAAAAATC

CAAGAAGAATTTATGATTTTATTCTTCCTTCCATTGGGATGGATTGTAAG

TCAGCATAAAACGCCGTTAAAAATGAATTTTTAATAAAAAAAAATTATTC

CAAAAAAAAAAAAAAAAAAAAAAAAAAA

LJL35

(SEQ ID NO: 70)

CACTATTCATTGGAAGATTTATTAACTTCAAGATGAAATTATTTTGTTTA

ATTTTTGTTGTGTTTGTTGCTTTAGAAGTCTGTATAGAGACCGTGAAAGC

TATGGAAGCAACGGAGGAGATATCTGTAAAATTGCAAGATGATGCGAATG

AACCTGATGACTCTCTGGATTTAGACGAAGGTCTTCCTGATGCATTCGAT

GAGGACTATAATAATCAGGCTGAGTACAAGCCGAATCCTAGAGGGGACTA

CAGAAGACGATAATTAATATAAATTCAGGAAAACACTCTAAAAATTTCCA

ATTGACTCTACTTTAAACGATTTAATACCTACCTACACTAAATACCATAT

-continued

```
GCAATAATTATGTTTTAATTATTTAGTGCAAGATCTACTAGTTTCAGTTC

ATATTTTGGGACTTTCCCGCCTTTCTCTCGATGGAAAAATGATTTTACGG

ATTCTTAATTTTCATTGTACAGAGTTAATAAAACAATTGAAAGCAATTAA

AAAAAAAAAAAAAAAAAAAAAAAAA
```

Also included are fragments of the above-described nucleic acid sequences that are at least 33 bases, at least 36 bases, at least 42 bases or at least 48 bases in length, which is sufficient to permit the fragment to selectively hybridize to a polynucleotide that encodes a disclosed *Lu. longipalpis* under specified conditions. The term "selectively hybridize" refers to hybridization under moderately or highly stringent conditions, which excludes non-related nucleotide sequences.

Also disclosed herein are open reading frames (ORFs) encoding a *Lu. longipalpis* polypeptide. These ORFs are delimited by a start codon and by a stop codon. This also includes the degenerate variants and nucleotide sequences encoding conservative variants and homologs.

Specific, non-limiting examples of open reading frames are as follows:

The LJL34 unprocessed protein is encoded by nucleic acids 30-842 of SEQ ID NO: 2, and the mature protein is encoded by the nucleic acid sequence 87-842 of SEQ ID NO: 2.

The LJL18 unprocessed protein is encoded by nucleic acids 56-532 of SEQ ID NO: 4, and the mature protein is encoded by the nucleic acid sequence 113-532 of SEQ ID NO: 4.

The LJS193 unprocessed protein is encoded by nucleic acids 216-502 of SEQ ID NO: 6, and the mature protein is encoded by the nucleic acid sequence 276-502 of SEQ ID NO: 6.

The LJS201 unprocessed protein is encoded by nucleic acids 48-353 of SEQ ID NO: 8, and the mature protein is encoded by the nucleic acid sequence 117-352 of SEQ ID NO: 8.

The LJL13 unprocessed protein is encoded by nucleic acids 26-766 of SEQ ID NO: 10, and the mature protein is encoded by the nucleic acid sequence 83-766 of SEQ ID NO: 10.

The LJL23 unprocessed protein is encoded by nucleic acids 18-992 of SEQ ID NO: 12, and the mature protein is encoded by the nucleic acid sequence 81-992 of SEQ ID NO: 12.

The LJM10 unprocessed protein is encoded by nucleic acids 92-571 of SEQ ID NO: 14, and the mature protein is encoded by the nucleic acid sequence 149-571 of SEQ ID NO: 14.

The LJL143 unprocessed protein is encoded by nucleic acids 46-948 of SEQ ID NO: 16, and the mature protein is encoded by the nucleic acid sequence 115-948 of SEQ ID NO: 16.

The LJS142 unprocessed protein is encoded by nucleic acids 25-507 of SEQ ID NO: 18, and the mature protein is encoded by the nucleic acid sequence 85-507 of SEQ ID NO: 18.

The LJL17 unprocessed protein is encoded by nucleic acids 28-342 of SEQ ID NO: 20, and the mature protein is encoded by the nucleic acid sequence 88-342 of SEQ ID NO: 20.

The LJM06 unprocessed protein is encoded by nucleic acids 50-523 of SEQ ID NO: 22, and the mature protein is encoded by the nucleic acid sequence 107-523 of SEQ ID NO: 22.

The LJM17 unprocessed protein is encoded by nucleic acids 24-1264 of SEQ ID NO: 24, and the mature protein is encoded by the nucleic acid sequence 83-1264 of SEQ ID NO: 24.

The LJL04 unprocessed protein is encoded by nucleic acids 30-914 of SEQ ID NO: 26, and the mature protein is encoded by the nucleic acid sequence 81-914 of SEQ ID NO: 26.

The LJM114 unprocessed protein is encoded by nucleic acids 29-475 of SEQ ID NO: 28, and the mature protein is encoded by the nucleic acid sequence 101-475 of SEQ ID NO: 28.

The LJM111 unprocessed protein is encoded by nucleic acids 24-1214 of SEQ ID NO: 30, and the mature protein is encoded by the nucleic acid sequence 78-1214 of SEQ ID NO: 30.

The LJM78 mature unprocessed protein is encoded by nucleic acids 42-1091 of SEQ ID NO: 32, and the mature protein is encoded by the nucleic acid sequence 102-11091 of SEQ ID NO: 32.

The LJS238 unprocessed protein is encoded by nucleic acids 27-206 of SEQ ID NO: 34, and the mature protein is encoded by the nucleic acid sequence 87-206 of SEQ ID NO: 34.

The LJS169 unprocessed protein is encoded by nucleic acids 11-370 of SEQ ID NO: 36, and the mature protein is encoded by the nucleic acid sequence 77-370 of SEQ ID NO: 36.

The LJL11 unprocessed protein is encoded by nucleic acids 30-1745 of SEQ ID NO: 38, and the mature protein is encoded by the nucleic acid sequence 105-1745 of SEQ ID NO: 38.

The LJL08 unprocessed protein is encoded by nucleic acids 26-238 of SEQ ID NO: 40, and the mature protein is encoded by the nucleic acid sequence 95-238 of SEQ ID NO: 40.

The LJS105 unprocessed protein is encoded by nucleic acids 24-275 of SEQ ID NO: 42, and the mature protein is encoded by the nucleic acid sequence 81-275 of SEQ ID NO: 42.

The LJL09 unprocessed protein is encoded by nucleic acids 74-1954 of SEQ ID NO: 44, and the mature protein is encoded by the nucleic acid sequence 128-1954 of SEQ ID NO: 44.

The LJL38 unprocessed protein is encoded by nucleic acids 40-165 of SEQ ID NO: 46, and the mature protein is encoded by the nucleic acid sequence 100-165 of SEQ ID NO: 46.

The LJM04 unprocessed protein is encoded by nucleic acids 40-456 of SEQ ID NO: 48, and the mature protein is encoded by the nucleic acid sequence 100-456 of SEQ ID NO: 48.

The LJM26 unprocessed protein is encoded by nucleic acids 96-1616 of SEQ ID NO: 50, and the mature protein is encoded by the nucleic acid sequence 147-1616 of SEQ ID NO: 50.

The LJS03 unprocessed protein is encoded by nucleic acids 41-553 of SEQ ID NO: 52, and the mature protein is encoded by the nucleic acid sequence 98-553 of SEQ ID NO: 52.

The LJS192 unprocessed protein is encoded by nucleic acids 18-344 of SEQ ID NO: 54, and the mature protein is encoded by the nucleic acid sequence 87-344 of SEQ ID NO: 54.

The LJM19 unprocessed protein is encoded by nucleic acids 16-360 of SEQ ID NO: 56, and the mature protein is encoded by the nucleic acid sequence 82-360 of SEQ ID NO: 56.

The LJL138 unprocessed protein is encoded by nucleic acids 12-1238 of SEQ ID NO: 58 and the mature protein is encoded by the nucleic acid sequence 72-1238 of SEQ ID NO: 58.

The LJL15 unprocessed protein is encoded by nucleic acids 63-542 of SEQ ID NO: 60, and the mature protein is encoded by the nucleic acid sequence 120-542 of SEQ ID NO: 60.

The LJL91 unprocessed protein is encoded by nucleic acids 63-542 of SEQ ID NO: 62, and the mature protein is encoded by the nucleic acid sequence 120-542 of SEQ ID NO: 62.

The LJM11 unprocessed protein is encoded by nucleic acids 20-1216 of SEQ ID NO: 64, and the mature protein is encoded by the nucleic acid sequence 74-1216 of SEQ ID NO: 64.

The LJS138 unprocessed protein is encoded by nucleic acids 12-1238 of SEQ ID NO: 66, and the mature protein is encoded by the nucleic acid sequence 72-138 of SEQ ID NO: 66.

The LJL124 unprocessed protein is encoded by nucleic acids 23-241 of SEQ ID NO: 68, and the mature protein is encoded by the nucleic acid sequence 83-241 of SEQ ID NO: 68.

The LJL35 unprocessed protein is encoded by nucleic acids 12-1238 of SEQ ID NO: 70, and the mature protein is encoded by the nucleic acid sequence 72-1238 of SEQ ID NO: 70.

Another specific non-limiting example of a polynucleotide encoding a *Lu. longipalpis* polypeptide is a polynucleotide having at least 75%, 85%, 90%, 95%, or 99% homology to one of the sequences set forth above that encodes a polypeptide having an antigenic epitope or function of a *Lu. longipalpis* polypeptide. Yet another specific non-limiting example of a polynucleotide encoding a *Lu. longipalpis* polypeptide is a polynucleotide that encodes a polypeptide that is specifically bound by an antibody that specifically binds the *Lu. longipalpis* polypeptide.

The *Lu. longipalpis* polynucleotides include a recombinant DNA which is incorporated into a vector, into an autonomously replicating plasmid or virus, or into the genomic DNA of a prokaryote or eukaryote, or which exists as a separate molecule (for example, a cDNA) independent of other sequences. The nucleotides can be ribonucleotides, deoxyribonucleotides, or modified forms of either nucleotide. The term includes single and double forms of either nucleotide. The term includes single and double forms of DNA.

Recombinant vectors are also disclosed herein that include a polynucleotide encoding a polypeptide or a fragment thereof according to the disclosure. Recombinant vectors include plasmids and viral vectors and may be used for in vitro or in vivo expression.

A plasmid may include a DNA transcription unit, for instance a nucleic acid sequence that permit it to replicate in a host cell, such as an origin of replication (prokaryotic or eukaryotic). A plasmid may also include one or more selectable marker genes and other genetic elements known in the art. Circular and linear forms of plasmids are encompassed in the present disclosure.

For in vivo expression, the promoter is generally of viral or cellular origin. In one embodiment, the cytomegalovirus (CMV) early promoter (CMV-IE promoter), including the promoter and enhancer, is of use. The CMV-IE promoter can be of human or murine origin, or of other origin such as rat or guinea pig (see EP 0260148; EP 0323597; WO 89/01036; Pasleau et al., *Gene* 38:227-232, 1985; Boshart M. et al., *Cell* 41:521-530, 1985). Functional fragments of the CMV-IE promoter may also be used (WO 98/00166). The SV40 virus early or late promoter and the Rous Sarcoma virus LTR promoter are also of use. Other promoters include but are not limited to, a promoter of a cytoskeleton gene, such as (but not limited to) the desmin promoter (Kwissa M. et al., *Vaccine* 18(22):2337-2344, 2000), or the actin promoter (Miyazaki J. et al., *Gene* 79(2):269-277, 1989). When several genes are present in the same plasmid, they may be provided in the same transcription unit or in different units.

The plasmids may also comprise other transcription regulating elements such as, for example, stabilizing sequences of the intron type. In several embodiments the plasmids include the first intron of CMV-IE (Published PCT Application No. WO 89/01036), the intron II of the rabbit β-globin gene (van Ooyen et al., *Science* 206:337-344, 1979), the signal sequence of the protein encoded by the tissue plasminogen activator (tPA; Montgomery et al., *Cell. Mol. Biol.* 43:285-292, 1997), and/or a polyadenylation signal (polyA), in particular the polyA of the bovine growth hormone (bGH) gene (U.S. Pat. No. 5,122,458) or the polyA of the rabbit β-globin gene or of SV40 virus.

In a specific, non-limiting example, the pVR1020 plasmid (VICAL Inc.; Luke C. et al., *Journal of Infectious Diseases* 175:91-97, 1997; Hartikka J. et al., *Human Gene Therapy* 7:1205-1217, 1996)) can be utilized as a vector for the insertion of such a polynucleotide sequence, generating recombinant plasmids.

The plasmids are evaluated in dogs in order to determine their efficacy against a *Leishmania* infection (Vidor E. et al., P3.14, XXIV World Veterinary Congress, Rio de Janeiro, Brazil, 18-23 Aug. 1991).

Various viral vectors are also of use with a polynucleotide encoding a *Lu. longipalpis* polypeptide. A specific, non-limiting example includes recombinant poxvirus, including avipox viruses, such as the canarypox virus. Another specific, non-limiting example includes recombinant poxvirus, including vaccinia viruses (U.S. Pat. No. 4,603,112), such as attenuated vaccinia virus such as NYVAC (see U.S. Pat. No. 5,494,807) or Modified Vaccinia virus Ankara (MVA, Stickl H. and Hochstein-Mintzel V., *Munch. Med. Wschr.* 113: 1149-1153, 1971; Sutter G. et al., *Proc. Natl. Acad. Sci. USA* 89:10847-10851, 1992; Carroll M. W. et al., *Vaccine* 15(4): 387-394, 1997; Stittelaar K. J. et al., *J. Virol.* 74(9):4236-4243, 2000; Sutter G. et al., *Vaccine* 12(11):1032-1040, 1994). When avipox viruses are used, canarypox viruses (U.S. Pat. No. 5,756,103) and fowlpox viruses (U.S. Pat. No. 5,766,599) are of use, such as attenuated viruses. For recombinant canarypox virus vectors, the insertion sites may be in particular in the ORFs C3, C5 or C6. When the expression vector is a poxvirus, the heterologous polynucleotide can be inserted under the control of a poxvirus specific promoter, such as the vaccinia virus 7.5 kDa promoter (Cochran et al., *J. Virology* 54:30-35, 1985), the vaccinia virus I3L promoter (Riviere et al., *J. Virology* 66:3424-3434, 1992), the vaccinia virus HA promoter (Shida, *Virology* 150:451-457, 1986), the cowpox virus ATI promoter (Funahashi et al., *J. Gen. Virol.* 69:35-47, 1988), other vaccinia virus H6 promoter (Taylor et al., *Vaccine* 6:504-508, 1988; Guo et al., *J. Virol.* 63:4189-4198, 1989; Perkus et al., *J. Virol.* 63:3829-3836, 1989).

Other viral vectors of use are herpes virus or adenovirus vectors. Specific, non-limiting examples include a canine herpes virus (CHV) or canine adenovirus (CAV) vector (for example, see U.S. Pat. No. 5,529,780; U.S. Pat. No. 5,688,920; Published PCT Application No. WO 95/14102). For CHV, the insertion sites may be in particular in the thymidine kinase gene, in the ORF3, or in the UL43 ORF (see U.S. Pat. No. 6,159,477). For CAV, the insertion sites may be in particular in the E3 region or in the region located between the E4 region and the right ITR region (see U.S. Pat. No. 6,090,393; U.S. Pat. No. 6,156,567). In one embodiment in CHV or CAV vectors the insert is in general under the control of a promoter (as described above for the plasmids), such as CMV-IE promoter.

Multiple insertions can be done in the same vector using different insertion sites or using the same insertion site. When the same insertion site is used, each polynucleotide insert is inserted under the control of different promoters. The insertion can be done tail-to-tail, head-to-head, tail-to-head, or head-to-tail. IRES elements (Internal Ribosome Entry Site, see European Patent EP 0803573) can also be used to separate and to express multiple inserts operably linked to the same promoter. Bacterial vectors can also be used for in vivo expression.

Any polynucleotide according to the disclosure can be expressed in vitro by DNA transfer or expression vectors into a suitable host cell. The host cell may be prokaryotic or eukaryotic. The term "host cell" also includes any progeny of the subject host cell. Methods of stable transfer, meaning that the foreign polynucleotide is continuously maintained in the host cell, are known in the art. Host cells can include bacteria (for example, *Escherichia coli*), yeast, insect cells, and vertebrate cells. Methods of expressing DNA sequences in eukaryotic cells are well known in the art.

As a method for in vitro expression, recombinant Baculovirus vectors (for example, Autographa California Nuclear Polyhedrosis Virus (AcNPV)) can be used with the nucleic acids disclosed herein. For example, polyhedrin promoters can be utilized with insect cells (for example, *Spodoptera frugiperda* cells, like Sf9 cells available at the ATCC under the Accession number CRL-1711, or Sf21 cells) (see for example, Smith et al., *Mol. Cell Biol.* 3:2156-2165, 1983; Pennock et al., *Mol. Cell Biol.* 4: 399-406, 1994; Vialard et al., *J. Virol.* 64:37-50, 1990; Verne A., *Virology* 167:56-71, 1988; O'Reilly et al., "Baculovirus expression vectors, A laboratory manual," New York Oxford, Oxford University Press, 1994; Kidd I. M. & Emery V. C., "The use of baculoviruses as expression vectors," *Applied Biochemistry and Biotechnology* 42:37-159, 1993; European Patent No. EP 0370573; European Patent No. EP 0265785; U.S. Pat. No. 4,745,051). For expression the BACULOGOLD™ Starter Package (Cat #21001K) from Pharmingen (Becton Dickinson) can be used.

As a method for in vitro expression, recombinant *E. coli* can be used with a vector. For example, when cloning in bacterial systems, inducible promoters such as arabinose promoter, pL of bacteriophage lambda, plac, ptrp, ptac (ptrp-lac hybrid promoter), and the like may be used.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transduction of DNA as calcium phosphate coprecipitates, conventional mechanical procedures such as microinjection, electroporation, insertion of a plasmid encased in liposomes, or virus vectors may be used. Eukaryotic cells can also be cotransformed with *Lu. longipalpis* polynucleotide sequences, and a second foreign DNA molecule encoding a selectable phenotype, such as the herpes simplex thymidine kinase gene. Another method is to use a eukaryotic viral vector (see above), such as a herpes virus or adenovirus (for example, canine adenovirus 2), to transiently transduce eukaryotic cells and express the protein (see for example, *Eukaryotic Viral Vectors*, Cold Spring Harbor Laboratory, Gluzman ed., 1982). In addition, a transfection agent can be utilized, such as dioleoyl-phosphatidyl-ethanolamine (DOPE).

Isolation and purification of recombinantly expressed polypeptide may be carried out by conventional means including preparative chromatography (for example, size exclusion, ion exchange, affinity), selective precipitation and ultra-filtration. Such a recombinantly expressed polypeptide is part of the present disclosure. The methods for production of such a polypeptide are also encompassed, in particular the use of a recombinant expression vector comprising a polynucleotide according to the disclosure and of a host cell.

Antibodies

A *Lu. longipalpis* polypeptide of the disclosure or a fragment thereof according to the disclosure can be used to produce antibodies. Polyclonal antibodies, antibodies which consist essentially of pooled monoclonal antibodies with different epitopic specificities, as well as distinct monoclonal antibodies are included. Such antibodies are of use as markers for exposure, and as immunodiagnostic tools to follow the development of the immune response to *Lu. longipalpis* salivary proteins.

The preparation of polyclonal antibodies is well-known to those skilled in the art. See, for example, Green et al., "Production of Polyclonal Antisera," *Immunochemical Protocols*, pp. 1-5, Manson, ed., *Humana Press,* 1992; Coligan et al., "Production of Polyclonal Antisera in Rabbits, Rats, Mice and Hamsters," *Current Protocols in Immunology*, section 2.4.1, 1992.

The preparation of monoclonal antibodies likewise is conventional. See, for example, Kohler & Milstein, *Nature* 256:495, 1975; Coligan et al., sections 2.5.1-2.6.7; and Harlow et al., *Antibodies: A Laboratory Manual*, p. 726, Cold Spring Harbor Pub., 1988. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, for example, Coligan et al., sections 2.7.1-2.7.12 and sections 2.9.1-2.9.3; Barnes et al., "Purification of Immunoglobulin G (IgG)," *Methods in Molecular Biology*, Vol. 10, pp. 79-104, Humana Press, 1992.

Methods of in vitro and in vivo multiplication of monoclonal antibodies are well known to those skilled in the art.

Multiplication in vitro may be carried out in suitable culture media such as Dulbecco's Modified Eagle Medium or RPMI 1640 medium, optionally supplemented by a mammalian serum such as fetal calf serum or trace elements and growth-sustaining supplements such as normal mouse peritoneal exudate cells, spleen cells, thymocytes, or bone marrow macrophages. Production in vitro provides relatively pure antibody preparations and allows scale-up to yield large amounts of the desired antibodies. Large-scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, for example, syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Antibodies can also be derived from subhuman primate antibody. General techniques for raising therapeutically useful antibodies in baboons can be found, for example, in WO 91/11465, 1991, and Losman et al., *Int. J. Cancer* 46:310, 1990.

Alternatively, an antibody that specifically binds a polypeptide can be derived from a humanized monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833, 1989. Techniques for producing humanized monoclonal antibodies are described, for example, by Jones et al., *Nature* 321:522, 1986; Riechmann et al., *Nature* 332:323, 1988; Verhoeyen et al., *Science* 239:1534, 1988; Carter et al., *Proc. Nat'l Acad. Sci. USA* 89:4285, 1992; Sandhu, *Crit. Rev. Biotech.* 12:437, 1992; and Singer et al., *J. Immunol.* 150:2844, 1993.

Antibodies can be derived from human antibody fragments isolated from a combinatorial immunoglobulin library. See, for example, Barbas et al., *Methods: a Companion to Methods in Enzymology*, Vol. 2, p. 119, 1991; Winter et al., *Ann. Rev. Immunol.* 12:433, 1994. Cloning and expression vectors that are useful for producing a human immunoglobulin phage library can be obtained, for example, from STRATAGENE Cloning Systems (La Jolla, Calif.).

In addition, antibodies can be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13, 1994; Lonberg et al., *Nature* 368:856, 1994; and Taylor et al., *Int. Immunol.* 6:579, 1994.

Antibodies include intact molecules as well as fragments thereof, such as Fab, $F(ab')_2$, and Fv which are capable of binding the epitopic determinant. These antibody fragments retain some ability to selectively bind with their antigen or receptor and are defined as follows:

(1) Fab, the fragment which contains a monovalent antigen-binding fragment of an antibody molecule, can be produced by digestion of whole antibody with the enzyme papain to yield an intact light chain (L) and a portion of one heavy chain(H);

(2) Fab', the fragment of an antibody molecule that can be obtained by treating a whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating a whole antibody with the enzyme pepsin without subsequent reduction; $F(ab')_2$ is a dimer of two Fab' fragments held together by two disulfide bonds;

(4) Fv, defined as a genetically engineered fragment containing the variable region of the light chain ($V_L$) and the variable region of the heavy chain ($V_H$) expressed as two chains; and (5) Single chain antibody (SCA), defined as a genetically engineered molecule containing the variable region of the light chain, the variable region of the heavy chain, linked by a suitable polypeptide linker as a genetically fused single chain molecule.

Methods of making these fragments are known in the art. (See for example, Harlow and Lane, *Antibodies: A Laboratory Manual*, Cold Spring Harbor Laboratory, New York, 1988).

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent (Inbar et al., *Proc. Nat'l Acad. Sci. USA* 69:2659, 1972). Alternatively, the variable chains can be linked by an intermolecular disulfide bond or cross-linked by chemicals such as glutaraldehyde. See, for example, Sandhu, supra. In one embodiment, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; and Sandhu, supra).

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (Larrick et al., *Methods: a Companion to Methods in Enzymology*, Vol. 2, page 106, 1991).

Antibodies can be prepared using an intact polypeptide or fragments containing small peptides of interest as the immunizing antigen. The polypeptide or a peptide used to immunize an animal can be derived from substantially purified polypeptide produced in host cells, in vitro translated cDNA, or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize an animal (for example, a mouse, a rat, or a rabbit).

Polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan et al., Unit 9, *Current Protocols in Immunology*, Wiley Interscience, 1991).

It is also possible to use the anti-idiotype technology to produce monoclonal antibodies which mimic an epitope. For example, an anti-idiotypic monoclonal antibody made to a first monoclonal antibody will have a binding domain in the hypervariable region that is the "image" of the epitope bound by the first mono-clonal antibody.

In view of the large number of methods that have been reported for attaching a variety of radiodiagnostic compounds, radiotherapeutic compounds, label (for example, enzymes or fluorescent molecules) drugs, toxins, and other agents to antibodies one skilled in the art will be able to determine a suitable method for attaching a given agent to an antibody or other polypeptide.

In one embodiment, an antibody that binds a *Lu. Longipalpis* polypeptide can be used to assess whether a subject has been bitten by a sand fly. In one specific, non-limiting example, a sample is obtained from a subject of interest, such as a human or a dog. The sample can be a body fluid (for example, blood, serum, urine, saliva, etc.) or a tissue biopsy. The sample or a fraction thereof is contacted with the antibody, and the ability of the antibody to form an antigen-antibody complex is assessed. One of skill in the art can readily detect the formation of an antigen-antibody complex. For example, ELISA, Western blot, or radio-immune assays can be utilized.

Immunogenic Compositions, Vaccines and Methods of Use

Immunogenic compositions and vaccines are disclosed herein. In one embodiment the immunogenic compositions and vaccines include a polypeptide. In another embodiment, the immunogenic compositions and vaccines include a recombinant vector, such as a viral vector or a plasmid. When administered to a subject such an immunogenic composition or vaccine generates an immune response to the sand fly's salivary protein(s), and surprisingly a reduction of the leishmaniasis symptoms and a decrease of the *Leishmania* parasite load results. Thus, without being bound by theory, a cellular response, such as a Th1 response, produced against the salivary protein can indirectly kill a *Leishmania* parasite. For example, a Th1 type response can allow macrophages to take up *Leishmania* antigens and present them to T cells in a Th1 context. The induction the Th1 response can produce an anti-*Leishmania* immune response, or can prime the immune system of the mammalian host for anti-*Leishmania* immunity in response to a later infection.

In one embodiment, the immunogenic composition or the vaccine includes an effective amount of at least one *Lu. longipalpis* polypeptide disclosed herein. The immunogenic composition and the vaccine can include a pharmaceutically acceptable excipient and/or an adjuvant. In one embodiment, the immunogenic composition or vaccine includes a polypeptide having an amino acid sequence as set forth as SEQ ID NO: 3, SEQ ID NO: 5, SEQ ID NO: 7, SEQ ID NO: 9, SEQ ID NO: 13, SEQ ID NO: 15, SEQ ID NO: 17, SEQ ID NO: 19, SEQ ID NO: 21, SEQ ID NO: 25, SEQ ID NO: 27, SEQ ID NO: 29, SEQ ID NO: 31, SEQ ID NO: 33, SEQ ID NO: 35, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 59, SEQ ID NO: 61, SEQ ID NO: 63, SEQ ID NO: 65, or SEQ ID NO: 67, a polypeptide at least 80%, at least 90%, at least 95%, or at least 99% homologous to one of these polypeptides, a conservative variant, a homolog or an immunogenic fragment comprising at least eight or at least ten consecutive amino acids of one of these polypeptides, or a combination of these polypeptides. In one specific, non-limiting example, the immunogenic composition or vaccine includes a polypeptide having an amino acid sequence as set forth as SEQ ID NO: 3, SEQ ID NO: 5, SEQ ID NO: 7, SEQ ID NO: 9, SEQ ID NO: 13, SEQ ID NO: 15, SEQ ID NO: 17, SEQ ID NO: 19, SEQ ID NO: 21, SEQ ID NO: 25, SEQ ID NO: 27, SEQ ID NO: 29, SEQ ID NO: 31, SEQ ID NO: 33, SEQ ID NO: 35, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 59, SEQ ID NO: 61, SEQ ID NO: 63, SEQ ID NO: 65, or SEQ ID NO: 67. In specific, non-limiting examples, the immunogenic composition includes a polypeptide having a sequence set forth as one of SEQ ID NO: 3, SEQ ID NO: 11, SEQ ID NO: 19, SEQ ID NO: 29, SEQ ID NO: 55, or SEQ ID NO: 59.

In one embodiment, the immunogenic composition includes more than one *Lu. longipalpis* polypeptide, such as two, three, four, five, six, ten or more of the polypeptides disclosed herein. Thus, the immunogenic composition includes at least one polypeptide having an amino acid sequence as set forth as SEQ ID NO: 3, SEQ ID NO: 5, SEQ ID NO: 7, SEQ ID NO: 9, SEQ ID NO: 13, SEQ ID NO: 15, SEQ ID NO: 17, SEQ ID NO: 19, SEQ ID NO: 21, SEQ ID NO: 25, SEQ ID NO: 27, SEQ ID NO: 29, SEQ ID NO: 31, SEQ ID NO: 33, SEQ ID NO: 35, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 59, SEQ ID NO: 61, SEQ ID NO: 63, SEQ ID NO: 65, or SEQ ID NO: 67, a polypeptide at least 80%, at least 90%, at least 95%, or at least 99% homologous to one of these polypeptides, a conservative variant, a homolog or an immunogenic fragment comprising at least eight or at least ten consecutive amino acids of one of these polypeptides, and optionally another polypeptide having an amino acid sequence as set forth as SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 59, SEQ ID NO: 61, SEQ ID NO: 63, SEQ ID NO: 65, or SEQ ID NO: 67, or SEQ ID NO: 69, a polypeptide at least 80%, at least 90%, at least 95%, or at least 99% homologous to one of these polypeptides, a conservative variant of one of these polypeptides, or a homolog or an immunogenic fragment comprising at least eight or at least ten consecutive amino acids of one of these polypeptides.

In specific non-limiting examples, the immunogenic composition includes an amino acid having a sequence as set forth as SEQ ID NO: 1, SEQ ID NO: 23, SEQ ID NO: 39, a polypeptide at least 80%, at least 90%, at least 95%, or at least 99% homologous to one of these polypeptides, a conservative variant of one of these polypeptides, or a homolog or an immunogenic fragment comprising at least eight or at least ten consecutive amino acids of one of these polypeptides, or a combination of these polypeptides. Thus, the immunogenic composition can include a polypeptide having a sequence as set forth as SEQ ID NO: 1, SEQ ID NO: 23, or SEQ ID NO: 39. These compositions include, but are not limited to, an immunogenic composition including a polypeptide having a sequence as set forth as SEQ ID NO: 3, SEQ ID NO: 11, SEQ ID NO: 19, SEQ ID NO: 29, SEQ ID NO: 55, or SEQ ID NO: 59, and a polypeptide having a sequence as set forth as SEQ ID NO: 1, SEQ ID NO: 23, or SEQ ID NO: 39.

The immunogenic composition or the vaccine can include a pharmaceutically acceptable excipient and/or an adjuvant.

In another embodiment, the immunogenic composition or the vaccine includes an effective amount of at least one *Lu. longipalpis* polypeptide in conjunction with one or more *P. perniciosus* polypeptide(s) and/or one or more *P. ariasi* polypeptide(s). These polypeptide sequences are disclosed in U.S. Patent Application No. 60/412,327, filed Sep. 19, 2002, U.S. Patent Application No. 60/425,852, filed Nov. 12, 2002, and PCT Application No. PCT/US03/29833, filed Sep. 18, 2003, which are incorporated herein by reference.

In one embodiment, the immunogenic composition or the vaccine comprises an effective amount of a recombinant vector expressing at least one *Lu. longipalpis* polypeptide disclosed herein and a pharmaceutically acceptable vehicle or excipient. In one specific, non-limiting example the recombinant vector encodes at least one polypeptide having an amino acid sequence as set forth as SEQ ID NO: 3, SEQ ID NO: 5, SEQ ID NO: 7, SEQ ID NO: 9, SEQ ID NO: 13, SEQ ID NO: 15, SEQ ID NO: 17, SEQ ID NO: 19, SEQ ID NO: 21, SEQ ID NO: 25, SEQ ID NO: 27, SEQ ID NO: 29, SEQ ID NO: 31, SEQ ID NO: 33, SEQ ID NO: 35, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 59, SEQ ID NO: 61, SEQ ID NO: 63, SEQ ID NO: 65, or SEQ ID NO: 67, a conservative variant, a homolog, an immunogenic fragment, or a fusion protein thereof. In specific non-limiting examples the vector encodes a polypeptide having a sequence as set forth as SEQ ID NO: 3, SEQ ID NO: 11, SEQ ID NO: 19, SEQ ID NO: 29, SEQ ID NO: 55, or SEQ ID NO: 59, a polypeptide at least 80%, at least 90%, at least 95%, or at least 99% homologous to one of these polypeptides, a conservative variant, a homolog, an immunogenic fragment, or a fusion protein thereof. In several examples the vector encodes one or more polypeptides having a sequence as set forth as SEQ ID NO: 3, SEQ ID NO: 11, SEQ ID NO: 19, SEQ ID NO: 29, SEQ ID NO: 55, or SEQ ID NO: 59. The vector can also optionally encode a polypeptide having a sequence as set forth as SEQ ID NO: 1, SEQ ID NO: 23, or SEQ ID NO: 39.

The immunogenic composition can include a nucleic acid sequence encoding a *P. ariasi* polypeptide(s) and/or a *P. perniciosus* polypeptide(s) (see U.S. Provisional Application No. 60/412,327, which is incorporated by reference herein in its entirety). In one embodiment, the *Lu. longipalpis* polypeptide(s) having an amino acid sequence as set forth as SEQ ID NO: 3, SEQ ID NO: 5, SEQ ID NO: 7, SEQ ID NO: 9, SEQ ID NO: 13, SEQ ID NO: 15, SEQ ID NO: 17, SEQ ID NO: 19, SEQ ID NO: 21, SEQ ID NO: 25, SEQ ID NO: 27, SEQ ID NO: 29, SEQ ID NO: 31, SEQ ID NO: 33, SEQ ID NO: 35, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 59, SEQ ID NO: 61, SEQ ID NO: 63, SEQ ID NO: 65, or SEQ ID NO: 67, a conservative variant, a homolog, an immunogenic fragment, or a fusion protein thereof, are encoded by the same recombinant vector as a *P. ariasi* polypeptide(s) and/or a *P. perniciosus* polypeptide(s). In another embodiment, the *Lu. longipalpis* polypeptide(s), a *P. ariasi* polypeptide(s) and/or a *P. perniciosus* polypeptide(s), are encoded by different recombinant vectors.

The *Lu. longipalpis* polypeptide can be administered by any means known to one of skill in the art (See Banga, A., "Parenteral Controlled Delivery of Therapeutic Peptides and Proteins," *Therapeutic Peptides and Proteins*, Technomic Publishing Co., Inc., Lancaster, Pa., 1995) such as by intramuscular (IM), intradermal (ID), subcutaneous (SC), or intravenous injection, but even oral, nasal, or anal administration is contemplated. In one embodiment, administration is by subcutaneous, intradermal, or intramuscular injection using a needleless injector (BIOJECTOR™, Bioject, Oreg., USA).

To extend the time during which the peptide or protein is available to stimulate a response, the peptide or protein can be provided as an implant, an oily injection, or as a particulate system. The particulate system can be a microparticle, a microcapsule, a microsphere, a nanocapsule, or similar particle. (see, for example, Banja, supra). A particulate carrier based on a synthetic polymer has been shown to act as an adjuvant to enhance the immune response, in addition to providing a controlled release. Aluminum salts may also be used as adjuvants to produce a humoral immune response. Thus, in one embodiment, a *Lu. longipalpis* polypeptide is administered in a manner to induce a humoral response.

In another embodiment, a *Lu. longipalpis* polypeptide is administered in a manner to direct the immune response to a cellular response (that is, a CTL response), rather than a humoral (antibody) response. A number of means for inducing cellular responses, both in vitro and in vivo, are known. Lipids have been identified as agents capable of assisting in priming CTL in vivo against various antigens. For example, as described in U.S. Pat. No. 5,662,907, palmitic acid residues can be attached to the alpha and epsilon amino groups of a lysine residue and then linked (for example, via one or more linking residues, such as glycine, glycine-glycine, serine, serine-serine, or the like) to an immunogenic peptide. The lipidated peptide can then be injected directly in a micellar form, incorporated in a liposome, or emulsified in an adjuvant. As another example, *E. coli* lipoproteins, such as tripalmitoyl-S-glycerylcysteinylseryl-serine can be used to prime tumor specific CTL when covalently attached to an appropriate peptide (see, Deres et al., *Nature* 342:561, 1989). Further, as the induction of neutralizing antibodies can also be primed with the same molecule conjugated to a peptide which displays an appropriate epitope, the two compositions can be combined to elicit both humoral and cell-mediated responses where that is deemed desirable.

In yet another embodiment, an MHC class II-restricted T-helper epitope is added to the polypeptide of the disclosure to induce T-helper cells to secrete cytokines in the microenvironment to activate CTL precursor cells. The technique further involves adding short lipid molecules to retain the construct at the site of the injection for several days to localize the antigen at the site of the injection and enhance its proximity to dendritic cells or other "professional" antigen presenting cells over a period of time (see Chesnut et al., "Design and Testing of Peptide-Based Cytotoxic T-Cell-Mediated Immunotherapeutics to Treat Infectious Diseases and Cancer," Powell, et al., (eds.), *Vaccine Design, the Subunit and Adjuvant Approach*, Plenum Press, New York, 1995).

An immunogenic composition or a vaccine according to the disclosure can be prepared in accordance with standard techniques well known to those skilled in the pharmaceutical or veterinary art. Such compositions can be administered in dosages and by techniques well known to those skilled in the medical or veterinary arts, taking into consideration such factors as the age, sex, weight, species, and condition of the particular subject, and the route of administration. The immunogenic composition or the vaccine can be administered alone, or in combination with adjuvant(s) and/or with other antigen(s). The other antigen(s) can be a *Leishmania* antigen. In one embodiment, the *Leishmania* antigen is the A2 antigen, such as the A2 antigen from *L. infantum* (see Published PCT Patent Application No. WO 95/06729 and in particular the sequence given in SEQ ID NO:2). The other antigen(s) can be present in the composition as a protein, or as an immunological fragment thereof (for example, an epitope), or as an insert in an expression vector (for example, recombinant viral vector, recombinant plasmid, in particular the pVR1012 (Vical Inc.; Hartikka J. et al., *Human Gene Therapy* 7:1205-1217, 1996)).

Any immunogenic composition, vaccine, or therapeutic composition according to the disclosure can be mixed with an adjuvant.

Polypeptide-Based Compositions:

In several embodiments, the polypeptide-based immunogenic compositions and vaccines according to the disclosure are formulated with (1) vitamin E, saponin (for example, QUIL A™, QS21™), aluminum hydroxide, aluminum phosphate, aluminum oxide ("Vaccine Design, The subunit and adjuvant approach," *Pharmaceutical Biotechnology*, vol. 6, Edited by Micheal F. Powell and Mark J. Newman, 1995, Plenum Press New York), (2) an acrylic acid or methacrylic acid polymer, a polymer of maleic anhydride and of alkenyl derivative, (3) an immunostimulating sequence (ISS), in particular an oligodeoxyribonucleotidic sequence bearing one or more non-methylated CpG groups (Klinman D M. et al., *Proc. Natl. Acad. Sci. USA* 93:2879-2883, 1996; Published PCT Application No. WO 98/16247), (4) to formulate the immunogenic or vaccine preparation in the form of an oil-in-water emulsion, in particular the SPT emulsion described on page 147 of "Vaccine Design, The Subunit and Adjuvant Approach" edited by M. Powell and M. Newman, Plenum Press, 1995, and the emulsion MF59 described on page 183 of this same book, (5) cytokines, or (6) combinations or mixtures thereof.

The cytokines (5) that can be added to the composition, include, but are not limited to, GM-CSF (granulocyte-macrophage colony stimulating factor) or cytokines inducing Th1 (for example, IL-12). All these cytokines can be added to the composition as a protein or as a vector encoding this cytokine protein. In one embodiment, the cytokines are from canine origin, for example, canine GM-CSF, for which a gene sequence has been deposited at the GenBank database (Accession No. S49738). This sequence can be used to create the vector in a manner similar to what was made in the Published PCT Patent Application No. WO 00/77210.

In one specific, non-limiting example the adjuvant contains two or more of an emulsifier, a micelle-forming agent, and an oil. Suitable emulsifiers, micelle-forming agents, and oils are detailed in U.S. Pat. Nos. 5,585,103; 5,709,860; 5,270,202; and 5,695,770, all of which are incorporated by reference. An emulsifier is any molecule that allows the components of the emulsion to remain as a stable emulsion. Such emulsifiers include polysorbate 80 (Sorbitan-mono-9-octadecenoate-poly(oxy-1,2-ethanediyl); manufactured by ICI Americas, Wilmington, Del.), polysorbate 20, polysorbate 21, polysorbate 40, polysorbate 60, polysorbate 61, polysorbate 85, dodecyl-N,N-dimethyl-3-ammonio-1-propanesulfonate, TEEPOL HB7™, and SPAN 80™ SPAN 85™, ethoxylated fatty alcohols, ethoxylated fatty acids, ethoxylated castor oil (hydrogenated or not). In one embodiment, these emulsifiers are provided in an amount of approximately 0.05 to approximately 0.5%. In another embodiment, these emulsifiers are provided in an amount of approximately 0.2%. A micelle forming agent is an agent which is able to stabilize the emulsion formed with the other components such that a micelle-like structure is formed.

Examples of such agents include polymer surfactants described by BASF Wyandotte publications, for example, Schmolka, *J. Am. Oil. Chem. Soc.* 54:110, 1977, and Hunter et al., *J. Immunol.* 129:1244, 1981, PLURONIC™ L62LF, L101, L121, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between about 0 and about 2, as defined by Hunter and Bennett, *J. Immun.* 133:3167, 1984. In one embodiment, the agent can be provided in an effective amount, for example between about 0.5 and about 10%. In another embodiment, the agent can be provided in an effective amount, for example between about 1.25 and about 5%.

In one embodiment, the oil included in the composition is chosen to promote the retention of the antigen in oil-in-water emulsion, for instance, to provide a vehicle for the desired antigen. In another embodiment, the oil has a melting temperature of less than about 65° C. such that emulsion is formed either at room temperature (about 20° C. to about 25° C.), or once the temperature of the emulsion is brought down to room temperature.

The oil-in-water emulsion (4) can be based in particular on light liquid paraffin oil (European Pharmacopea type); isoprenoid oil such as squalane, squalene, EICOSANE™ or tetratetracontane; oil resulting from the oligomerization of alkenes, in particular of isobutene or decene; esters of acids or of alcohols containing a linear alkyl group, more particularly plant oils, ethyl oleate, propylene glycol di(caprylate/caprate), glyceryl tri(caprylate/caprate) or propylene glycol dioleate; esters of branched fatty acids or alcohols, in particular isostearic acid esters. The oil is used in combination with emulsifiers to form the emulsion. In several embodiments, the emulsifiers are nonionic surfactants, in particular esters of sorbitan, mannide (for example, anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, in particular the PLURONIC® products, especially L121. In one specific, non-limiting example, the oil is provided in an amount between about 1 and about 60%. In another specific, non-limiting example, the oil is provided in an amount between about 5 and about 30%. In one embodiment, the adjuvant is a mixture of emulsifiers, micelle-forming agent, and oil available under the name PROVAX® (IDEC Pharmaceuticals, San Diego, Calif.).

The acrylic acid or methacrylic acid polymers (2) can be cross-linked in particular with polyalkenyl ethers of sugars or of polyalcohols. These compounds are known under the term "carbomer" (*Pharmeuropa*, Vol. 8, No. 2, June 1996). A person skilled in the art may also refer to U.S. Pat. No. 2,909,462 (incorporated by reference) describing such acrylic polymers cross-linked with a polyhydroxylated compound containing at least 3 hydroxyl groups. In one embodiment, a polyhydroxylated compound contains not more than 8 hydroxyl groups. In another embodiment, the hydrogen atoms of at least 3 hydroxyls are replaced with unsaturated aliphatic radicals containing at least 2 carbon atoms. In other embodiments, radicals contain from about 2 to about 4 carbon atoms, for example, vinyls, allyls, and other ethylenically unsaturated groups. The unsaturated radicals can themselves contain other substituents, such as methyl. The products sold under the name CARBOPOL® (Noveon Inc., Ohio, USA) are particularly suitable. They are cross-linked with an allyl sucrose or with allylpentaerythritol. Among these, mention may be made of the products Carbopol® 974P, 934P, and 971P.

The copolymers of maleic anhydride and of an alkenyl derivative, such as the EMA® products (Monsanto) which are copolymers of maleic anhydride and of ethylene, may be linear or cross-linked, for example cross-linked with divinyl ether. Reference may be made to J. Fields et al., *Nature* 186:778-780, 1960 (incorporated by reference). In one embodiment, the acrylic acid or methacrylic acid polymers and the EMA® products are formed from units based on the following formula:

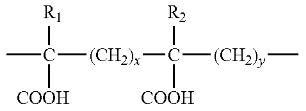

in which:

$R_1$ and $R_2$, which may be identical or different, represent H or $CH_3$ x=0 or 1, in one embodiment, x=1 y=1 or 2, with x+y=2.

For the EMA® products, x=0 and y=2. For the carbomers, x=y=1.

In one embodiment, the dissolution of these polymers in water leads to an acid solution, which is neutralized to physiological pH, in order to give to the subject the adjuvant solution into which the immunogenic composition or the vaccine itself is incorporated. The carboxyl groups of the polymer are then partly in $COO^-$ form.

In one embodiment, a solution of adjuvant, especially of carbomer, is prepared in distilled water. In another embodiment, a solution of adjuvant, especially of carbomer, is prepared in the presence of sodium chloride, the solution obtained being at acidic pH. In another embodiment, this stock solution is diluted by adding it to the desired quantity (for obtaining the desired final concentration), or a substantial part thereof, of water charged with NaCl. In yet another embodiment, stock solution is diluted by adding it to the desired quantity of physiological saline (NaCl 9 g/l) all at once in several portions with concomitant or subsequent neutralization (pH 7.3 to 7.4). In one embodiment, the stock solution is neutralized with NaOH. This solution at physiological pH is used as it is for mixing with the immunogenic composition or with the vaccine, which may be especially stored in freeze-dried, liquid or frozen form.

In one embodiment, the polymer concentration in the final vaccine composition is from about 0.01 to about 1.5% W/V. In another embodiment, the final vaccine composition is from about 0.05 to about 1% W/V. In yet another embodiment, the final vaccine composition is from about 0.1 to about 0.4% W/V.

Lipids have been identified as agents capable of stimulating the immune response for various antigens. For example, as described in U.S. Pat. No. 5,662,907, palmitic acid residues can be attached to the alpha and epsilon amino groups of a lysine residue and then linked (for example, via one or more linking residues, such as glycine, glycine-glycine, serine, serine-serine, or the like) to an immunogenic peptide. The lipidated peptide can then be injected directly in a micellar form, incorporated in a liposome, or emulsified in an adjuvant. As another example, *E. coli* lipoproteins, such as tripalmitoyl-S-glycerylcysteinylseryl-serine, can be used.

To extend the time during which the peptide or protein is available to stimulate a response, the peptide or protein can be provided as an implant, an oily injection, or as a particulate system. The particulate system can be a microparticle, a microcapsule, a microsphere, a nanocapsule, or similar particle. (see, for example, Banja, supra). A particulate excipient based on a synthetic polymer has been shown to act as an adjuvant to enhance the immune response, in addition to providing a controlled release.

Plasmid-Based Compositions:

In one embodiment, the plasmid-based compositions is formulated with cationic lipids, in particular with cationic lipids containing a quaternary ammonium salt having the following formula:

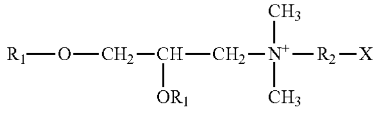

in which R1 is a saturated or unsaturated linear aliphatic radical from 12 to 18 carbon atoms, R2 is another aliphatic radical comprising from 2 to 3 carbon atoms, and X is an hydroxyl or amine group.

In one embodiment, DMRIE (N-(2-hydroxyethyl)-N,N-dimethyl-2,3-bis(tetradecyloxy)-1-propanammonium; Published PCT Application No. WO 96/34109) is the cationic lipid. In another embodiment, the cationic lipid is in association with a neutral lipid, for example DOPE (dioleoyl-phosphatidyl-ethanolamine; Behr J. P., *Bioconjugate Chemistry* 5:382-389, 1994), in order to form the DMRIE-DOPE. In yet another embodiment, the mixture is made extemporaneously about 10 minutes to about 60 minutes before administration. In another embodiment, the mixture is made extemporaneously about 30 minutes before administration. In one embodiment, the molar ratio DMRIE/DOPE is from about 95/5 to about 5/95. In another embodiment, the molar ratio DMRIE/DOPE is about 1/1. In one embodiment, the weight ratio plasmid/DMRIE or DMRIE-DOPE adjuvant is from about 50/1 to about 1/10. In another embodiment, the weight ratio plasmid/DMRIE or DMRIE-DOPE adjuvant is from about 10/1 to about 1/5. In yet another embodiment, the weight ratio plasmid/DMRIE or DMRIE-DOPE adjuvant is from about 1/1 to about 1/2.

In one embodiment, a cytokine or non-methylated CpG groups is added to the composition, as described above for polypeptide-based compositions. The addition can be done advantageously by a plasmid encoding the cytokine.

Viral Vector-Based Composition:

The recombinant viral vector-based composition can be supplemented with fMLP (N-formyl-methionyl-leucyl-phenylalanine; U.S. Pat. No. 6,017,537) and/or acrylic acid or methacrylic acid polymer adjuvant as described above for polypeptide-based compositions. They can also be formulated with emulsions as described above.

In one embodiment, cytokines, non-methylated CpG groups, or emulsions are added to the composition as described above for polypeptide-based compositions. The addition can be done advantageously by a viral vector encoding said cytokine.

The immunogenic compositions and vaccines according to the disclosure are conserved and stored either in formulated form at 5° C., or in lyophilized form. In one embodiment, the immunogenic compositions and vaccines according to the disclosure are conserved and stored either in formulated form at 5° C., or in lyophilized form with a stabilizer. Freeze-drying can be done according to well-known standard freeze-drying procedures. The pharmaceutically acceptable stabilizers may be SPGA (sucrose phosphate glutamate albumin) (Bovarnik et al., *J. Bacteriology* 59:509, 1950), carbohydrates (for example, sorbitol, mannitol, lactose, sucrose, glucose, dextran, trehalose), sodium glutamate (Tsvetkov T. et al., *Cryobiology* 20(3):318-23, 1983; Israeli E. et al., *Cryobiology* 30(5):519-23, 1993), proteins such as peptone, albumin, or casein, protein containing agents such as skimmed milk (Mills C K et al., *Cryobiology* 25(2):148-52, 1988; Wolff E. et al., *Cryobiology* 27(5):569-75, 1990), and buffers (for example, phosphate buffer, alkaline metal phosphate buffer). An adjuvant may be used to make soluble the freeze-dried preparations.

Methods of Immunization

The present disclosure provides methods for inducing an immune response to a *Lutzomyia* sand fly polypeptide in a subject. The present disclosure provides further methods for inhibiting or preventing leishmaniasis in a subject.

These methods include the administration of at least one immunogenic composition or vaccine according to the disclosure.

An immunogenic composition or a vaccine according to the disclosure can be prepared in accordance with standard techniques well known to those skilled in the pharmaceutical or veterinary art. Such compositions can be administered in dosages and by techniques well known to those skilled in the medical or veterinary arts, taking into consideration such factors as the age, sex, weight, species, and condition of the particular subject, and the route of administration.

If more than one administration is required, they can be administered concurrently (for example, different compositions given during the same period of time via the same or different routes, or a same composition given in the same period of time via different routes), or sequentially (for example, the same or different compositions given at least two times via the same or different routes). In one embodiment, the delay between two sequential administrations is from about 1 week to about 6 months. In another embodiment, the delay is from about 3 weeks to about 6 weeks. In yet another embodiment, the delay is from about 4 weeks. Following vaccination, annual boost administrations may be done. Advantageously, in a prime-boost vaccination schedule, at least one prime-administration can be done with a composition containing a plasmid according to the disclosure, following by at least one booster administration done with a composition containing a recombinant viral vector according to the disclosure, on the condition that a same *Lu. longipalpis* salivary polypeptide is present twice, coded by the plasmid and by the viral vector. Alternatively, the booster administration can be done with a composition containing a polypeptide according to the disclosure, on the condition that a same *Lu. longipalpis* salivary polypeptide is present twice, coded by the prime-administration plasmid and in the booster polypeptide-based composition.

In such compositions the antigen(s) may be in admixture with a suitable vehicle or excipient such as sterile water, physiological saline, glucose, or the like. The compositions can contain auxiliary substances such as wetting or emulsifying agents, pH buffering agents, adjuvants, gelling, or viscosity enhancing additives, preservatives, flavoring agents, colors, and the like, depending upon the route of administration and the preparation desired. Standard texts, such as Remington's Pharmaceutical Science, 17th edition, 1985, incorporated herein by reference, may be consulted to prepare suitable preparations, without undue experimentation. The compositions can also be lyophilized.

Suitable dosages can also be based upon the examples below. For polypeptide-based compositions, the route of administration can be ID, IM, SC, intravenous, oral, nasal, or anal. This administration can be made with a syringe and a needle or with a needle-less apparatus like, for example, Biojector™ (Bioject, Oreg., USA). In several embodiments, polypeptide dosages can be from about 1 to 250 μg/ml, from about 15 to about 150 μg/dose, or from about 20 to about 100 μg/dose. In another embodiment, using a needle-less apparatus the volume of a dose can be between about 0.1 ml and about 0.5 ml. In yet another embodiment, using a needle-less apparatus the volume of a dose can be about 0.25 ml. Administration with multiple points of injection is preferred. In one embodiment, for conventional injection with a syringe and a needle, the volumes are from about 0.1 to about 2 ml. In another embodiment, for conventional injection with a syringe and a needle, the volumes are from about 0.5 to about 1 ml.

For plasmid-based compositions, the route of administration can be ID, IM, SC, intravenous, oral, nasal, or anal. This administration can be made with a syringe and a needle or with a needle-less apparatus like, for example, Biojector™.

The dosage is from about 50 μg to about 500 μg per plasmid. When DMRIE-DOPE is added, about 100 μg per plasmid is preferred. In one embodiment, when canine GM-CSF or other cytokine is used, the plasmid encoding this protein is present at a dosage from about 200 μg to about 500 μg. In another embodiment, the plasmid encoding this protein is present at a dosage of about 200 μg. In one embodiment, using a needle-less apparatus, the volume of a dose can be between about 0.1 ml and about 0.5 ml. In another embodiment, the volume of a dose can be about 0.25 ml. In yet another embodiment, administration is performed using multiple points of injection. In one embodiment, for conventional injection with a syringe and a needle, the volumes are from about 0.1 to about 2 ml. In another embodiment, the volumes are from about 0.5 to about 1 ml. The dosage are the same than mentioned above.

For recombinant viral vector-based compositions, the route of administration can be ID, IM, SC, intravenous, oral, nasal, or anal. This administration can be made with a syringe and a needle or with a needle-less apparatus like, for example, Biojector™. The dosage is from about $10^3$ pfu to about $10^9$ pfu per recombinant poxvirus vector. In one embodiment, when the vector is a canarypox virus, the dosage is from about $10^5$ pfu to about $10^9$ pfu. In another embodiment, the dosage is from about $10^6$ pfu to about $10^8$ pfu. In one embodiment, the volume of needle-less apparatus doses could be between about 0.1 ml and about 0.5 ml. In another embodiment, the volume of needle-less apparatus dose is 0.25 ml. In yet another embodiment, administration is performed using multiple points of injection. In one embodiment, for conventional injection with a syringe and a needle, the volumes are from about 0.1 to about 2 ml. In another embodiment, the volumes are from about 0.5 to about 1 ml. The dosages are the same as mentioned above. In one embodiment, when a syringe with a needle is used, the injection is IM.

Advantageously for the prime boost administration regimen, the prime-administration is made with a plasmid-based composition and the boost administration is made with a recombinant viral vector-based composition. In one embodiment, the boost administration is made with a canarypox vector. Both priming and boosting administrations include vectors encoding at least one identical *Lu. longipalpis* salivary antigens, and optionally *Leishmania* A2 antigens. The dosage of plasmids and recombinant viral vectors are the same as above. Optionally, the boost administration can be done with a polypeptide-based composition. In this case, the dosage of polypeptide is from about 1 to about 250 μg/ml, from about 15 to about 150 μg/dose, or from about 20 to about 100 μg/dose.

Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response) and U.S. Pat. No. 5,593,972 and U.S. Pat. No. 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and QUIL A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 μg encapsulated in ISCOMS™ have been found to produce class I mediated CTL responses (Takahashi et al., *Nature* 344:873, 1990).

In another approach to using nucleic acids for immunization, a *Lu. longipalpis* polypeptide, or an immunogenic fragment thereof, can also be expressed by attenuated viral hosts or vectors or bacterial vectors. Recombinant vaccinia virus, adeno-associated virus (AAV), herpes virus, retrovirus, or other viral vectors can be used to express the peptide or protein, thereby eliciting a CTL response. For example, vaccinia vectors and methods useful in immunization protocols are described in U.S. Pat. No. 4,722,848. BCG (Bacillus Calmette Guerin) provides another vector for expression of the peptides (see Stover, *Nature* 351:456-460, 1991).

In one embodiment, a nucleic acid encoding a *Lu. longipalpis* polypeptide, or an immunogenic fragment thereof, is introduced directly into cells. For example, the nucleic acid may be loaded onto gold microspheres by standard methods and introduced into the skin by a device such as Bio-Rad's Helios™ Gene Gun. A needless injector can also be utilized, such as a Bioinjector2000™. The nucleic acids can be "naked," consisting of plasmids under control of a strong promoter. Typically, the DNA is injected into muscle, although it can also be injected directly into other sites. Exemplary dosages for injection are around 0.5 μg/kg to about 50 mg/kg, and typically are about 0.005 mg/kg to about 5 mg/kg (see, for example, U.S. Pat. No. 5,589,466). In one embodiment, a prime-boost strategy for immunization is utilized. Thus, in one embodiment, a nucleic acid encoding a *Lu. longipalpis* polypeptide is administered to the subject, followed by immunization with an attenuated or inactivated form of *Leishmania.*

The immunogenic compositions and the vaccines disclosed herein can be administered for preventative and therapeutic treatments. In therapeutic applications, compositions are administered to a subject suffering from a disease, such as *Leishmaniasis*, in a therapeutically effective amount, which is an amount sufficient to cure or at least partially arrest the disease or a sign or symptom of the disease. Amounts effective for this use will depend upon the severity of the disease and the general state of the subject's health. An effective amount of the compound is that which provides either subjective relief of a symptom(s) or an objectively identifiable improvement as noted by the clinician or other qualified observer.

Single or multiple administrations of the compositions are administered depending on the dosage and frequency as required and tolerated by the subject. In one embodiment, the dosage is administered once as a bolus, but in another embodiment can be applied periodically until a therapeutic result is achieved. Generally, the dose is sufficient to treat or ameliorate symptoms or signs of disease without producing unacceptable toxicity to the subject.

As noted above, the dosage of the composition varies depending on the weight, age, sex, and method of administration. The dosage can also be adjusted by the individual physician as called for based on the particular circumstances. The compositions can be administered conventionally as vaccines containing the active composition as a predetermined quantity of active material calculated to produce the desired therapeutic or immunologic effect in association with the required pharmaceutically acceptable carrier or diluent (for instance, carrier or vehicle). For example, about 50 μg of a DNA construct vaccine of the present disclosure can be injected intradermally three times at two week intervals to produce the desired therapeutic or immunologic effect. In another embodiment, a about 1 mg/Kg dosage of a protein vaccine of the present disclosure can be injected intradermally three times at two week intervals to produce the desired therapeutic or immunologic effect.

A vaccine is provided herein that includes a *Lu. longipalpis* polypeptide or polynucleotide. Administration of the vaccine to a subject, such as a human or veterinary subject, results in resistance to infection with *Leishmania*. In one embodiment, the subject is a human subject. In another embodiment, the subject is a canine subject, such as a dog.

Methods and Kits for the Diagnosis of *Leishmania* Infection

It is disclosed herein that individuals who experience an anti-*Leishmania* DTH response conversion also have an increase in antibodies against *Lu. Longipalpis* polypeptide salivary proteins. Thus, the presence or absence of antibodies to *Lu. Longipalpis* polypeptide salivary proteins can be used to ascertain if a subject has a *Leishmania* infection.

A method is disclosed herein for diagnosing infection with *Leishmania* by detecting the presence of antibodies that specifically bind one or more polypeptides having an amino acid sequence as set forth as SEQ ID NO: 3, SEQ ID NO: 5, SEQ ID NO: 7, SEQ ID NO: 9, SEQ ID NO: 13, SEQ ID NO: 15, SEQ ID NO: 17, SEQ ID NO: 19, SEQ ID NO: 21, SEQ ID NO: 25, SEQ ID NO: 27, SEQ ID NO: 29, SEQ ID NO: 31, SEQ ID NO: 33, SEQ ID NO: 35, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 59, SEQ ID NO: 61, SEQ ID NO: 63, SEQ ID NO: 65, or SEQ ID NO: 67, or a polypeptide at least 80%, at least 90%, at least 95%, or at least 99% homologous to one of these polypeptides, a conservative variant, a homolog or an immunogenic fragment of one of these polypeptides. The method can utilize a single *Lu. Longipalpis* polypeptide or a combination of these polypeptides. In certain examples, the method of diagnosis detects antibodies that specifically bind at least 3, 6, or 10 of these polypeptides, or immunogenic fragments thereof.

In one embodiment, one or more *Lu. Longipalpis* polypeptide can be bound to a solid substrate. For example, the *Lu. Longipalpis* polypeptide having an amino acid sequence as set forth as SEQ ID NO: 3, SEQ ID NO: 5, SEQ ID NO: 7, SEQ ID NO: 9, SEQ ID NO: 13, SEQ ID NO: 15, SEQ ID NO: 17, SEQ ID NO: 19, SEQ ID NO: 21, SEQ ID NO: 25, SEQ ID NO: 27, SEQ ID NO: 29, SEQ ID NO: 31, SEQ ID NO: 33, SEQ ID NO: 35, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 59, SEQ ID NO: 61, SEQ ID NO: 63, SEQ ID NO: 65, or SEQ ID NO: 67 can be bound to the substrate. One of more of these polypeptides can be bound to the substrate, for example at least 3, 6, or 10 of these polypeptides, or an immunogenic fragment thereof. In one example, one or more polypeptides having a sequence set forth as one of SEQ ID NO: 3, SEQ ID NO: 11, SEQ ID NO: 19, SEQ ID NO: 29, SEQ ID NO: 55, or SEQ ID NO: 59 can be bound to the substrate. In another example, one or more *Lu. Longipalpis* a polypeptides having a sequence set forth as one of SEQ ID NO: 1, SEQ ID NO: 23, or SEQ ID NO: 39 can be bound to the substrate. In one specific, non-limiting example, at least six *Lu. Longipalpis* polypeptides are bound to a solid substrate, wherein each of the polypeptides comprises an amino acid sequence as set forth as SEQ ID NO: 3, SEQ ID NO: 11, SEQ ID NO: 19, SEQ ID NO: 29, SEQ ID NO: 55, or SEQ ID NO: 59, or an immunogenic fragment thereof. In another specific, non-limiting example, at least three *Lu. Longipalpis* polypeptides are bound to a solid substrate, wherein each of the polypeptides comprises an amino acid sequence as set forth as SEQ ID NO: 1, SEQ ID NO: 23, or SEQ ID NO: 39, or an immunogenic fragment thereof.

In one embodiment, two or more (for example at least 3, 6, or 10) *Lu. Longipalpis* polypeptides (or immunogenic fragments thereof) are applied to a solid substrate, for example as a series of "dots," such as in a "dot blot" assay. In another embodiment, two or more *Lu. Longipalpis* polypeptides are applied to a substrate such as in a linear array. In a further embodiment, *Lu. Longipalpis* polypeptides are applied to a membrane in a two-dimensional array. In this manner, the presence of antibodies to more than one *Lu. Longipalpis* polypeptide is assessed. Each *Lu. Longipalpis* polypeptide can be applied directly to the surface of a membrane in a single location or in a combination of locations.

The solid substrate can be a polystyrene bead, a membrane, a chip or a plate. A plastic or glass substrate can be utilized. In other embodiments, a membrane is utilized that is composed of porous materials such as nylon, nitrocellulose, cellulose acetate, glass fibers, and other porous polymers. The surface of a solid support may be activated by chemical processes that cause covalent linkage of polypeptide to the support. However, any other suitable method may be used for immobilizing a polypeptide to a solid support including, without limitation, ionic interactions, hydrophobic interactions, covalent interactions and the like. Once the polypeptide is applied to the substrate, the substrate can be contacted with a substance, such as protein-containing solution, which non-specifically saturates the binding sites thereon. Specific, non-limiting examples of a protein-containing solution include a solution made from powdered milk or serum albumin, such as bovine serum albumin A specimen (for example, sera, blood, plasma, urine, semen, saliva, sputum, lacrimal fluid, lymph fluid) is then added to the substrate, and the combined specimen and substrate are incubated for a sufficient time to allow specific binding. Specific binding of antibodies to the *Lu. Longipalpis* polypeptides disclosed herein, are then detected using any means known to one of skill in the art. In one embodiment, a labeled secondary antibody is used to detect the antibodies that specifically bind the *Lu. Longipalpis* polypeptides. The label can be a radiolabel (for example, $^{125}I$), an enzymatic label (for example, alkaline phosphatase or horseradish peroxidase), or a fluorescent label (for example, fluorescein isothiocyanate). Detection systems for these labels are known to one of skill in the art. Binding of the specimen, or a component of the specimen, to the *Lu. Longipalpis* polypeptide, as indicated by the presence of the marker, indicates infection with *Leishmania*.

In another embodiment, the specimen is adsorbed onto a solid substrate containing binding sites for polypeptides, such as antibody molecules. In one embodiment, the solid substrate is a polystyrene bead, a chip, a membrane or a plate. The substrate is thereafter contacted with a substance, such as a protein-containing solution that non-specifically saturates the binding sites thereon. The substrate is then washed with a buffer. A solution of one or more *Lu. Longipalpis* polypeptides is then added to the bound specimens. In one embodiment, the *Lu. Longipalpis* polypeptide is directly labeled. The labeling of the *Lu. Longipalpis* polypeptide can be brought about by use of any marker, such as by incorporation of a radioactive isotope or group, or by coupling this component to an enzyme, a dyestuff, for example a chromophoric moiety or a fluorescent group. The enzymes of use are those which can be colorimetrically, spectrophotometrically, or fluorimetrically determined. Non-limiting examples of enzymes for use in the present invention include enzymes from the group of oxidoreductases, such as catalase, peroxidase, glucose oxidase, beta-glucuronidase, beta-D-glucosidase, beta-D-galactosidase, urease and galactose oxidase. After the labeled *Lu. Longipalpis* polypeptide is incubated with the solid substrate, any unbound labeled *Lu. Longipalpis* polypeptide is removed by washing. Bound labeled *Lu. Longipalpis* polypeptide is then detected by an appropriate assay. Binding of the labeled *Lu. Longipalpis* polypeptide to the specimen, or to a component of the specimen, is indicative of infection with *Leishmania*.

In general, the incubation steps utilized in carrying out the procedures can be performed in a known manner, such as by incubating at temperatures between about 4° C. and about 25° C., for about 30 minutes to about 48 hours. Washings can be included with an aqueous solution such as a buffer, wherein the buffer is from about pH 6 to about pH 8, such as by using an isotonic saline solution of a pH of about 7.

Competitive binding assays are also of use in detecting infection with *Leishmania*. One of skill in the art, given the *Lu. Longipalpis* polypeptides disclosed herein, will readily be able to design additional assays, such as competitive binding assays, of use in detecting *Leishmania* infection.

In another embodiment, the *Lu. Longipalpis* polypeptides disclosed herein can be included in a diagnostic test kit. For example, a diagnostic test kit for detecting a *Leishmania* infection includes a solid substrate having applied thereon one or more *Lu. Longipalpis* polypeptide disclosed herein. In other embodiments, the kit includes written instructions and/or a container including a specified amount of labeled antibodies to immunoglobulins, such as IgG or IgM, or labeled secondary antibodies that bind antibodies from a species of interest. For example labeled antibodies can be provided that specifically detect dog or human immunoglobulins. The labeled antibodies can be fluorescently labeled, enzymatically labeled, or radiolabeled. Labeled antibodies used in the above-described test kits can be packaged in either solution form, or in lyophilized forms suitable for reconstitution.

In another embodiment the test kit includes a specified amount of one or more *Lu. Longipalpis* polypeptide described herein in a container, and written instructions. In one example, the *Lu. Longipalpis* polypeptide is directly labeled. In another example, the one or more *Lu. Longipalpis* polypeptide is unlabeled. If the *Lu. Longipalpis* polypeptide is unlabeled, a container can also be included with a detection reagent that specifically binds the *Lu. Longipalpis* polypeptide, such as a labeled monoclonal antibody. The kit can also optionally include a solid substrate for binding the specimen.

The above described process and test kit for detection of antibodies to the *Lu. Longipalpis* polypeptides disclosed herein can be utilized in many applications, including, but not limited to detecting *Leishmania* infection in a subject using the methods disclosed herein. The tests and kits disclosed herein can be used to detect the efficacy of a therapeutic treatment in a subject. In yet another embodiment, the tests and kits disclosed herein can also be used to assess a primary infection with *Leishmania* or to predict recovery from *Leishmania* infection by taking a body fluid from an infected subject, for example at various times following infection, and applying the above described detection procedures.

The disclosure is illustrated by the following non-limiting Examples.

EXAMPLES

Example 1

Library Construction

Sand Flies and Preparation of Salivary Gland Homogenate (SGH).

Sand fly *Lutzomyia longipalpis* salivary glands were obtained from colonized sand flies at Walter Reed Army Institute and at the National Institutes of Health.

Salivary glands dissected under a dissection microscope and collected in microfuge tubes in sterile phosphate buffered saline (PBS), pH 7.0 are stored in dry ice and transferred to −70° C. until use.

The salivary gland of *Lu. longipalpis* is a sac-like structure consisting of a unicellular epithelium layer surrounding a large lumen (Adler and Theodor, *Ann. Trop. Med. Parasitol.* 20:109, 1926). After a blood meal, the gland total protein content decreases to half or less from its ~1 μg value (Ribeiro et al., *Insect Biochem.* 19:409-412, 1989). Accordingly, most of the protein from the fly SGH must be destined for secretion. Indeed, SDS-PAGE of SGH reveals a low complexity composition consisting of ~12 major bands varying from 10-100 kD (Valenzuela et al., *J. Exp. Med.* 194:331-42, 2001). For SDS-PAGE, Tris-glycine gels (16%), 1 mm thick, and NUPAGE 12% BIS-tris gels were used (Invitrogen, Carlsbad, Calif.). Gels were run with either Tris-glycine or MOPS Nupage running buffer according to the manufacturer's instructions. To estimate the molecular weight of the samples, See BlueJ markers from Invitrogen (myosin, BSA, glutamic dehydrogenase, alcohol dehydrogenase, carbonic anhydrase, myoglobin, lysozyme, aprotinin, and insulin, chain B) were used.

SGH were treated with equal parts of 2×SDS sample buffer (8% SDS in Tris-HCl buffer, 0.5M, pH 6.8, 10% glycerol and 1% bromophenol blue dye). Thirty pairs of homogenized salivary glands per lane (approximately 30 μg protein) were applied when visualization of the protein bands stained with Coomassie blue was desired. For amino terminal sequencing of the salivary proteins, 40 homogenized pairs of glands were electrophoresed and transferred to polyvinylidene difluoride (PVDF) membrane using 10 mM CAPS, pH 11, 10% methanol as the transfer buffer on a Blot-Module for the XCell II Mini-Cell (Invitrogen, Carlsbad, Calif.). The membrane was stained with Coomassie blue in the absence of acetic acid. Stained bands were cut from the PVDF membrane and subjected to Edman degradation using a Procise sequencer (Perkin-Elmer Corp, Foster City, Calif.).

Salivary Gland cDNA Library Construction.

*Lu. longipalpis* salivary gland mRNA was isolated from 80 salivary gland pairs from adult females. The Micro-FastTrack mRNA isolation kit (Invitrogen, Carlsbad, Calif.) was used, yielding approximately 100 ng poly (A)+ mRNA. The PCR-based cDNA library was made following the instructions for the SMART cDNA library construction kit (Clontech, Palo Alto, Calif.). One hundred nanograms of *Lu. longipalpis* salivary gland mRNA was reverse transcribed to cDNA using Superscript II RNase H-reverse transcriptase (Gibco-BRL, Gaithersburg, Md.) and the CDS/3' primer (Clontech, Palo Alto, Calif.) for 1 hour at 42° C. Second strand synthesis was performed using a PCR-based protocol by using the SMART III primer (Clontech, Palo Alto, Calif.) as the sense primer and the CDS/3' primer as anti-sense primer, these two primers additionally, create at the ends of the nascent cDNA SfiI A and B sites respectively. Double strand cDNA synthesis was done on a Perkin Elmer 9700 Thermal cycler (Perkin Elmer Corp., Foster City, Calif.) and using the Advantage Klen-Taq DNA polymerase (Clontech, Palo Alto, Calif.). PCR conditions were the following: 94° C. for 2 minutes; 19 cycles of 94° C. for 10 seconds and 68° C. for 6 minutes. Double-stranded cDNA was immediately treated with proteinase K (0.8 μg/μl) for 20 minutes at 45° C. and washed three times with water using Amicon filters with a 100 kDa cut off (Millipore Corp., Bedford Mass.). The double-stranded cDNA was then digested with Sfi I for 2 hours at 50° C. (The Sfi I sites were inserted to the cDNA during the second strand synthesis using the SMART III and the CDS/3' primer). The cDNA was then fractionated using columns provided by the manufacturer (Clontech, Palo Alto, Calif.). Fractions containing cDNA of more than 400 base pairs (bp) were pooled, concentrated, and washed three times with water using an Amicon filter with a 100 kDa cut-off. The cDNA was concentrated to a volume of 7 μl. The concentrated cDNA was then ligated into a lambda triplex2 vector (Clontech, Palo Alto, Calif.), and the resulting ligation reaction was packed using the Gigapack gold III from Stratagene/Biocrest (Cedar Creek, Tenn.) following manufacturer's specifications. The obtained library was plated by infecting log phase XL1-blue cells (Clontech, Palo Alto, Calif.) and the amount of recombinants was determined by PCR using vector primers flanking the inserted cDNA and visualized on a 1.1% agarose gel with ethidium bromide (1.5 μg/ml).

Massive Sequencing of *Lu. longipalpis* Salivary Gland cDNA Library.

*Lu. longipalpis* salivary gland cDNA library was plated to approximately 200 plaques per plate (150 mm Petri dish). The plaques were randomly picked and transferred to a 96 well polypropylene plate containing 100 μl of water per well. The plate was covered and placed on a gyrator shaker for 1 hour at room temperature. Four microliters of a phage sample was used as a template for a PCR reaction to amplify random cDNAs. The primers used for this reaction were sequences from the triplex2 vector, the primers were named PT2F1 (5'-AAGTACTCT AGCAAT TGTGAGC-3') (SEQ ID NO: 71) which is positioned upstream of the cDNA of interest (5' end), and PT2R1 (5'-CTCTTCGCTATTACGC-CAGCT G-3') (SEQ ID NO: 72) which is positioned downstream of the cDNA of interest (3' end). Platinum Taq polymerase (Gibco-BRL, Gaithersburg, Md.) was used for these reactions. Amplification conditions were the following: 1 hold of 75° C. for 3 minutes, 1 hold of 94° C. for 3 minutes and 34 cycles of 94° C. for 30 seconds, 49° C. for 30 seconds and 72° C. for 1 minute and 20 seconds. Amplified products were visualized on a 1.1% agarose gel with ethidium bromide. Clean PCR was used as a template for a cycle sequencing reaction using the DTCS labeling kit from Beckman Coulter Inc. (Fullerton, Calif.). The primer used for sequencing (PT2F3) (5'-TCTCGGGAAGCGCGC-CATTGTGTT-3') (SEQ ID NO: 73) is upstream of the inserted cDNA and downstream of the primer PT2F1. Sequencing reaction was performed on a Perkin Elmer 9700 thermacycler. Conditions were 75° C. for 2 minutes, 94° C. for 4 minutes, and 30 cycles of 96° C. for 20 seconds, 50° C. for 20 seconds and 60° C. for 4 minutes.

After cycle sequencing the samples, a cleaning step was done using the multi-screen 96 well plate cleaning system from Millipore (Bedford, Mass.). The 96 well multi-screening plate was prepared by adding a fixed amount (according to the manufacturer's specifications) of Sephadex-50 (Amersham Pharmacia Biotech, Piscataway, N.J.) and 300 μL of deionized water. After 1 hour of incubation at room temperature, the water was removed from the multi screen plate by centrifugation at 750 g for 5 minutes. After the Sephadex in the multi-screen plate was partially dried, the whole cycle sequencing reaction was added to the center of each well, centrifuged at 750 g for 5 minutes and the clean sample was collected on a sequencing microtiter plate (Beckman Coulter, Fullerton, Calif.). The plate was then dried on Speed-Vac SC 110 model with a microtiter plate holder (Savant Instruments Inc, Holbrook, N.Y.). The dried samples were immediately resuspended with 25 μl of deionized ultrapure formamide (J.T. Baker, Phillipsburg, N.J.), and one drop of mineral oil was added to the top of each sample. Samples were sequenced immediately on a CEQ 2000 DNA sequencing instrument (Beckman Coulter Inc., Fullerton, Calif.) or stored at −30° C. The entire cDNA of selected genes was fully sequenced using custom primers using a CEQ 2000 DNA sequencing instrument (Beckman Coulter Inc., Fullerton. Calif.) as described above.

DNA Vaccine Construction and Description of the VR1020 Vector.

The genes coding for the predicted secreted proteins were amplified from *Lu. longipalpis* specific cDNA by PCR using Platinum Taq polymerase (GIBCO BRL, Gaithersburg, Md.) and specific primers carrying the Predicted N-terminus (Forward primer); and the stop codon (Reverse primer) of the selected cDNA.

The PCR product was immediately cloned into the custom made VR-2001-TOPO (derived fromVR1020 vector) cloning vector following manufacturers specifications (Invitrogen, Carlsbad. Calif.). The ligation mixture was used to transform TOP10 cells (Invitrogen, Carlsbad. Calif.) and the cells were incubated overnight at 37° C. Eight colonies were picked and mixed with 10 μl of sterile water. Five microliters of each sample were transferred to Luria broth (LB) with ampicillin (100 μg/ml) and grown at 37° C. The other 5 μl were used as a template for a PCR reaction using two vector-specific primers from the PCRII vector to confirm the presence of the insert and for sequencing analysis. After visualization of the PCR product on a 1.1% agarose gel, the eight PCR products were completely sequenced as described above using a CEQ2000 DNA sequencing instrument (Beckman Coulter). Cells containing the plasmid carrying the selected *Lu. longipalpis* gene were grown overnight at 37° C. on Luria broth with ampicillin (100 μg/ml), and plasmid isolation was performed using the Wizard Miniprep kit (Promega, Madison, Wis.). The VR-2001-TOPO (a variant of the VR1020 plasmid from Vical) plasmid contains a kanamycin resistance gene, the human cytomegalovirus promoter, and the tissue plasminogen activator signal peptide upstream of the TOPO TA cloning site. The sample that contained the sequence from the start codon to the stop codon in the right orientation and in the correct open-reading-frame following the nucleotide sequence encoding the tissue plasminogen activator signal peptide was chosen.

Plasmids were transformed into the TOP-10 strain of *E. coli* (Invitrogen, Carlsbad. Calif.) according to the manufacturer's instructions. The transformed bacteria were grown in LB medium and the plasmid was subsequently purified using the commercial plasmid purification kit Megaprep (Qiagen, Valencia. Calif.). Each plasmid was named according to the name of the polypeptide. Thus pLJL34 is a plasmid encoding LJL34, and pLJM11 is a plasmid encoding LJM11 polypeptide, etc.

Study Population.

Sera used in the study using human subjects were obtained from an epidemiologic survey of visceral leishmaniasis (VL) in children less than 7 years of age in an endemic region of São Luiz, Maranhão State, in northeastern Brazil. During this prospective study, anti-*Leishmania* DTH and serology were performed twice a year during 1997 and 1998. Only children who had neither VL, a positive serology, nor DTH on the first survey were included in the study. None of the individuals in the data set had the disease, and all had negative responses to leishmanial antigen during the preceding 6-month period. Positivity in the anti-leishmanial tests reported here indicates a recent conversion determined by a sensitive and specific ELISA (Banal et al., *Am J Trop Med Hyg* 62:740-5, 200) and/or DTH test (Banal et al., ibid). To determine the cut-off value for IgG anti-*Lu. longipalpis* in ELISA assays, sera were obtained from children in the same age range from a nonendemic area. Assuming that recent seroconversion represents infection and that a positive DTH response is a marker of protection against leishmaniasis in subclinical cases, we classified children in two groups according to their anti-*Leishmania* responses: Group I, positive serology ($S^-\rightarrow S^+$) (n=15) and Group II, positive DTH ($DTH^-\rightarrow DTH^+$) (n=15).

Anti-Sand Fly Saliva Serology.

Anti-sand fly saliva serology ELISA was performed as previously described (Barral et al., ibid). Sera IgG subclasses were determined using anti-human IgG1, IgG3, or IgG4 alkaline-phosphatase conjugates (Sigma-Aldrich, St. Louis, Mo.). To determine IgE levels, sera were previously absorbed using Rheumatoid Factor. Anti-human IgE (Sigma-Aldrich, St. Louis, Mo.) was used in the ELISA.

Western Blots.

Western blots of salivary gland antigens were performed as previously described (Barral et al., ibid).

Statistical Analysis (Human Studies).

The non-parametric paired Wilcoxon test was used to compare levels of anti-*Lu. longipalpis* saliva antibodies in the same children at time 0 (beginning of survey) and after 6 months. P value<0.05 was established as the significance level. Graph Pad Prism software (San Diego. Calif.) was used to perform the statistical tests.

Example 2

DNA and Predicted Protein Sequence Analysis

DNA data derived from the mass sequencing project were analyzed by an in-house program written in VisualBASIC (Microsoft). This program removed vector and primer sequences from the raw sequence. Stripped sequences were compared to the NCBI non-redundant protein database using the program BlastX using the BLOSUM-62 matrix (Altschul et al., *Nucleic Acids Research* 25:3389, 1997). DNA sequences were clustered by blasting the database against itself with a preselected threshold cutoff, usually $1e^{-10}$ (BlastN program) (Altschul et al., *Nucleic Acids Research* 25:3389, 1997). Sequences from the same cluster were aligned using ClustalX (Jeanmougin et al., *Trends Biochem. Sci.* 23:403, 1998). To find the cDNA sequences corresponding to the amino acid sequence obtained by Edman degradation of the proteins transferred to PVDF membranes from SDS-PAGE gels, a search program was written that checked these amino acid sequences against the three possible protein translations of each cDNA sequence obtained in the mass sequencing project. This was written using the same approach used in the BLOCKS (Henikoff et al., *Bioinformatics* 15:471, 1999) or Prosite (Bairoch, *Nucleic Acids Res.* 19 (Suppl.):2241, 1991) programs. Protein translations of the full-length clones were further processed to identify the predicted signal peptides using the Signal P program (Nielsen et al., *Protein Eng.* 10:1, 1997), available online Predicted signal peptide cleaved sites were compared to the N-terminus sequence obtained from Edman degradation of *Phlebotomus* salivary proteins. Estimation of isoelectric point and molecular weight of translated protein was performed using the DNA STAR program (DNASTAR). Full-length translated protein sequence information was compared with the non-redundant protein database of NCBI using the BLAST-P program (Altschul et al., *Nucleic Acids Research* 25:3389, 1997) and searched for motifs by submitting each sequence to the electronic database.

To characterize the primary structure of the main proteins of *Lu. longipalpis* SGH, SDS-PAGE gels were transferred to PVDF membranes, and the amino terminal sequence of each cut band by Edman degradation were estimated.

In addition, the following values were ascertained:

TABLE 1

Protein Characteristics

| Polypeptide name | Position of cleavage site | Molecular Weight (MW) of Unprocessed Protein | pI of Unprocessed Protein | Molecular Weight of Processed Protein | pI of Processed Protein |
|---|---|---|---|---|---|
| LJL34 | 19 | 31 | 9.14 | 28.9 | 9.1 |
| LJL18 | 19 | 18.7 | 6.42 | 16.4 | 6.1 |
| LJS193 | 20 | 34.5 | 6.59 | 32.2 | 6.3 |
| LJS201 | 23 | 11.2 | 4.89 | 8.7 | 4.8 |
| LJL13 | 19 | 28.7 | 5 | 26.6 | 4.9 |
| LJL23 | 21 | 37.4 | 9.15 | 35.1 | 9.1 |
| LJM10 | 19 | 18.8 | 8.73 | 16.7 | 8.6 |
| LJL143 | 23 | 35 | 8.4 | 32.5 | 8.3 |
| LJS142 | 20 | 18.9 | 6.43 | 16.7 | 6.5 |
| LJL17 | 20 | 12.3 | 4.36 | 10.2 | 4.4 |
| LJM06 | 19 | 18.6 | 8.79 | 16.5 | 8.7 |
| LJM17 | 18 | 47.3 | 5.92 | 45.2 | 5.7 |
| LJL04 | 17 | 31.1 | 10.1 | 29.3 | 10 |
| LJM114 | 24 | 17 | 7.58 | 14.3 | 5.6 |
| LJM111 | 18 | 45.2 | 4.9 | 43 | 4.9 |
| LJM78 | 20 | 39.4 | 7.54 | 37.3 | 7.7 |
| LJS238 | 20 | 6.9 | 7.92 | 4.8 | 6.7 |
| LJS169 | 22 | 14.1 | 4.64 | 11.6 | 4.5 |
| LJL11 | 24 | 63.4 | 6.49 | 60.8 | 6.7 |
| LJL08 | 23 | 9.5 | 8.76 | 7 | 8.8 |
| LJS105 | 19 | 9.5 | 4.85 | 7.4 | 4.7 |
| LJL09 | 18 | 73 | 5.65 | 71.1 | 5.6 |
| LJL38 | 20 | 4.8 | 3.66 | 2.5 | 3.3 |
| LJM04 | 20 | 16.2 | 8.91 | 13.9 | 9 |
| LJM26 | 17 | 50.7 | 5.77 | 48.8 | 5.8 |
| LJS03 | 19 | 17.3 | 4.27 | 15.2 | 4.2 |
| LJS192 | 23 | 12.1 | 4.29 | 9.7 | 4.2 |
| LJM19 | 22 | 13.4 | 4.26 | 10.8 | 4.2 |
| LJL138 | 19 | 45.9 | 9.42 | 43.8 | 9.5 |
| LJL15 | 19 | 18.7 | 6.2 | 16.5 | 6.1 |
| LJL91 | 19 | 18.5 | 5.82 | 16.4 | 5.8 |
| LJM11 | 24 | 45.3 | 9.35 | 42.7 | 9.4 |
| LJS138 | 20 | 18.5 | 5.88 | 16.2 | 5.5 |

Example 3

Antibodies Against *Lu. longipalpis* Saliva

It has previously been shown that sera from children living in an area endemic for VL have anti-SGS IgG antibodies that differentially recognize salivary gland antigens. Individuals with a positive anti-*Leishmania* DTH response exhibited anti-*Lu. longipalpis* saliva antibodies. A positive correlation was observed between anti-*Lu. longipalpis* saliva antibodies and anti-*Leishmania* DTH, but no correlation was observed between anti-saliva antibodies and anti-*Leishmania* serology (Banal et al., ibid).

The change in humoral and cell-mediated anti-*Leishmania* responses in a 6-month follow up of individuals in an area endemic for VL as well as the change in anti-*Lu. longipalpis* saliva antibody responses in the same individuals was studied. Individuals (n=15) who converted to positive anti-*Leishmania* DTH significantly increased their anti-*Lu. longipalpis* IgG (FIG. 1A; P=0.02) and IgE antibody levels (FIG. 1B, P=0.002). IgG1 was the principal antibody subclass involved in the increase of anti-saliva antibodies in the group converting anti-*Leishmania* DTH (n=15) (FIG. 1C); no significant changes were observed in other IgG subclasses. The cut-off value for anti-*Lu. longipalpis* IgG in ELISAs was 0.045. A significant decrease in anti-saliva IgG antibody levels (P=0.035) was observed in sera from children who converted their anti-*Leishmania* serology (Group I) (FIG. 1A). No significant changes were observed in anti-saliva IgE in Group I (FIG. 1B). Although IgG anti-saliva levels in Group II children decreased in the 6-month period, a significant increase in IgG4 anti-saliva was observed in this group (P=0.0245; FIG. 1D).

Figure 2A:
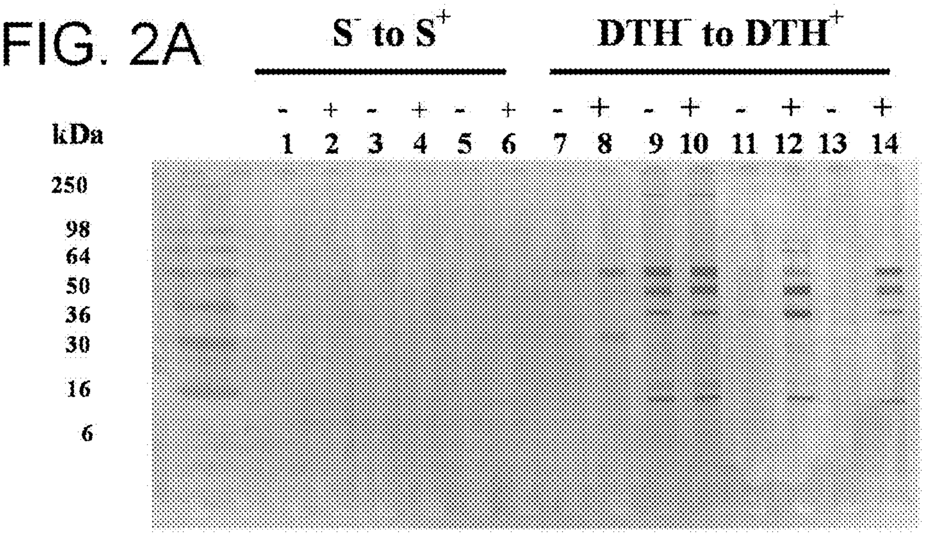
FIGS. 2A-2C are a set of two digital images and a bar graph showing salivary proteins recognized by Western blot analysis.
Figure 2B:
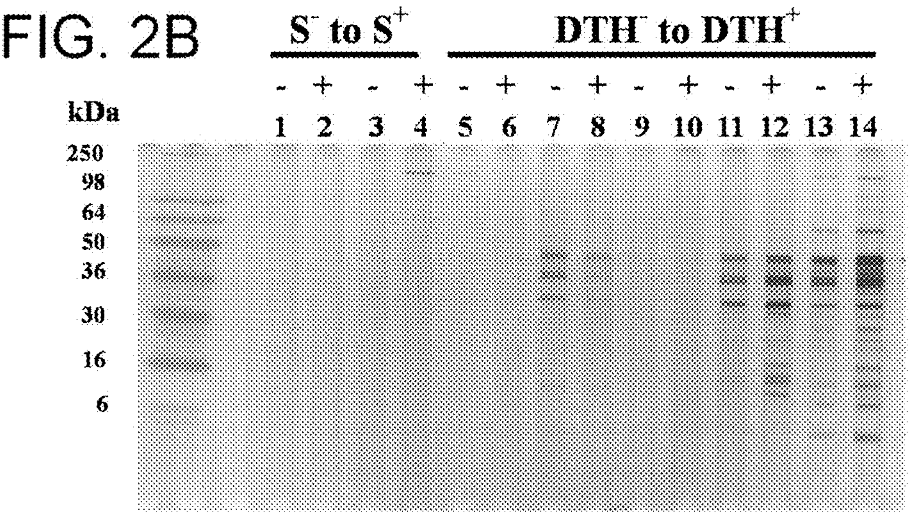

The number and pattern of *Lu. longipalpis* salivary proteins recognized by the sera of individuals who converted either from $S^- \rightarrow S^+$ or from $DTH^- \rightarrow DTH^+$ was evaluated by Western blot. From seven randomly selected sera of individuals who converted their anti-*Leishmania* serology, two poorly recognized two different salivary proteins of 33 kDa and 200 kDa, respectively (FIG. 2A, lane 4); the remaining sera did not recognize any salivary protein at any time point. Conversely, from 13 randomly selected sera of $DTH^- \rightarrow DTH^+$ individuals, 12 recognized a variety of salivary proteins with various intensities. FIGS. 2A and 2B show the diversity of salivary antigens recognized by these sera (lanes 7-14). Additionally, sera from six $DTH^- \rightarrow DTH^+$ individuals showed an increase in the number and/or intensity of salivary proteins recognition when comparing time 0 (−) and 6 months (+) time points (FIG. 2A, lanes 7(−) and 8(+), 11(−) and 12(+), 13(−) and 14(+); FIG. 2B, lanes 11(−) and 12(+), 13(−) and 14(+), and data not shown). Some individuals in the $DTH^- \rightarrow DTH^+$ group did not show any change from time 0 to 6 months (FIG. 2A, lanes 9(−) and 10(+); FIG. 2B, lanes 7(−) and 8(+)) or did not recognize any salivary protein (FIG. 2B, lanes 9(−) and 10(+)).

Figure 2C:
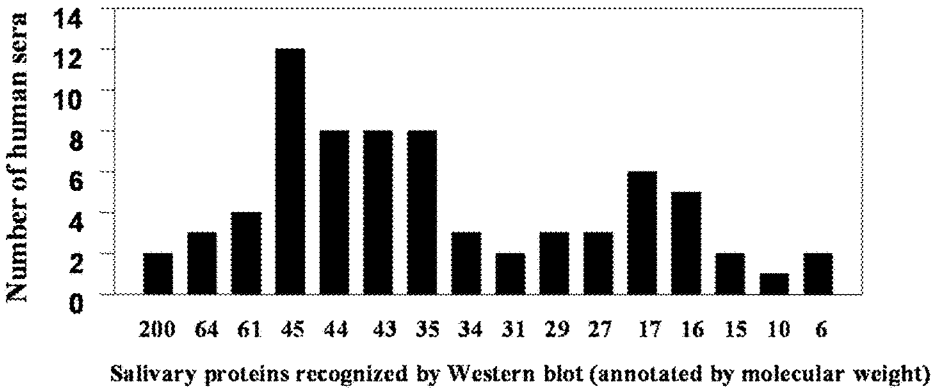

The sera of the $DTH^- \rightarrow DTH^+$ individuals recognized a total of 16 different salivary proteins; however, the frequency of recognition varies among these individuals (FIG. 2C). A salivary protein of 45 kDa was recognized by 12 sera, followed by proteins of 44 and 43 and 35 kDa recognized by 8 sera (each), a protein of 17 kDa by 6 sera, and a protein of 16 kDa by 5 sera. Other salivary proteins were recognized as well but with less frequency (3 sera or less, FIG. 2C).

Thus, Group II children, who convert their anti-*Leishmania* DTH, also present an increase in anti-sand fly saliva antibodies as evidenced by ELISA and Western blot. A correlation between anti-saliva antibody titers and anti-*Leishmania* DTH has been shown (Banal et al., ibid); the results presented herein show that development of anti-parasite DTH temporally coincides with development of anti-*Lu. longipalpis* saliva antibodies. Without being bound by theory, neutralization of sand fly salivary component(s) by antibodies or cellular response to salivary proteins allows for a more efficient mounting of an anti-*Leishmania* cell-mediated immune response, probably by developing a Th1 response against the parasite. Sand fly saliva components, such as maxadilan, are able to impair macrophage function (Charlab et al., *Proc Natl Acad Sci USA* 96:15155-60, 1999), which interferes with *Leishmania* survival and antigen presentation (Soares et al., *J. Immunol.* 160:1811-6, 1998). The higher antibody levels observed in $DTH^- \rightarrow DTH^+$ individuals suggest that mounting an immune response against anti-saliva components is linked to developing cell-mediated immunity against *Leishmania*.

The results presently reported by Western blot analysis showed that individuals who converted their anti-*Leishmania* serology practically did not recognize any salivary protein whereas individuals who converted their anti-*Leishmania* DTH recognized a number of different salivary proteins. Frequency of salivary antigens recognized by these sera reveals a cluster of only a few proteins, including antigens with an approximate molecular mass of 45, 44, 43, 35, 27 and 16 kDa (FIG. 2C).

Among these antigens, the recognition of at least two salivary proteins (45 kDa and 35 kDa), represent two of the highest frequencies of recognition by human sera. Surprisingly, only two sera recognized a protein in the range of 6 kDa, the molecular weight of maxadilan (Titus and Ribeiro, *Parasitol Today* 6:157-159, 1990) suggesting that, in humans, maxadilan may not induce a strong antibody response, although it could be a strong inducer of cellular immunity.

Individuals who converted their anti-*Leishmania* cell-mediated immunity exhibited increased IgG1 and IgE levels. IgG1 has been related to a human Th1 response. Elevation of IgE antibodies suggests the development of an immediate hypersensitivity, since IgE is considered a marker of Th2-type responses. Without being bound by theory, it is likely that a mixed Th2-type (related to immediate hypersensitivity) and Th1-like response (related to DTH) against saliva components coexist in individuals who recently converted their anti-*Leishmania* DTH. In fact, this type of mixed response was reported in individuals exposed to insect bites, where the host immune response against insect saliva starts with DTH response and evolves to a predominant immediate-type hypersensitivity and finally desensitization (Melanby, *Nature.* 158, 554-555.13, 1946).

As disclosed herein, in mice, immunization using *Lu. longipalpis* salivary genes resulted in a typical DTH and/or antibody response to *Lu. longipalpis* salivary proteins (see below), suggesting that *Lu. longipalpis* bites could induce Th1 and Th2 responses in humans. Of interest, the *P. papatasi* (SP15) salivary protein responsible for the DTH response in mice is highly homologous to the SL1 protein present in *Lu. longipalpis* saliva (Charlab et al., *Proc Natl Acad Sci USA* 96:15155-60, 1999). Without being bound by theory, the results presented herein suggest that a mixed anti-saliva response with both Th1 and Th2 components can help in establishing an anti-immune *Leishmania* response.

Example 4

DNA Vaccination in Mice

For genetic immunization, Swiss Webster mice were purchased from Taconic Farms. Mice were maintained in the NIAID Animal Care Facility under pathogen-free conditions. Mice were inoculated in the right ear with 30 μg of the plasmid encoding the selected cDNA from *Lu. longipalpis* suspended in 5 μl of PBS. Each group is boosted 2 weeks later using the same regimen. Mice were challenged on the opposite ear with salivary gland homogenate of *Lu. longipalpis* and delayed type hypersensitivity (DTH) response is measured 24 hours after the injection by measuring thickness and redness of ear (++: at least 2 mice with a good DTH response, +++: at least three mice had a good DTH response).

TABLE 2

DTH Response in Mice

| *Lutzomyia longipalpis* salivary gland cDNA | DTH response (thickness and redness) |
|---|---|
| pLJS201 | – |
| pLJM19 | ++ |
| pLJL91 | – |
| pLJM06 | – |
| pLJL15 | +++ |
| pLJM11 | – |
| pLJM17 | +++ |
| pLJL11 | – |
| pLJL08 | ++ |
| pLJL18 | ++ |
| pLJS142 | – |
| pLJL13 | – |
| pLJL34 | ++ |
| pLJM111 | +++ |
| pLJL17 | +++ |
| pLJM04 | – |
| pLJL23 | ++ |

*Delayed type hypersensitivity (DTH) response induced by injection of salivary gland homogenate on the ear of mice (group of three) previously immunized with salivary DNA vaccine. Mice were previously sensitized with specific DNA plasmids two times at two weeks interval then injected with salivary gland homogenate of the sand fly *Lutzomyia longipalpis*. DTH response was measured at 24 hours (thickness and redness of ear) after salivary gland homogenate injection. (++ = at least 2 mice had good DTH response, +++ at least three mice had a good DTH response).

Example 5

Production of an Immune Response in Dogs

In a first experiment DTH (delayed type hypersensitivity) reaction is performed in dogs with natural immunity against the leishmaniasis in order to determine which *Lu. longipalpis* salivary proteins are recognized by a protective immune response. These dogs with natural immunity survived without symptoms after two years of exposure in an endemic area. In a second experiment naive dogs are immunized with the *Lu. longipalpis* salivary gland protein expressed by a plasmid in order to evaluate the capability to induce a cellular immune response measured by DTH.

Twelve dogs approximately three years old with natural immunity against *Leishmaniasis* are injected via an intradermal route (ID) in the back after shaving, with 100 μg of each individual plasmid suspended in 100 μl of PBS. Each plasmid is injected at a different point. The points are separated by at least 3 cm to avoid interference between DTH responses. The negative control (100 μl of buffer) is also inoculated by ID route.

The DTH response is assessed 72 hours after injection by measuring the larger diameter of the skin tumefaction area. The results are expressed as the mean value of the tumefaction area for all the dogs and as a percentage of dogs having a positive DTH response. A positive DTH is a tumefaction area diameter greater than or equal to 4 mm at 72 hours after injection.

In a second study, 10 naïve dogs 4 to 6 months old are immunized by ID injection in 10 points (100 μl per point) in the right ear with a pool of the plasmids encoding a *Lu. longipalpis* polypeptide, 100 μg for each one suspended in 1000 μl of PBS. On day 21, dogs are injected in 10 points (100 μl per point) in the left ear and in 10 points (100 μl per point) in the belly with a pool of the plasmids, 100 μg for each one suspended in 2000 μl of PBS. All dogs are challenged on day 35 by inoculation by ID route in the back (after shaving), with 100 μg of each individual plasmid suspended in 100 μl of PBS. Each plasmid is injected at a different point. The points are separated by at least 3 cm to avoid interference. As a negative control, 100 μl of buffer is inoculated intradermally. The DTH response is assessed 72 hours after challenge, by measuring the larger diameter of the skin tumefaction area. The results are expressed as the mean value of the tumefaction area for all the dogs and as a percentage of dogs having a positive DTH response. A positive DTH is a tumefaction area diameter higher or equal of 4 mm at 72 hours after injection.

The results of this study show that plasmids can induce a cellular immunity in dogs after injection, a cellular immunity reveled by a DTH response. The variation of the DTH response level can be by the variation of the expression of the insert.

It will be apparent that the precise details of the methods described may be varied or modified without departing from the spirit of the described disclosure. We claim all such modifications and variations that fall within the scope and spirit of the claims below.

The invention claimed is:

1. An immunogenic composition, comprising:

a salivary *Lu. longipalpis* polypeptide, wherein the polypeptide comprises amino acid residues 23-115 of SEQ ID NO: 55; and a pharmaceutically acceptable carrier comprising an emulsifying agent, a gelling agent, or a liposome; or an aluminum salt adjuvant; or both.

2. The immunogenic composition of claim 1, wherein the polypeptide comprises the amino acid sequence of SEQ ID NO: 55.

3. A method for inducing an immune response in a mammal, comprising administering to the mammal an effective amount of the immunogenic composition of claim 1, thereby inducing an immune response in the mammal.

4. The method of claim 3, wherein the immune response comprises a T cell response.

5. The method of claim 3, wherein the mammal is a human.

6. The method of claim 3, wherein the immune response comprises a B cell response.

7. The method of claim 3, wherein the immune response comprises a Th1 response.

8. The method of claim 3, wherein the mammal is a non-human veterinary animal.

* * * * *